(12) United States Patent
Nishizawa et al.

(10) Patent No.: US 8,207,401 B2
(45) Date of Patent: Jun. 26, 2012

(54) A METHOD OF CREATING A PLANT IMPROVED IN TOLERANCE TO IRON DEFICIENCY

(75) Inventors: Naoko Nishizawa, Tokyo (JP); Satoshi Mori, Tokyo (JP); Takanori Kobayashi, Tokyo (JP); Yuko Ogo, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/451,000

(22) PCT Filed: Apr. 24, 2008

(86) PCT No.: PCT/JP2008/057918
§ 371 (c)(1),
(2), (4) Date: Jan. 5, 2010

(87) PCT Pub. No.: WO2008/136345
PCT Pub. Date: Nov. 13, 2008

(65) Prior Publication Data
US 2011/0138496 A1    Jun. 9, 2011

(30) Foreign Application Priority Data
Apr. 26, 2007 (JP) .................................. 2007-117725

(51) Int. Cl.
*C12N 15/82* (2006.01)
(52) U.S. Cl. ........................................................ 800/289
(58) Field of Classification Search .................. None
See application file for complete search history.

(56) References Cited

U.S. PATENT DOCUMENTS

| | | | |
|---|---|---|---|
| 6,897,300 B1 | 5/2005 | Mori et al. | |
| 2005/0095689 A1 | 5/2005 | Mori et al. | |
| 2006/0123505 A1 | 6/2006 | Kikuchi et al. | 800/278 |

FOREIGN PATENT DOCUMENTS

| | | |
|---|---|---|
| JP | 10-290694 | 11/1998 |
| JP | 2005-006599 | 1/2005 |

OTHER PUBLICATIONS

Connolly et al (Plant Physiology 133:1102-1110 (2003).*
Chun et al (Journal of Plant Physiology and Molecular Biology 2005, 31 (3): 235-240.*
Kobayashi et al (PNAS 19150-19155, 2007, vol. 104, No. 48).*
Guo et al, PNAS 2004 (101)25,9205-9210.*
Office Action dated Apr. 5, 2011 for corresponding Australian Patent Application No. 2008246775.
International Search Report in parent PCT/JP2008/057918.
Kobayashi et al., "Expression of iron-acquisition-related genes in iron-deficient rice is co-ordinately induced by partially conserved iron-deficiency-responsive elements", J. Exp. Bot., vol. 56, No. 415, pp. 1305-1316 (2005).
Kobayashi et al., "Identification of novel *cis*-acting elements, IDE1 and IDE2, of the barley IDS2 gene promoter conferring iron-deficiency-inducible, root-specific expression in heterogenous tobacco plants", Plant J., vol. 36, No. 6, pp. 780-793 (2003).
Kobayashi et al., "The transcription factor IDEF1 regulates the response to and tolerance of iron deficiency in plants", Proc. Natl. Acad. Sci., vol. 104, No. 48, pp. 1915019155 (Nov. 27, 2007).
DDBJ accession No. AK107456 (http://www.ddbj.nig.ac.jp/index-e.html).
DBBJ accession No. AK099540 (http://www.ddbj.nig.ac.jp/index-e.html).
Ogo et al., "Isolation and characterization of IRO2, a novel iron-regulated bHLH transcription factor in graminaceous plants", J. Exp. Bot., vol. 57, No. 11, pp. 2867-2878 (2006).
Colangelo et al., "The Essential Basic Helix-Loop-Helix Protein FIT1 Is Required for the Iron Deficiency Response," Plant Cell, vol. 16, No. 12, pp. 3400-3412 (Dec. 2004).
Ogo et al., "Iron Deficiency Inducible bHLH Transcription Factor OsIRO2 Controlling Genes Related to Iron Uptake", Abstracts of the Annual Meeting, Japanese Society of Soil Science and Plant Nutrition, vol. 52 (Sep. 2006).
Oryza sativa Japonica Group 0s05g0426200(0s05g0426200) mRNA, complete cds, NCBI Reference Sequence NM_001062135.1, vl, Oct. 3, 2006.
Australian Examination Report for Application No. 2011226969 dated Nov. 21, 2011.
Office Action dated Oct. 12, 2011 for corresponding Australian Patent Application No. 2008246775.

* cited by examiner

*Primary Examiner* — Anne Grunberg
*Assistant Examiner* — Lee Visone
(74) *Attorney, Agent, or Firm* — Harness, Dickey & Pierce, P.L.C.

(57) ABSTRACT

The present invention provides a polypeptide which binds to a cis-element in the vicinity of a gene related to an iron-acquisition mechanism. The polypeptide can increase expression of the gene related to the iron-acquiring mechanism. This makes it possible to obtain a plant improved in tolerance to iron deficiency.

2 Claims, 17 Drawing Sheets

FIG. 1

| | | |
|---|---|---|
| IDE1 | ATCAAGCATGCTTCTTGC | (SEQ ID:69) |
| OsNAAT1 (-290/-273) | AGCATGCATGGATCATGC | (SEQ ID:70) |
| OsNAS2 (-216/-199) | TCCATGCATGCATAATGC | (SEQ ID:71) |
| IDE1m1 | CGACCTACGGCTTCTTGC | (SEQ ID:72) |
| IDE1m11 | CGAAAGCATGCTTCTTGC | (SEQ ID:73) |
| IDE1m12 | ATCCCTCATGCTTCTTGC | (SEQ ID:74) |
| IDE1m13 | ATCAAGACGGCTTCTTGC | (SEQ ID:75) |
| IDE1m2 | ATCAAGCATTAGGAGGTA | (SEQ ID:76) |
| IDE1m21 | ATCAAGCATTAGTCTTGC | (SEQ ID:77) |
| IDE1m22 | ATCAAGCATGCTGAGTGC | (SEQ ID:78) |
| IDE1m23 | ATCAAGCATGCTTCTGTA | (SEQ ID:79) |
| IDE1m65 | CGACCTCATGCTTAGGTA | (SEQ ID:80) |
| IDE1m67 | CGACCTCATGCGGAGGTA | (SEQ ID:81) |

| | | |
|---|---|---|
| IDE2 | TTGAACGGCAAGTTTCACGCTGTCACT | (SEQ ID:93) |
| IDE2-m1 | GGTAACGGCAAGTTTCACGCTGTCACT | (SEQ ID:94) |
| IDE2-m2 | TTGCCAGGCAAGTTTCACGCTGTCACT | (SEQ ID:95) |
| IDE2-m3 | TTAACTTAAAGTTTCACGCTGTCACT | (SEQ ID:96) |
| IDE2-m4 | TTGAACGGCCCTTTTCACGCTGTCACT | (SEQ ID:97) |
| IDE2-m5 | TTGAACGGCAAGGGCACGCTGTCACT | (SEQ ID:98) |
| IDE2-m6 | TTGAACGGCAAGTTTACAGCTGTCACT | (SEQ ID:99) |
| IDE2-m7 | TTGAACGGCAAGTTTCACTAGGTCACT | (SEQ ID:100) |
| IDE2-m8 | TTGAACGGCAAGTTTCACGCTTGAACT | (SEQ ID:101) |
| IDE2-m9 | TTGAACGGCAAGTTTCACGCTGTCCAG | (SEQ ID:102) |
| IDE2-m31 | TTGAACTGCAAGTTTCACGCTGTCACT | (SEQ ID:103) |
| IDE2-m32 | TTGAACGTCAAGTTTCACGCTGTCACT | (SEQ ID:104) |
| IDE2-m33 | TTGAACGGAAAGTTTCACGCTGTCACT | (SEQ ID:105) |
| IDE2-m41 | TTGAACGGCCAGTTTCACGCTGTCACT | (SEQ ID:106) |
| IDE2-m42 | TTGAACGGCACGTTTCACGCTGTCACT | (SEQ ID:107) |
| IDE2-m43 | TTGAACGGCAATTTTCACGCTGTCACT | (SEQ ID:108) |
| IDE2-m51 | TTGAACGGCAAGGTTCACGCTGTCACT | (SEQ ID:109) |
| IDE2-m52 | TTGAACGGCAAGTGTCACGCTGTCACT | (SEQ ID:110) |
| IDE2-m53 | TTGAACGGCAAGTTGCACGCTGTCACT | (SEQ ID:111) |
| IDE2-m42G | TTGAACGGCAGGTTTCACGCTGTCACT | (SEQ ID:112) |

(b)

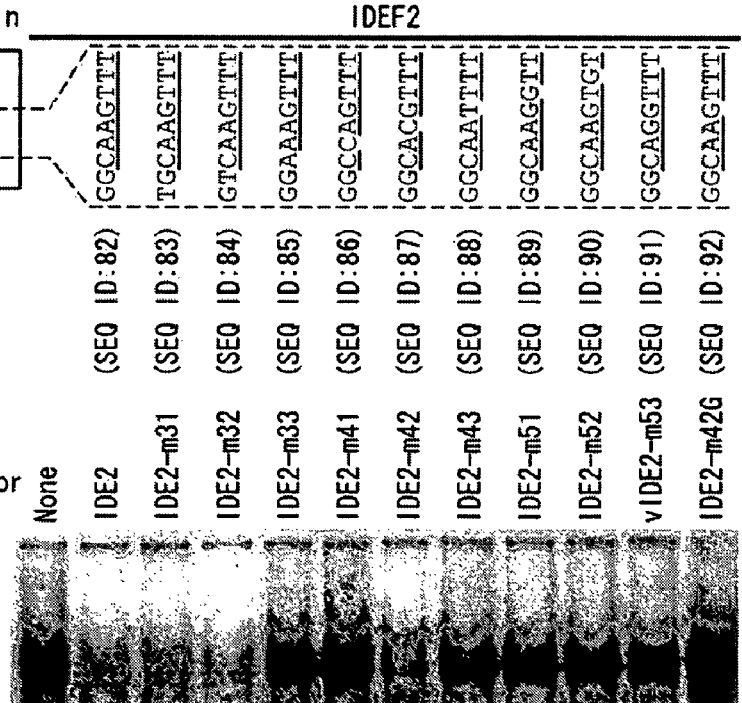
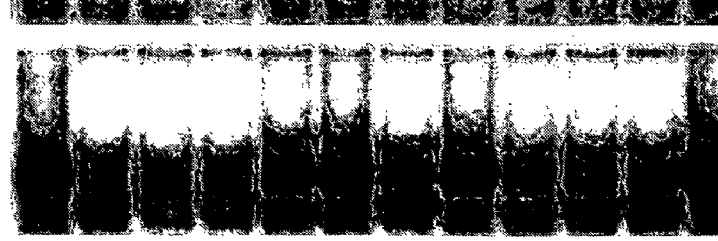

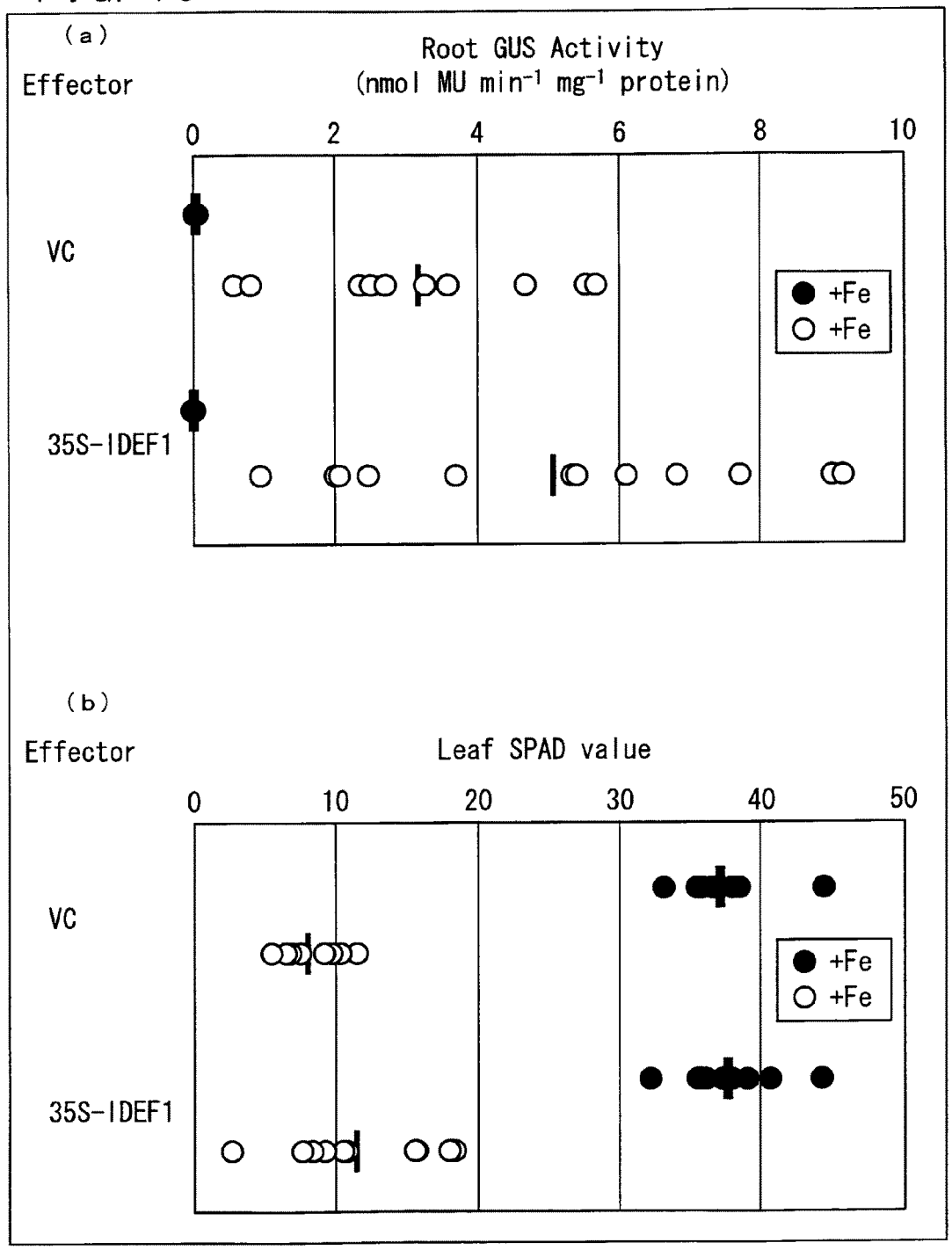

FIG. 14
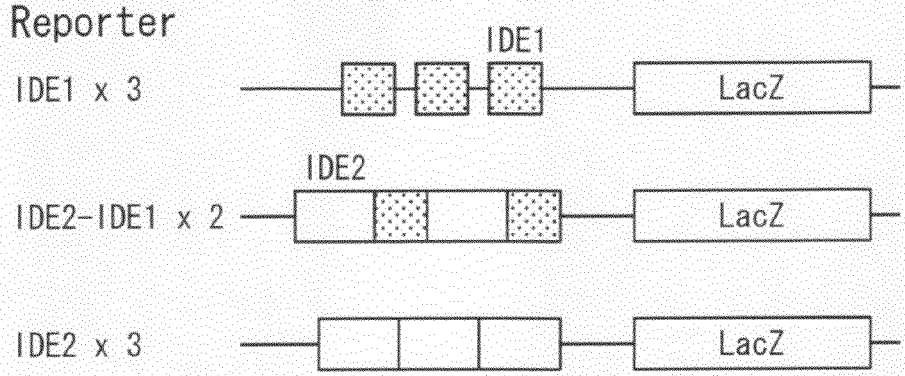
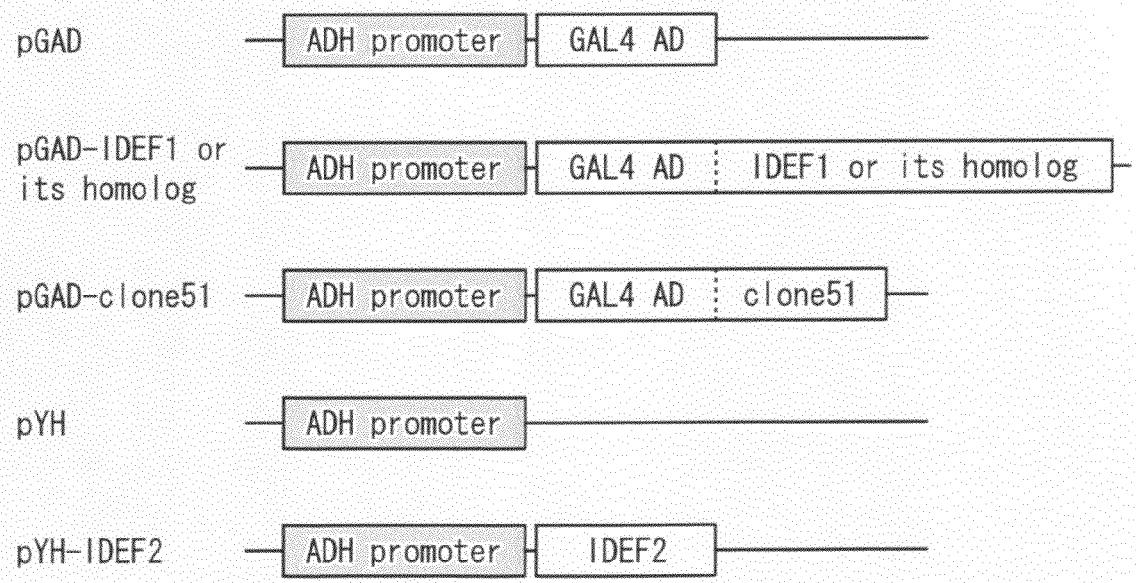

F I G. 1 8

```
                          10          20          30          40          50          60
(SEQ ID:113) IDEF1     LLNSGEYQVI  LRKELTKSDV  GNVGRIVLPK  KDAEASLPPL  LQRDPLILHM  DDMVLPVTWK
(SEQ ID:10)  Barley1   KFNSGEYQVI  LRKELTKSDV  ANVGRIVLPK  KDAEASLPPL  CERDPVILQM  DDMVLPVTWK
(SEQ ID:13)  Wheat     KFNSGEYQVI  LRKELTKSDV  ANVGRIVLPK  KDAEASLPPL  CERDPVILQM  DDMVLPITWK
(SEQ ID:16)  Maize     KFNSGEYQVI  LRKELTKSDV  ANSGRIVLPK  KDAEAGLPPL  VQGDPLILQM  DDMVLPIIWK
(SEQ ID:19)  Sorghum   KFNSGEYQVI  LRKELTKSDV  ANSGRIVLPK  KDAEAGLPPL  VQGDPLILQM  DDMVLPIIWK
(SEQ ID:22)  Sugarcane KFNSGEYQVI  LRKELTKSDV  ANSGRIVLPK  KDAEAGLPPL  VQGDPLILQM  DDMVLPIIWK
(SEQ ID:25)  Barley2   RFNCKDYYMI  VWKELTNSDV  GNIGRIVLPK  RDAEANLPAL  LERDGLILKM  DDLKLPVTWN
(SEQ ID:28)  AK072874  RFNCREYRVI  LRKELTNSDV  GNIGRIVMPK  RDAEAHLPAL  HQREGVMLKM  DDFKLETTWN
(SEQ ID:114) OsVP1     AKTDKNLRFL  LQKVLKQSDV  GSLGRIVLP-  KEAEVHLPEL  KTRDGVSIPM  EDIGTSQVWN
(SEQ ID:115) VP1       AKADKNLRFL  LQKVLKQSDV  GSLGRIVLPK  KEAEVHLPEL  KTRDGISIPM  EDIGTSRVWN 70          80          90         100         110
             IDEF      FKYRYWPNNK  SRMYILDSAG  EFLKTHGLQA  GDVIIIYKNL  APGKFIIRGE  KAI
             Barley1   FKYRFWPNNK  SRMYILDSTS  EFVKTHGLQA  GDALIIYKNP  VPGKYIVRGE  KAI
             Wheat     FKYRFWPNNK  SRMYILDSTS  EFVKTHGLQA  GDALIIYKNP  VPGKYIVRGE  KAI
             Maize     FKYRFWPNNK  SRMYILEAAG  EFVKTHGLQA  GDALIIYKNS  VPGKFIIRGE  KSI
             Sorghum   FKYRFWPNNK  SRMYILEAAG  EFVKTHGLQA  GDALIIYKNS  VPGKFIIRGE  KSI
             Sugarcane FKYRFWPNNK  SRMYILEAAG  EFVKTHGLXA  GDALIIYKNS  EPGKFIIRGE  KSI
             Barley2   FKFRFWPNNK  SRMYVLESTG  EFSKNHNLEP  QDTFIIYKSL  ESGKFLVRAE  KVT
             AK072874  FKYRFWPNNK  SRMYVLESTG  GFVKQHGLQT  GDIFIIYKSS  ESEKLVVRGE  KAI
             OsVP1     MRYRFWPNNK  SRMYLLENTG  DFVRSNELQE  GDFIVIYSDI  KSGKYLIRGV  KVR
             VP1       MRYRFWPNNK  SRMYLLENTG  EFVRSNELQE  GDFIVIYSDV  KSGKYLIRGV  KVR
```

FIG. 19

|              |         | 10         | 20         | 30         | 40         | 50         | 60         |
|--------------|---------|------------|------------|------------|------------|------------|------------|
| (SEQ ID:116) | IDEF2   | MAQTVLPPGF | RFHPTDVELV | SYYLKRKIMG | KKPLIQAISD | VELYKFAPWD | LPAQSCLQSR |
| (SEQ ID:117) | HvIDEF2 | MAQTVLPPGF | RFHPTDVELV | SYYLKRKIMG | KKLFVQAISE | VELYKFAPWD | LPDKSCLQSK |

|         | 70         | 80         | 90         | 100        | 110        | 120        |
|---------|------------|------------|------------|------------|------------|------------|
| IDEF2   | DLEWFFFCPR | DKKYPNGSRT | NESTPNGYWK | TSGKDRTIEL | NSRIVGSKKT | LIFHEGKAPK |
| HvIDEF2 | DLEWFFFCPR | DKKYPKGSRT | NEATPNGYWK | TSGKDRTIEL | NSRIVGLKKT | LIFHEGKAPK |

|         | 130        | 140        | 150        | 160        | 170        | 180        |
|---------|------------|------------|------------|------------|------------|------------|
| IDEF2   | GNRTDWVMYE | YKMEDNQLVS | AGFSKDDFVL | CKIFKKSGLG | PRIGEQYGAP | FNEEEWEHAD |
| HvIDEF2 | GNRTDWVMYE | YKMEDETLDA | AGFSKDAYVL | CKIFKKSGLG | PRIGEQYGAP | FDENEWENLD |

|         | 190        | 200        | 210        | 220        | 230        | 240        |
|---------|------------|------------|------------|------------|------------|------------|
| IDEF2   | AEMFPLLPNV | ETSVFPLLPS | SEVVNSTDDT | RVQPSVAARA | IEELPVQHLP | HVCAGNGSTY |
| HvIDEF2 | ---------V | CSSIFSFAPS | S-----GVEDP | QVESSALATA | VIQEP----- | ---------- |

|         | 250        | 260        | 270        | 280        | 290        | 300        |
|---------|------------|------------|------------|------------|------------|------------|
| IDEF2   | QNITVTGESA | LMELPSQHSV | ESIGDEVVSV | DNCSNVVNNA | DSPVIEGLVL | EELSRFLTDS |
| HvIDEF2 | ---------- | --FAPQQSV  | QFS---EHV  | NICSNEDNNA | P-PEIDGIWL | EELAMFLNDS |

|         | 310        | 320        | 330        | 340        | 350        | 360        |
|---------|------------|------------|------------|------------|------------|------------|
| IDEF2   | PHHGNPVGEH | SGLPPMSEAE | AHAFEVSTND | LYNEIAGLAE | LGVPNGDGFS | PSNAGVTEQ- |
| HvIDEF2 | PNHDIALPEN | SGLPPMSELE | AQAFEMNTAE | LYDQLAGLAQ | SGDMSNVNFP | AADVGVTEND |

|         | 370        | 380        | 390        | 400        | 410        | 420        |
|---------|------------|------------|------------|------------|------------|------------|
| IDEF2   | -QPTYFGVPN | SENYVNMDDI | FAPDTRLSYA | YP-------- | ---------- | LPNNQFWHYP |
| HvIDEF2 | FQQSNSGFAM | DDDYIELDDL | FAPGETFSYD | FSGETFSYDL | TGGTFSYDLS | VPNNQFLQYP |

|         | 430        | 440        | 450        | 460        | 470        | 480        |
|---------|------------|------------|------------|------------|------------|------------|
| IDEF2   | MDQFTYSTTL | S-----AAFP | SGDSRPTMR- | IVDDLPAAAN | N--GGFASKP | SMQFPLS... |
| HvIDEF2 | LDQSTNGSHY | GDGATQSTFE | ASGSLPPMPS | TFDDMPSVSN | KPANSNCLNP | TMEDPFS... |

A METHOD OF CREATING A PLANT IMPROVED IN TOLERANCE TO IRON DEFICIENCY

This application is a U.S. national stage filing under 35 U.S.C. §371 of International Application No. PCT/JP2008/057918 filed on 24 Apr. 2008, which claims priority to JP 2007-117725 filed on 26 Apr. 2007. The applications identified in this paragraph are incorporated by referenced in their entirety.

The material in the ASCII text file entitled A181-21US_SequenceListing.txt is hereby incorporated by reference in its entirety. The ASCII text file entitled A181-21US_SequenceListing.txt was created on 16 Feb. 2012 and the size is 75 KB.

TECHNICAL FIELD

The present invention relates to tolerance to iron deficiency in plants, particularly, to a polypeptide having a function of improving plants in tolerance to the iron deficiency.

BACKGROUND ART

Most living organisms require iron for their growth and reproduction. Plants take in solubilized iron existing in soils, thereby constituting a major iron inflow into animals and humans. Although mineral iron is abundant in soils, such iron is sparingly soluble under aerobic conditions at high pH. Consequently, in alkali soils which account for about 30% of the world's cultivated soils, plants often exhibit iron deficiency symptoms called "chlorosis" (yellowing from chlorophyll imperfection), reducing crop yield and quality. Accordingly, plants exhibiting high tolerance to the iron deficiency have been strongly desired.

In order to take in iron, higher plants employ iron-uptake strategies under iron-deficient conditions, that is, chelation (Strategy II) and reduction (Strategy I). Among these, Strategy II is specific to graminaceous plants. Strategy II is such that (i) iron in soils is chelated by use of the muginetic acid family phytosiderophores (MAs) which are natural iron chelators, and (ii) the iron thus chelated is taken into cells via transporters (YS1) existing in cell membranes of cells in roots.

To date, extensive physiological, biochemical and molecular studies identified a biosynthetic pathway of MAs and genes encoding biosynthetic enzymes (such as nicotianamine synthase (NAS), nicotianamine aminotransferase (NAAT), IDS2, and IDS3). There has been known that expression of these biosynthetic enzymes is coordinately increased in response to iron deficiency.

However, molecular mechanisms for increasing the expression of genes related to the response to the iron deficiency, that is, genes related to iron uptake under the iron-deficient conditions, are poorly understood. The inventors of the present invention analyzed a promoter region of a barley IDS2 gene which is induced to express under the iron-deficient conditions, thereby identifying novel iron-deficiency-responsive cis-elements IDE1 (Fe deficiency responsive element 1) and IDE2 (Fe deficiency responsive element 2), which synergistically induce, in tobacco roots as well as in rice roots and leaves, expression of the genes related to the response to the iron deficiency (Patent Literature 1).

CITATION LIST

Patent Literature 1

Japanese Patent Application Publication, Tokukai, No. 2005-6599 A (Publication Date: Jan. 13, 2005)

SUMMARY OF INVENTION

In the opinion of the inventors of the present invention, expression of the genes related to iron uptake in plants can be increased by use of a transcription factor binding to any one of the cis-elements, so that it becomes possible to obtain plants improved in tolerance to iron deficiency.

However, the transcription factors binding to the cis-elements have not been identified. Therefore, it has been impossible to use the transcription factors.

An object of the present invention is to provide a transcription factor binding to any one of the cis-elements, which transcription factor improves a plant in tolerance to iron deficiency.

As a result of diligent study, the inventors of the present invention identified polypeptides binding to the cis-elements, and found that the polypeptides improve plants in tolerance to iron-deficiency. Based on the finding, the inventors of the present invention accomplished the present invention.

That is, a polypeptide of the present invention improves a plant in tolerance to iron deficiency, the polypeptide including one of the following amino-acid sequences (A) through (C):

(A) the amino-acid sequence shown in SEQ ID NO: 1, 4, or 7;

(B) an amino-acid sequence in which one or several amino acids are substituted, added, or deleted in the amino-acid sequence shown in SEQ ID NO: 1, 4, or 7; and (C) an amino-acid sequence in which the 243rd-355th amino acids of the amino-acid sequence shown in SEQ ID NO: 1 are substituted by the amino-acid sequence shown in SEQ ID NO: 10, 13, 16, 19, 22, 25, or 28.

A polynucleotide of the present invention encodes the polypeptide of the present invention.

A polynucleotide of the present invention encodes a polypeptide which improves a plant in tolerance to iron deficiency, the polynucleotide including one of the following base sequences (A) through (D):

(A) the base sequence shown in SEQ ID NO: 2, 5, or 8;

(B) a base sequence in which one or several nucleotides are substituted, added, or deleted in the base sequence shown in SEQ ID NO: 2, 5, or 8;

(C) a base sequence hybridizable with a complementary sequence of the base sequence shown in SEQ ID NO: 2, 5, or 8, under stringent conditions; and (D) a base sequence in which the 727th-1065th bases of the base sequence shown in SEQ ID NO: 2 are substituted by the base sequence shown in SEQ ID NO: 11, 14, 17, 20, 23, 26, or 29.

A vector of the present invention includes the polynucleotide of the present invention.

A transformant of the present invention is the one into which the polynucleotide of the present invention is introduced.

An antibody of the present invention is specifically bindable to the polypeptide of the present invention.

A method of the present invention, for creating a plant improved in tolerance to iron deficiency, includes the step of introducing the polynucleotide of the present invention into a plant.

A composition of the present invention, for creating a plant improved in tolerance to iron deficiency, includes the polynucleotide or the vector of the present invention.

A kit of the present invention, for creating a plant improved in tolerance to iron deficiency, includes the polynucleotide or the vector of the present invention.

A method of the present invention, for breeding a plant improved in tolerance to iron deficiency, includes the step of detecting the polypeptide of the present invention, the polypeptide included in an extract from a plant.

The method of the present invention, for breeding a plant improved in tolerance to iron deficiency, may include the step of incubating an extract from a plant with the antibody of the present invention.

A composition of the present invention, for breeding a plant improved in tolerance to iron deficiency, preferably includes the antibody of the present invention.

A kit of the present invention, for breeding a plant improved in tolerance to iron deficiency, preferably includes the antibody of the present invention.

The method of the present invention, for breeding a plant improved in tolerance to iron deficiency, may include the step of detecting a polynucleotide in an extract of a plant, the polynucleotide being the polynucleotide of the present invention, or including the base sequence shown in SEQ ID NO: 12, 15, 18, 21, 24, or 27.

The method of the present invention, for breeding a plant improved in tolerance to iron deficiency, may include the step of incubating an extract from a plant with the polynucleotide of the present invention, or a polynucleotide including the base sequence shown in SEQ ID NO: 12, 15, 18, 21, 24, or 27.

The composition of the present invention, for breeding a plant improved in tolerance to iron deficiency, may include the polynucleotide of the present invention, or a polynucleotide including the base sequence shown in SEQ ID NO: 12, 15, 18, 21, 24, or 27.

The kit of the present invention, for breeding a plant improved in tolerance to iron deficiency, may include the polynucleotide of the present invention, or a polynucleotide including the base sequence shown in SEQ ID NO: 12, 15, 18, 21, 24, or 27.

A method of the present invention, for detecting a polynucleotide encoding a polypeptide which improves a plant in tolerance to iron deficiency, includes the step of hybridizing a candidate polypeptide with a polynucleotide including the base sequence shown in SEQ ID NO: 12, 15, 18, 21, 24, or 27.

Additional objects, features, and strengths of the present invention will be made clear by the description below. Further, the advantages of the present invention will be evident from the following explanation in reference to the drawings.

BRIEF DESCRIPTION OF DRAWINGS

FIG. 1 is a view showing an IDE1 sequence, IDE1-like sequences, and mutated IDE1 sequences.

FIG. 12 is a view explaining the competition experiments with regard to IDE2 ((a) of FIG. 12 shows sequences used in the competition experiments with regard to IDE2, and (b) of FIG. 12 shows a result of the accurate competition experiments with regard to IDE2).

FIG. 13 is a graph showing properties of tobacco transformed by a polynucleotide of the present invention ((a) of FIG. 13 is a graph showing GUS activity in roots of tobacco transformed by the polynucleotide of the present invention, and (b) of FIG. 13 shows chlorophyll content in leaves of tobacco transformed by the polynucleotide of the present invention).

FIG. 14 is a view illustrating a structure of each construct used in the yeast binding assay.

FIG. 18 is a view comparing an amino-acid sequence of IDEF1 with that of each of homologs of IDEF1.

FIG. 19 is a view comparing an amino-acid sequence of IDEF2 and that of each of homologs of IDEF2.

DESCRIPTION OF EMBODIMENTS

1: Polypeptide

Figure 2:
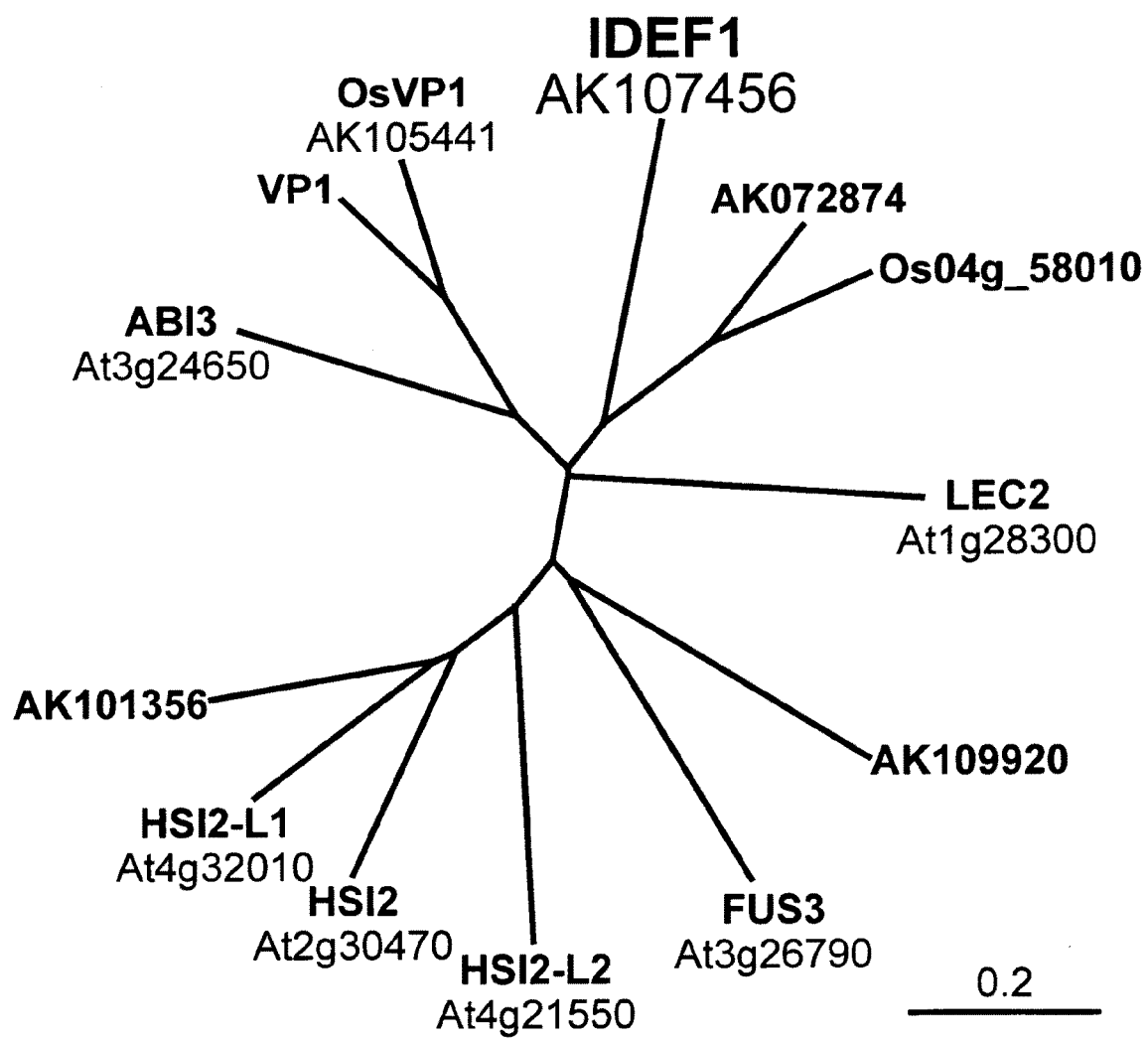
FIG. 2 is a view showing a phylogenic tree for ABI3/VP1 family transcription factors.

One aspect of the present invention provides a polypeptide which improves a plant in tolerance to iron deficiency. In the present specification, "tolerance of plants to iron deficiency" means a plant characteristic of being capable of growing in soil in which solubilized iron hardly exists, specifically, a characteristic of hardly causing chlorosis in growth in alkali soil or the like, for example. In order to determine whether or not a plant has such tolerance to iron deficiency, chlorophyll content in a leaf measured under iron-deficient conditions can be used as an index, for example (Chlorophyll content in a leaf may be indicated by an SPAD index). However, how to determine the tolerance is not limited to this.

In the present specification, the term "polypeptide" is exchangeable with the term "peptide" or "protein". Further, the term "fragment" of the polypeptide serves as a piece cut out from the polypeptide. The polypeptide of the present invention can be obtained from a natural supply source by isolation, or obtained through chemical synthesis.

The term "isolated" polypeptide (or protein) refers to a polypeptide (or protein) which is taken out of its natural environment. For example, a recombination-based polypeptide (protein) which has expressed in a host cell is considered as being isolated in the same manner as a natural or recombination-based polypeptide (protein) which is substantially purified by an appropriate technique arbitrarily.

The polypeptide of the present invention is preferably (i) a polypeptide including the amino-acid sequence shown in SEQ ID NO: 1, 4, or 7, or (ii) a mutant of the polypeptide.

In the present specification, the term "mutant" refers to a polypeptide having a specific activity of the target polypeptide, and the term "mutant of the polypeptide including the amino-acid sequence shown in SEQ ID NO: 1, 4, or 7" refers to a polypeptide having the activity which improves plants in tolerance to iron deficiency, in a case where the terms are used in relation to a protein or a polypeptide.

It is conventionally known in this field that several amino acids in an amino-acid sequence included in a polypeptide can be easily mutated without having a significant influence on a structure or a function of the polypeptide. Further, apart from the artificial mutation, it is also conventionally known that mutants occur for natural proteins without causing a significant structural or functional change.

A person skilled in the art can easily mutate one or several amino acids in the amino-acid sequence of the polypeptide by using a conventional technique. For example, according to a conventionally-known point mutation introducing method, it is possible to mutate an arbitral base of a polynucleotide encoding the polypeptide. Further, it is possible to produce a deletion mutant or an addition mutant by designing a primer corresponding to an arbitral site of the polynucleotide encoding the polypeptide.

It is preferable that the mutant is mutated by amino-acid conservative or non-conservative substitution, amino-acid deletion, or amino-acid addition. These mutations do not change the activity of the polypeptide of the present invention, which activity improves plants in tolerance to iron deficiency.

Further, it is also preferable that the mutant is such a chimeric polypeptide that a specific domain of the polypeptide of the present invention is substituted by a corresponding domain of a homolog of the polypeptide. It is highly probable that a homolog having high homology in amino acid sequence with respect to a specific polypeptide has a function identical with that of the specific polypeptide. For this reason, a person skilled in the art can easily understand that the mutant having the identical function can be easily obtained by substituting a specific domain of the polypeptide with the amino-acid sequence of such a homolog. The specific domain is preferably a domain with which the polypeptide binds to DNA. The specific domain may be, for example, the 243rd-355th amino acids in the amino-acid sequence shown in SEQ ID NO: 1. Further, the homolog preferably has homology of 50% or more, more preferably homology of 60% or more with respect to the amino-acid sequence of the domain. Examples of the homolog encompass a homolog of barley (Barley 1, Barley 2), a homolog of wheat (Wheat), a homolog of maize (Maize), a homolog of sorghum (Sorghum), a homolog of sugarcane (Sugarcane), and a homolog of rice (AK072874), each of which is shown in FIG. 18. Accordingly, the preferable chimeric polypeptide may be a polypeptide including an amino-acid sequence in which the 243rd-355th amino acids in the amino-acid sequence shown in SEQ ID NO: 1 are substituted by the amino-acid sequence shown in SEQ ID NO: 10, 13, 16, 19, 22, 25, or 28. The specific domain does not have to be substituted over its entire region, and may be substituted by the corresponding region of the homolog partially.

As described above, the polypeptide of the present embodiment has the activity which improves plants in tolerance to iron-deficiency, and is preferably (i) a polypeptide including the amino-acid sequence shown in SEQ ID NO: 1, 4, or 7, (ii) a polypeptide including an amino-sequence in which one or several amino acids are substituted, deleted, or added in the amino-acid sequence shown in SEQ ID NO: 1, 4, or 7, or (iii) a polypeptide including an amino-acid sequence in which the 243-355th amino acids in the amino-acid sequence shown in SEQ ID NO: 1 are substituted by the amino-acid sequence shown in SEQ ID NO: 10, 13, 16, 19, 22, 25, or 28.

The polypeptide of the present invention encompasses a product purified from a natural source, a product obtained through a chemical synthesis process, and a product produced from a prokaryotic host or an eukaryotic host (examples of such a host encompass bacterial cells, yeast cells, higher plant cells, insect cells, and mammalian cells) by a recombination technique. The polypeptide of the present invention may be glycosylated or non-glycosylated, depending on the host used in the recombination production process. Further, the polypeptide of the present invention may also encompass, in some cases, a modified initiation methionine residue, as a result of a host mediated process.

The polypeptide of the present invention is preferably a polypeptide having a peptide-bound amino acid. However, the polypeptide of the present invention is not limited to this, and may be a complex polypeptide containing a structure other than that of a polypeptide. In the present specification, the "structure other than that of a polypeptide" is not particularly limited, and may be a sugar chain or an isoprenoid group, for example.

Further, the polypeptide of the present invention may contain an additional polypeptide. Examples of the additional polypeptide encompass an epitope (H is, Myc, Flag, or the like)-tagged polypeptide.

The polypeptide of the present invention has the activity which improves plants in tolerance to iron deficiency because the polypeptide has an activity which increases expression of genes (iron-deficiency-inducible genes), which expression is induced in plants under iron-deficient conditions.

Examples of the iron-deficiency-inducible genes encompass OsNAAT1, OsNAS1, HvNAAT-A, and IDS3. Most proteins encoded by these genes are related to a mechanism (iron acquisition mechanism) for plants to take in non-solubilized iron existing in soil. For this reason, the activity of the polypeptide of the present invention increases the expression of the genes described above, thereby enabling plants to acquire a greater amount of iron, and grow in soil in which solubilized iron hardly exists.

Further, conversely, a person skilled in the art can easily understand that it is possible to determine whether or not an arbitral polypeptide has the activity which improves plants in tolerance to iron deficiency, by regarding the expression of the iron-deficiency-inducible genes as an index.

Furthermore, the polypeptide of the present invention has the activity which increases the expression of the iron-deficiency-inducible genes because the polypeptide (i) binds to a cis-element which exists in the upstream of most iron-deficiency-inducible genes in common, and (ii) functions as a transcription factor which increases the expression of genes flanking the cis-element.

Examples of the cis-element encompass the cis-element (IDE1) shown in SEQ ID NO: 30, and the cis-element (IDE2) shown in SEQ ID NO: 32 (see Patent Literature 1). Among the polypeptides of the present invention, the polypeptide (IDEF1: IDE binding factor 1) including the amino-acid sequence shown in SEQ ID NO: 1, and the mutant of IDEF1, bind to IDE1, and the polypeptide (IDEF2: IDE binding factor 2) including the amino-acid sequence shown in SEQ ID NO: 4 or 7, and the mutant of IDEF2, bind to IDE2.

It is more preferable that IDEF1 and a mutant of IDEF1 recognize the base sequence shown in SEQ ID NO: 31 as a core sequence, and IDEF2 and a mutant of IDEF2 recognize the base sequence shown in SEQ ID NO: 33 as a core sequence. In the present specification, the "core sequence" is a minimum unit of the base sequence to which the transcription factor binds. IDE1 and IDE2 include, respectively, the base sequence shown in SEQ ID NO: 31 and the base sequence shown in SEQ ID NO: 33, so that IDEF1 and a mutant of IDEF1 can bind to IDE1, and IDEF2 and a mutant of IDEF2 can bind to IDE2.

As described above, the polypeptide of the present invention functions as the transcription factor which binds to the cis-element which exists in the upstream of most iron-deficiency-inducible genes in common, thereby being capable of increasing the expression of the iron-deficiency-inducible genes.

Further, conversely, a person skilled in the art can easily understand that it is possible to determine whether or not an arbitral polypeptide has the activity which improves plants in tolerance to iron-deficiency, by determining whether or not the polypeptide can bind to any one of the cis-elements described above. In order to determine whether or not an arbitral polypeptide can bind to any one of the cis-elements described above, it is possible to use gel shift assay, as described in the following Examples. However, the determining method is not limited to this.

Furthermore, as described later, the polypeptide of the present invention specifically increases the expression of the iron-deficiency-inducible genes under iron-deficient conditions. That is, in plants, in response to iron deficiency, the polypeptide of the present invention controls the expression of the genes related to the response in the upstream of the genes.

IDE1 and IDE2 described above exist close to a promoter region of the iron-deficiency-inducible genes, and have a function of synergistically increasing the expression of the iron-deficiency-inducible genes (see Patent Literature 1).

Another aspect of the present invention provides a method of producing a polypeptide having an activity which improves plants in tolerance to iron deficiency.

In the method of producing the polypeptide, in accordance with one embodiment of the present invention, a vector containing a polynucleotide encoding the polypeptide is used.

In one aspect of the method of producing the polypeptide, in accordance with the present embodiment of the present invention, the vector is preferably used in a recombination expression system. In a case where the recombination expression system is employed, it is possible to adopt, for example, a method including the steps of (i) implanting, into the expression vector, the polynucleotide encoding the polypeptide of the present invention, and then (ii) by a conventionally-known method, introducing the expression vector into a host which can express the polypeptide, after that, (iii) purifying the polypeptide obtained through translation in the host. The recombination expression vector may or may not be a plasmid, and only has to be capable of introducing the target polynucleotide into the host. The method of the present embodiment, for producing the polypeptide, preferably includes the step of introducing the vector into the host.

In a case where a foreign polynucleotide is introduced into the host as described above, it is preferable that a promoter which has a function of inducing the foreign polynucleotide to express in the host is implanted into the expression vector in advance. A method of purifying the recombination-based polypeptide varies depending on characteristics of the host and polypeptide thus used. However, by use of the tag or the like, the target polypeptide can be purified with relative ease.

The method of the present embodiment, for producing the polypeptide, preferably includes the step of purifying the polypeptide from an extract from cells or tissues which contain the polypeptide. The step of purifying the polypeptide preferably includes the steps of (i) preparing a cell extract from cells or tissues by a known method (method of (1) breaking the cells or tissues, and then (2) causing the cells or tissues thus broken to be subjected to centrifugal separation, and (3) collecting the resultant soluble fractions, for example), and (ii) purifying the polypeptide from the cell extract by a known method (such as an ammonium sulfate precipitation method, an ethanol precipitation method, an acid extraction method, cation-exchange/anion-exchange chromatography, phosphocellulose chromatography, hydrophobic interaction chromatography, affinity chromatography, hydroxyapatite chromatography, or lectin chromatography). However, the step of purifying the polypeptide is not limited to this. The most preferable method for purifying the polypeptide is high-performance liquid chromatography (HPLC).

In another aspect of the method of producing the polypeptide, in accordance with the present embodiment of the present invention, the vector is preferably used in a cell-free protein synthesis system. In a case where the cell-free protein synthesis system is employed, various commercially-available kits can be used. Preferably, the method of the present embodiment, for producing the polypeptide, includes the step of incubating the vector and a cell-free protein synthesis solution.

The cell-free protein synthesis system is a technique widely used to, for example, identify various proteins encoded by intracellular mRNA or cloned cDNA. The cell-free protein synthesis solution is used in the cell-free protein synthesis system (also called "cell-free protein synthesis method" or "cell-free protein translation method").

Examples of the cell-free protein synthesis system encompass a system employing a wheat germ extract, a system employing a rabbit reticulocyte extract, a system employing an *Escherichia coli* S30 extract, and a cellular component extract obtained from evacuolate protoplasts of plants. Generally, for the translation of eukaryote-derived genes, an eukaryotic cellular system, that is, the system employing the wheat germ extract or the rabbit reticulocyte extract is selected. However, it is possible to select any one from among the systems described above, in consideration of derivation (prokaryote/eukaryote) of the genes to be translated and intended use of the protein obtained through the synthesis.

Various virus-derived gene products are mostly the ones in which, after the translation is carried out, the products are activated through complex biochemical reactions in which intracellular membranes, such as endoplasmic reticulums or Golgi bodies, are involved. Therefore, in order to replicate such various chemical reactions in a test tube, it is necessary to add intracellular membrane components (microsomal membranes, for example). It is preferable to use a cellular component extract obtained from evacuolate protoplasts of plants because the cellular component extract can be used as the cell-free protein synthesis solution which keeps the intracellular membrane components, and does not require the addition of the microsomal membranes.

In the present specification, the term "intracellular membrane components" refers to cell organelles (i.e. general intracellular granules, such as the endoplasmic reticulums, the Golgi bodies, mitochondria, chloroplasts, and vacuoles) constituted by lipid membranes existing in cellular cytoplasm. The endoplasmic reticulums and the Golgi bodies particularly play an important role for posttranslational modification with respect to proteins, and are cellular components necessary for maturation of membrane proteins and secretory proteins.

In another embodiment of the method of the present invention, for producing the polypeptide, the polypeptide is preferably purified from cells or tissues in which the polypeptide is naturally expressed. The method of the present embodiment, for producing the polypeptide, preferably includes the step of identifying, by use of an antibody or an oligonucleotide which are described later, the cells or tissues in which the polypeptide of the present invention is naturally expressed. Further, the method of the present embodiment, for producing the polypeptide, preferably further includes the step of purifying the polypeptide.

Furthermore, in the method of producing the polypeptide, in accordance with still another embodiment of the present invention, the polypeptide of the present invention is obtained through chemical synthesis. A person skilled in the art can easily understand that by adopting a known chemical synthesis technique based on the amino-acid sequence (described in the present specification) of the polypeptide of the present invention, the polypeptide of the present invention can be obtained through chemical synthesis.

As described above, the polypeptide obtained by the method of the present invention, for producing the polypeptide, may be a natural mutant polypeptide or an artificially-produced mutant polypeptide.

Thus, the method of the present invention, for producing the polypeptide, only has to use at least a conventionally-known technique based on the amino-acid sequence of the polypeptide or the base sequence of the polynucleotide encoding the polypeptide. In other words, it should be noted that the technical scope of the present invention encompasses a production method including steps other than the various steps described above.

2: Polynucleotide

One aspect of the present invention provides genes encoding a polypeptide having an activity which improves plants in tolerance to iron deficiency.

In the present specification, the term "polynucleotide" is exchangeable with the term "genes", "nucleic acid", or "nucleic acid molecules", and serves as a polymer of a nucleotide. In the present specification, the term "base sequence" is exchangeable with the term "nucleic-acid sequence" or "nucleotide sequence", and serves as a sequence of a deoxyribonucleotide (referred to as A, G, C, and T).

The polynucleotide of the present invention is preferably a polynucleotide encoding the polypeptide of the present invention. In a case where an amino-acid sequence of a specific polypeptide is obtained, it is possible to easily design the base sequence of the polynucleotide encoding the polypeptide.

The polynucleotide of the present invention is preferably (i) a polynucleotide including the base sequence shown in SEQ ID NO: 2, 5, or 8, or (ii) a mutant of the polynucleotide.

In the present specification, the term "mutant" refers to the polynucleotide encoding the polypeptide having the same activity as that of the specific polypeptide, and the term "the mutant of the polynucleotide including the base sequence shown in SEQ ID NO: 2, 5, or 8" refers to the polynucleotide encoding the polypeptide having the activity which improves a plant in tolerance to iron deficiency, in a case where the terms are used in relation to the polynucleotide. That is, in the present specification, in view of the polynucleotide, the mutant is the polynucleotide encoding the polypeptide having the activity which improves a plant in tolerance to iron deficiency, and can be (i) a polynucleotide including the base sequence in which one or several bases are substituted, deleted, or added in the base sequence shown in SEQ ID NO 2, 5, or 8, (ii) a polynucleotide hybridizable with, under stringent conditions, a complementary sequence of the base sequences shown in SEQ ID NO: 2, 5, or 8, or (iii) a polynucleotide including a base sequence in which the 727th-1063rd bases in the base sequence shown in SEQ ID NO: 2 are substituted by the base sequence shown in SEQ ID NO: 11, 14, 17, 20, 23, 26, or 29.

The polynucleotide including a base sequence in which the 727th-1063rd bases in the base sequence shown in SEQ ID NO: 2 are substituted by the base sequence shown in SEQ ID NO: 11, 14, 17, 20, 23, 26 or 29, is a chimeric polynucleotide encoding a chimeric polypeptide including an amino-acid sequence in which the 243rd-355th amino-acids in the amino-acid sequence shown in SEQ ID NO: 1 are substituted by the amino-acid sequence shown in SEQ ID NO: 10, 13, 16, 19, 22, 25, or 28. With the present specification, a person skilled in the art can easily understand that the chimeric polynucleotide can be easily obtained by use of a conventionally-known technique.

The polynucleotide of the present invention can be in the form of RNA (mRNA, for example), or in the form of DNA (cDNA or genomic DNA, for example). The DNA may be single-strand DNA or double-strand DNA. The single-strand DNA, or single-strand RNA may be a coding strand (also known as "sense strand"), or a non-coding strand (also known as "anti-sense strand").

In the present specification, the term "oligonucleotide" serves as the one in which several or tens of nucleotides are integrated, and is exchangeable with the term "polynucleotide". A short oligonucleotide is called "dinucleotide (dimmer)", or "trinucleotide (trimmer)", and a long oligonucleotide is expressed in the number of the nucleotides that are polymerized with each other, like "30 mer" or "100 mer". The oligonucleotide may be produced as a fragment of a longer polynucleotide, or produced through chemical synthesis.

Further, the polynucleotide of the present invention can be fused to, on its 5' side or 3' side, a polynucleotide encoding the tags (tag sequence or marker sequence) described above.

Hybridization can be carried out by a known method such as a method disclosed in "Sambrook et al., Molecular Cloning, A Laboratory Manual, 2nd Ed., Cold Spring Harbor Laboratory (1989)". Generally, as the temperature becomes higher and/or a salt concentration becomes lower, stringency becomes higher (it becomes harder to carry out the hybridization), so that it becomes possible to obtain a more homologous polynucleotide. An appropriate temperature for the hybridization varies depending on the base sequence or a length of the base sequence. For example, if a DNA fragment including 18 bases encoding 6 amino acids is used as a probe, the temperature of 50° C. or less would be preferable.

In the present specification, the term "stringent hybridization conditions" means that (i) incubation is carried out for one night at a temperature of 42° C. in a hybridization solution (which includes a 50% formamide, 5×SSC (a 150 mM NaCl, a 15 mM trisodium citrate), a 50 mM sodium phosphate (pH 7.6), a 5×Denhardt's solution, a 10% dextran sulfate, and a 20 µg/ml altered shear salmon sperm DNA), and then (ii) a filter is washed in a 0.1×SSC at a temperature of 65° C. The polynucleotide which hybridizes with "a part" of a polynucleotide refers to a polynucleotide (DNA or RNA) which hybridizes with a polynucleotide that is longer than a reference polynucleotide by at least approximately 15 nucleotides (nt), preferably by approximately 20 nt, more preferably by approximately 30 nt, still more preferably by longer than approximately 30 nt. The polynucleotide (oligonucleotide) which hybridizes with "a part" of the polynucleotide as described above is also useful as a detection probe which is explained below in detail in the present specification.

As described above, the polynucleotide of the present invention is the polynucleotide encoding the polypeptide having the activity which improves plants in tolerance to iron deficiency, and is preferably one of the followings: (1) the polynucleotide including the base sequence shown in SEQ ID NO: 2, 5, or 8; (2) the polynucleotide including a base sequence in which one or several bases are substituted, deleted, or added in the base sequence shown in SEQ ID NO: 2, 5, or 8; (3) the polynucleotide hybridizable with, under the stringent conditions, the polynucleotide including the complementary sequence of a base sequence in which one or several bases are substituted, deleted, or added in the base sequence shown in SEQ ID NO: 2, 5, or 8, and (4) the polynucleotide including a base sequence in which the 727th-1063rd bases in the base sequence shown in SEQ ID NO: 2 are substituted by the base sequence shown in SEQ ID NO: 11, 14, 17, 20, 23, 26, or 29.

The polynucleotide of the present invention may contain a sequence of an untranslated region (UTR), a vector sequence (which includes an expression vector sequence), or the like.

A supply source for obtaining the polynucleotide of the present invention is preferably, but not particularly limited to, a biological material. In the present specification, the term "biological material" refers to a biological sample (a tissue sample or cell sample which is obtained from an organism). Graminaceous plants were used as the biological material in the following Examples, however, the present invention is not limited to these.

3: Vector

The present invention provides a vector containing a polynucleotide encoding a polypeptide having an activity which improves a plant in tolerance to iron deficiency. The vector of the present invention can be produced by introducing the polynucleotide of the present invention into a predetermined vector by a conventionally-known gene recombination technique. Other than a recombination expression vector, a cloning vector can be also used as the vector described above. However, the vector is not limited to these. The vector of the present invention can be used to produce either the polypeptide of the present invention, or a transformant of the present invention.

4: Transformant

The present invention provides a method of newly creating a plant improved in tolerance to iron deficiency. The term "method of newly creating a plant improved in tolerance to iron deficiency" serves as a method of producing a plant body improved in tolerance to iron deficiency. The method of the present invention, for newly creating a plant improved in tolerance to iron deficiency, only has to include the step of introducing the polynucleotide of the present invention into a plant body. The method of newly creating a plant improved in tolerance to iron deficiency, in accordance with one embodiment of the present invention, includes the step of hybridizing a plant body in which the polynucleotide of the present invention has not expressed, with another plant body in which the polynucleotide of the present invention has expressed. This method is preferable for producing a non-transformed plant body.

The method of newly creating a plant improved in tolerance to iron deficiency, in accordance with another embodiment of the present invention, includes the step of introducing a recombination vector containing the polynucleotide of the present invention, into a plant so as to allow a polypeptide encoded by the polynucleotide of the present invention to express. The plant body improved in tolerance to iron deficiency by the method of the present embodiment can be a plant transformant.

In a case where the recombination expression vector is employed, the vector used to transform a plant body is not particularly limited as long as it is capable of causing the polynucleotide of the present invention to express in the plant. Examples of such a vector encompass: a vector having a promoter (35S promoter of a cauliflower mosaic virus, for example) which causes the polynucleotide to constitutively express in a plant cell; and a vector having a promoter inductively activated by external stimuli. As described later, it is more preferable to use the promoter which is activated in response to the iron deficiency than the promoter which is constitutively activated. The promoter activated in response to the iron deficiency may be, for example, an IDS2 promoter (see sequence number 68, Kobayashi, T. et al., Construction of Artificial Promoters Highly Responsive to Iron Deficiency, Soil Sci, Plant Nutr. 50, 1167-1175 (2004)).

In the present invention, a target plant to be transformed may be any one of the followings: an entire plant; plant organs (leaves, petals, stems, roots, seeds, and the like); plant tissues (epidermises, phloems, parenchymas, xylems, vascular bundles, palisade tissues, cancellous tissues, and the like); plant culture cells; plant cells in various forms (suspension-cultured cells, for example); protoplasts; leaf disks; and calli. The plant to be transformed is preferably, but not limited to, a graminaceous plant, more preferably, rice, barley, wheat, or maize.

The introduction of the gene into a plant is carried out by a transformation method which has been conventionally known by a person skilled in the art. Examples of the transformation method encompass an *agrobacterium* method, a gene gun method, a PEG method, and an electroporation method. These methods are roughly classified into *agrobacterium* methods in which the gene is introduced via *agrobacteria*, and direct introduction methods in which the gene is introduced directly into a plant cell. By the *agrobacterium* methods, the plant transformant can be obtained in such a manner that (i) a plant expression vector thus produced is introduced into an appropriate *agrobacterium* (*agrobacterium tumefaciens*, for example), and (ii) an aseptic culture leaf disk is caused to be infected with a strain of the *agrobacterium* by a leaf disk method (Hirohumi UCHIMIYA, Plant Genetic Manipulation Manual (1990), pp 21-31, Kodansya Scientific Ltd., Tokyo), or the like. Further, alternatively, the *agrobacterium* methods may adopt a technique disclosed in Nagel et el. (Micribiol. Lett., No. 67,325 (1990)). According to this technique, first, the expression vector is introduced into an *agrobacterium*, for example, and then, the *agrobacterium* which has been transformed is introduced into a plant cell or a plant tissue by a method described in Plant Molecular Biology Manual (S. B. Gelvin et al., Academic Press Publishers). Here, the term "plant tissue" includes a callus obtained by the culture of the plant cell. In a case where the transformation is carried out by the *agrobacterium* method, a pBI binary vector (pBIG, pBIN19, pBI101, pBI121, pBI221, pPZP202, or the like) can be used.

Further, as direct introduction methods of introducing the gene directly into a plant cell or a plant tissue, an electroporation method and a gene gun method have been known. In the gene gun method, a plant body, a plant organ, or a plant tissue per se without any modification can be the target into which the gene is introduced. As alternatives, a segment cut out from or a protoplast prepared from such a plant body, a plant organ, or a plant tissue can be the target. A sample thus prepared can be processed by use of a gene introduction apparatus (PDS-1000 (BIO-RAD Laboratories Inc.), for example). Conditions for the process vary depending on the plant or the sample. Generally, however, the process is carried out by a pressure of approximately 450 psi to 2000 psi at a distance of approximately 4 cm to 12 cm.

The cell or plant tissue into which the gene is introduced is selected based on a chemical tolerance such as a hygromycin tolerance, and then regenerated into a plant body by any method known in the art. Depending on the sort of plant cells, a person skilled in the art can regenerate the plant body from the transformed cells by a conventionally-known method. A selection marker is not limited to the hygromycin tolerance, and may be a chemical tolerance with respect to: bleomycin; kanamycin; gentamycin; chloramphenicol; or the like, for example.

In a case where the plant culture cell is used as the host, the recombination vector is introduced into the culture cell by, for example, a microinjection method, the electroporation method, the polyethylene glycol method, the gene gun method (particle gun method), a protoplast fusion method, or a calcium phosphate method. Thereby, the plant culture cell is transformed. The calli, shoots, capillary roots or the like, obtained through the transformation, can be used for cell culture, organ culture, or tissue culture without any modification, and it is possible to regenerate a plant body by introducing, into any of them, a phytohormone (an auxin, a cytokinin, a gibberellin, an abscisic acid, ethylene, a brassinolide, or the like) having an appropriate concentration.

In order to determine whether or not the gene is successfully introduced into the plant, a PCR method, a southern hybridization method, a northern hybridization method, or the like, can be used. For example, DNA is prepared from the transformed plant, and a DNA specific primer is designed. Then, the PCR is carried out. The PCR can be carried out under the same conditions as the conditions for the preparation of the plasmid. After that, an amplified product thus obtained is subjected to agarose gel electrophoresis, polyacrylamide gel electrophoresis, or capillary electrophoresis, and then is stained with ethidium bromide, or SYBR Green. This allows the amplified product to be detected as one band, so that the transformation can be confirmed. Further, it is also possible to detect the amplified product by carrying out the PCR by use of a primer which has been labeled with a fluorescent dye or the like in advance. Furthermore, alternatively, it is possible to adopt a method of confirming the amplified product by a fluorescence reaction or an oxygen reaction by causing the amplified product to bind to a solid phase, such as a microplate.

Once such a transformed plant body that the polynucleotide of the present invention is implanted into a genome is obtained, offspring of the plant body can be obtained through sexual reproduction or asexual reproduction of the plant body. Further, it is possible to mass-produce the plant body based on seeds, fruits, spikes, stem tubers, root tubers, strains, calli, protoplasts or the like, obtained from the plant body, its offspring, or clones of these. Accordingly, the scope of the present invention encompasses: a plant body into which the polynucleotide of the present invention is introduced so as to express in the plant body; offspring of the plant body, which offspring has the same characteristics as the plant body; and tissues derived from these.

The present invention further provides a composition and kit for newly creating a plant improved in tolerance to iron deficiency. The composition of the present invention, for newly creating a plant improved in tolerance to iron deficiency, includes the polynucleotide or vector of the present invention. The kit of the present invention, for newly creating a plant improved in tolerance to iron deficiency, includes the polynucleotide or vector of the present invention. In the present specification, the term "composition" refers to such a form that various components are included in a single material, and the term "kit" refers to such a form that at least one of the various components are included in another material separately. Further, the "composition for newly creating a plant improved in tolerance to iron deficiency" refers to a composition used to produce a plant body improved in tolerance to iron deficiency. The "kit for newly creating a plant improved in tolerance to iron deficiency" refers to a kit used to produce a plant body improved in tolerance to iron deficiency.

The transformant of the present invention is such that the polynucleotide of the present invention is implanted into the genome, so that the polypeptide of the present invention can express and improve the tolerance to iron deficiency. As described above, by using the polynucleotide or vector of the present invention, it is possible to introduce the polynucleotide of the present invention into a plant body. Therefore, the composition including the polynucleotide or vector of the present invention, or the kit including the polynucleotide or vector of the present invention, can be suitably used to newly create a plant improved in tolerance to iron deficiency. That is, in one embodiment, the composition and kit of the present invention, for newly creating a plant improved in tolerance to iron deficiency, can be used as a supply source of the polynucleotide or vector of the present invention in the method of introducing the polynucleotide or vector into a plant body.

The composition of the present invention, for newly creating a plant improved in tolerance to iron deficiency, may include, in addition to the polynucleotide or vector of the present invention, a solvent, a dispersion medium, a reagent, and the like. Further, the kit of the present invention, for newly creating a plant improved in tolerance to iron deficiency, may include, in addition to the polynucleotide or vector of the present invention, a solvent, a dispersion medium, a reagent, instructions for the use of these, and the like. In the present specification, the term "include (including)" means a state where such inclusions are included in any one of containers (a bottle, a plate, a tube, a dish, and the like) constituting the kit, in a case where the term is used in relation to the kit. Further, the kit of the present invention can be a single package including a plurality of compositions that are different from each other. Here, the form of the composition may be as described above. In a case where the composition is in a liquid form, the composition may be included in a container. The kit of the present invention may be such that materials A and B are included in the same container in a mixed manner, or included in separate containers respectively. The "instructions" may be written or printed on paper or another medium, and can be stored in an electronic medium such as a magnetic tape, a computer-readable disc, a computer-readable tape, or a CD-ROM. The kit of the present invention can also include a container including a dilution agent, a solvent, a cleaning liquid, and/or another reagent is included.

5: Antibody

The present invention provides an antibody which specifically binds to a polypeptide having an activity which improves a plant in tolerance to iron deficiency. The antibody of the present invention is not particularly limited as long as it can specifically bind to the polypeptide. For example, the antibody may be a polyclonal antibody or a monoclonal antibody, with respect to the polypeptide. Among these, it is preferable to use the monoclonal antibody because it is advantageous in that (i) its characteristics are constant so that it is easy to supply the antibody, and (ii) it is possible to store the antibody semipermanently as a hybridoma, for example.

In the present specification, the term "antibody" refers to an immunoglobulin (IgA, IgD, IgE, IgG, IgM, Fab fragments of these, $F(ab')_2$ fragments of these, and Fc fragments of these). The antibody may be, but not limited to, the polyclonal antibody, the monoclonal antibody, a single-stranded antibody, or an anti-idiotypic antibody.

The "antibody" can be produced in accordance with conventionally-known various methods. For example, the monoclonal antibody can be easily produced by a technique which has been conventionally known in this field (for example, see: a hybridoma method (Kohler, G. and Milstein, C., Nature 256, 495-497 (1975)); a trioma method; a human B-cell hybridoma method (Kozbor, Immunology Today 4, 72 (1983)); and an EBV-hybridoma method (Monoclonal Antibodies and Cancer Therapy, Alan R Liss, Inc., 77-96 (1985)).

Further, a peptide antibody can be easily produced in accordance with a method which has been conventionally known in this field (for example, see: Chow, M. et al., Proc. Natl. Acad. Sci. U.S.A. 82:910-914; and Bittle, F. J. et al., J. Gen. Virol. 66:2347-2354 (1985) (which is incorporated by reference in the present specification)).

It is self-evident for a person skilled in the art that the Fab and $F(ab')_2$ fragments, and other fragments of the antibody of the present invention can be used in accordance with the method disclosed in the present specification. Typically, such fragments can be produced by cleavage by protein decomposition employing an enzyme such as papain (which produces the Fab fragments) or pepsin (which produces the $F(ab')_2$ fragments). Alternatively, the fragment which binds to the polypeptide of the present invention can be produced by application of a DNA technique or produced through chemical synthesis.

As described above, the antibody of the present embodiment only has to include the fragment (a Fab fragment or a $F(ab')_2$ fragment, for example) which binds to the polypeptide of the present invention. It should be noted that the scope of the present invention includes an immune globulin including an Fc fragment of a different antibody molecule.

That is, an object of the present invention is to provide the antibody which specifically binds to the polypeptide of the present invention, and the usage of the antibody, and is not to provide, as an invention, (i) a specific sort of immune globulin as specifically described above in the present specification (such as IgA, IgD, IgE, and IgM), or (ii) a specific method of producing the antibody. Therefore, it should be noted that other antibodies obtained through a method other than each of the methods described above are included in the scope of the present invention.

6: Breeding Method

The present invention provides a method of breeding a plant improved in tolerance to iron deficiency. The method of the present invention, for breeding a plant improved in tolerance to iron deficiency, only has to include the step of detecting the polypeptide of the present invention, which polypeptide has expressed in a plant body. In the method of the present invention, for breeding a plant, a plant having a tolerance to iron deficiency is selected based on the detection as to whether or not the polypeptide of the present invention is expressed.

As described above, the polypeptide of the present invention increases the expression of the genes which play an important role when a plant takes in iron from soil. Accordingly, the plant in which the polypeptide expresses is excellent in acquiring iron, and is improved in tolerance to iron deficiency. The plant body bred in accordance with the method of the present invention may be a natural plant body or a transformant.

In one embodiment of the present invention, the method of a breeding plant improved in tolerance to iron deficiency, includes the step of detecting the polypeptide of the present invention, which polypeptide is included in the extract from a plant.

The extract from the plant can be obtained by a freeze grinding method employing liquid nitrogen or by use of a commercially-available extraction kit. However, the method of obtaining the extract is not limited to these. Further, in the present specification, the "extract" may be a lowly-purified product, or a highly purified product that is obtained through several purification steps.

In one aspect, the step of detecting the polypeptide of the present invention, which polypeptide is included in the extract from the plant, the polypeptide of the present invention is detected by reacting the antibody of the present invention with the extract from the plant. As described above, the antibody forms an immune complex by specifically binding to the polypeptide of the present invention. For this reason, by detecting the formation of the immune complex, the polypeptide expressed in the plant body can be easily detected. For example, the formation of the complex can be detected by: isotopically labeling the antibody in advance; employing a second antibody with respect to the antibody; or the other detection technique. Specifically, the detection may be, but not limited to, a western blotting, a protein chip technique, or the like, each of which has been conventionally known.

Further, as described above, the antibody of the present invention can be suitably used in the method of the present invention, for breeding a plant improved in tolerance to iron deficiency. Accordingly, the composition including the antibody of the present invention, or the kit including the antibody of the present invention, can be suitably used to breed a plant improved in tolerance to iron deficiency.

In another embodiment of the present invention, the method of breeding a plant includes the step of detecting the polynucleotide of the present invention, which polynucleotide is included in the extract from a plant.

In one aspect, the step of detecting the polynucleotide of the present invention, which polynucleotide is included in the extract from the plant, includes the step of incubating the extract from the plant with an oligonucleotide including a fragment of the polynucleotide of the present invention or a complementary sequence of the polynucleotide. Preferably, the method of the present embodiment, for breeding a plant, includes the step of causing the extract from the plant to hybridize with cDNA with respect to target plant-derived genome DNA, mRNA, or mRNA.

In the method of the present embodiment for breeding a plant, the polynucleotide to be hybridized is detected. This makes it possible to easily detect the plant body in which the polypeptide having the activity which improves the plant in tolerance to iron deficiency expresses. Further, as described above, the polypeptide of the present invention plays an important role when a plant copes with iron deficiency. Therefore, a person skilled in the art can easily understand that slight mutation of the amino-acid sequence of the polypeptide would affect on the tolerance to the iron deficiency in the plant. With the use of a conventionally-known technique such as the PCR method, the hybridization method, or a microarray method, it is possible to detect the mutation of the polynucleotide by a unit of one base. Therefore, a person skilled in the art can easily understand that a slight mutation of the amino-acid sequence of the polypeptide encoded by the polynucleotide can be detected. Accordingly, in one aspect, with the method of the present embodiment, a plant improved in tolerance to iron deficiency can be bred by referring to detection of a slight mutation of the amino-acid sequence of the polypeptide.

Further, as described above, the polynucleotide of the present invention can be suitably used in the method of the present invention, for breeding a plant improved in tolerance to iron deficiency. Accordingly, the composition including the polynucleotide of the present invention, and the kit including the polynucleotide of the present invention, can be suitably used to breed a plant improved in tolerance to iron deficiency.

Further, as described later, the base sequence shown in SEQ ID NO: 12, 15, 18, 21, 24, or 27 is a partial sequence of the polynucleotide encoding a homolog of the polypeptide of the present invention (barley (Barley 1, Barley 2), wheat (Wheat), maize (Maize), sorghum (Sorghum), sugarcane (Sugarcane), and rice (AK072874), each of which is shown in FIG. 18). Each of the homologs has high homology in functional domain with respect to the polypeptide of the present invention, so that it is highly probable that each of the homologs has the same function as that of the polypeptide. By using the base sequence shown in SEQ ID NO: 12, 15, 18, 21, 24, or 27, it is possible to determine whether or not a homolog of the polypeptide of the present invention has expressed in a plant body. Therefore, in the same manner as the case where the polypeptide of the present invention is employed, it is possible to easily detect the plant body in which the polypeptide having the activity which improves a plant in tolerance to iron deficiency expresses.

In the present specification, what is meant by the term "oligonucleotide" is tens or hundreds of nucleotides connected together, and this term can be exchanged with the term "polynucleotide". A short oligonucleotide is called "dinucleotide (dimmer)" or "trinucleotide (trimmer)", and a long oligonucleotide is expressed by the number of the nucleotides polymerized with each other, like 30 mer (which is also called 30 bases or 30 nucleotides, in some cases), or 100 mer (which is also called 100 bases or 100 nucleotides, in some cases). The oligonucleotide may be produced as a fragment of a longer polynucleotide, or produced through chemical synthesis.

The oligonucleotide used in the method of the present embodiment for plant breeding, can be used as (i) a PCR primer for obtaining the polynucleotide of the present invention or a fragment of the polynucleotide, or (ii) a hybridization probe.

A person skilled in the art can easily understand that each of the usage described above is based on the hybridization generated between the oligonucleotide used in the method of the present embodiment, for breeding a plant, and the target gene (polynucleotide), and the oligonucleotide is used so as to hybridize with the target gene (polynucleotide).

The fragment of the polynucleotide of the present invention has at least a length of 7 nt (nucleotide), 10 nt, or 12 nt, preferably a length of approximately 15 nt, more preferably a length of at least approximately 20 nt, further preferably a length of at least approximately 30 nt, still further preferably a length of at least approximately 40 nt. However, a person skilled in the art can determine an appropriate length arbitrarily in accordance with the usage described above. The term "fragment having a length of at least 20 nt" serves as a fragment including a base sequence including 20 or more continuous bases in the base sequence shown in SEQ ID NO: 2, 5, 8, 12, 15, 18, 21, 24, or 27, or a fragment including a complementary sequence of the aforementioned base sequence including 20 or more continuous bases. By referring to the present specification, the base sequence shown in SEQ ID NO: 2, 5, 8, 12, 15, 18, 21, 24, or 27 is found, so that a person skilled in the art can easily produce a DNA fragment based on the SEQ ID NO: 2, 5, 8, 12, 15, 18, 21, 24, and 27. For example, restricted endonuclease cleavage or ultrasonic shearing can be easily used to produce a fragment in various sizes. Alternatively, such a fragment can be produced through synthesis. An appropriate fragment (oligonucleotide) is synthesized by a 392 synthesizer manufactured by Applied Biosystems Incorporated. (ABI, 850 Lincoln Center Dr., Forester City, Calif. 94404), or the like.

The oligonucleotide used in the method of the present embodiment, for breeding a plant, may be not only double-strand DNA but also single-strand DNA or single-strand RNA (such as a sense strand or anti-sense strand), which constitutes the double strand DNA. The oligonucleotide can be used as a tool for gene expression manipulation carried out based on an anti-sense RNA mechanism. An anti-sense RNA technique reduces gene products derived from endogenous genes. The introduction of the oligonucleotide can reduce the content of the polypeptide of the present invention. This makes it possible to control tolerance to iron deficiency in plants.

As described above, by using the oligonucleotide used in the method of the present embodiment, for breeding a plant, as (i) the hybridization probe for detecting the polynucleotide encoding the polypeptide having the activity which improves a plant in tolerance to iron deficiency, or (ii) a primer for amplifying the polynucleotide, it becomes possible to easily detect a plant body or a tissue in which the polypeptide having the activity expresses. Further, by using the oligonucleotide as an anti-sense oligonucleotide, it becomes possible to control the expression of the polypeptide having the activity which improves a plant body, its tissue, or its cell, in tolerance to iron deficiency.

7: Method of Detecting Polynucleotide

The present invention further provides a method of detecting a polynucleotide encoding a polypeptide which improves a plant in tolerance to iron deficiency.

The method of the present invention, for detecting the polynucleotide, includes the step of causing a candidate polynucleotide to hybridize with a second polynucleotide including the base sequence shown in SEQ ID NO: 12, 15, 18, 21, 24, or 27.

The term "candidate polynucleotide" refers to a candidate for the polynucleotide encoding the polypeptide which improves a plant in tolerance to iron deficiency. The candidate polynucleotide is preferably cDNA included in a cDNA library.

The base sequence shown in SEQ ID NO: 12, 15, 18, 21, 24, or 27 is a partial sequence of the polynucleotide encoding a homolog of the polypeptide of the present invention, as described below. For this reason, the second polynucleotide specifically hybridizes with the polynucleotide encoding the homolog. Accordingly, by causing the candidate polynucleotide and the second polynucleotide to hybridize with each other, specific hybridization can be detected. This makes it possible to detect the polynucleotide encoding the homolog. The specific hybridization can be detected by (i) a conventionally-known double-strand DNA detecting means, or (ii) a method of labeling the second polynucleotide with a radio isotope, a fluorescent dye, or the like, in advance.

Here, as described above, the homolog has high homology with respect to the polypeptide of the present invention, and it is highly probable that the homolog has the same function as that of the polypeptide. In other words, it is highly probable that the homolog is the polypeptide which improves a plant in tolerance to iron deficiency. As described above, with the method of the present invention, for detecting a polynucleotide, it is possible to detect the polynucleotide encoding the polypeptide which improves a plant in tolerance to iron deficiency.

Specifically, by using the second polynucleotide as a probe, the cDNA library is screened by a conventionally-known method. For example, the polynucleotide is used as the probe so as to be subjected to the hybridization on a membrane to which the cDNA of the cDNA library is transcribed. Thereby, the target cDNA can be detected.

For example, the screening can be carried out with the following cDNA library and probe (i) a cDNA library prepared from barley and, as the probe, the polynucleotide including the base sequence shown in SEQ ID NO: 11 or 26, (ii) a cDNA library prepared from wheat, and, as the probe, the polynucleotide including the base sequence shown in SEQ ID NO: 14, (iii) a cDNA library prepared from maize, and, as the probe, the polynucleotide including the base sequence shown in SEQ ID NO: 17, (iv) a cDNA library prepared from sorghum, and, as the probe, the polynucleotide including the base sequence shown in SEQ ID NO: 20, or (v) a cDNA library prepared from sugarcane, and, as the probe, the polypeptide including the base sequence shown in SEQ ID NO: 23. However, the cDNA library is not limited to these. It is possible to use a cDNA library prepared from closely-related species of a plant described above. Further, the library is preferably, but not limited to, the one prepared from mRNA expressing in roots under iron-deficient conditions. For a method of producing the cDNA library, see "Suzuki, M. et al., Plant J. 8, 85-97 (2006)", for example.

The present invention is not limited to the description of the embodiments above, but may be altered by a skilled person within the scope of the claims. An embodiment based on a proper combination of technical means disclosed in different embodiments is encompassed in the technical scope of the present invention.

Further, each of the academic and patent literatures described in the present specification is incorporated by reference in the present specification.

The following description explains the present invention more specifically with examples. However, the present invention is not limited to these examples. Further, in the following, a conventionally-known gene manipulation technique or the like was used unless otherwise specified.

EXAMPLES

Example 1

Identification of IDEF1

The inventors of the present invention carried out one-hybrid screening method (see One-Hybrid Screening, Li, I., J. and Herskowitz, I.: Science, 262: 1870-1874, 1993) for the purpose of identification of a transcription factor binding to IDE1. However, the transcription factor could not be identified.

This was due to the following reasons. First, introduction of an IDE1-repeated reporter gene into yeast (YM4271) inhibited growth of yeast, and reduced transformation efficiency to approximately one tenth of ordinary transformation efficiency. Further, an amount of expression of IDEF1 was significantly small. That is, the amount of the expression of IDEF1 was significantly small, so that isolation of IDEF1 required a large amount of screening with the low transformation efficiency and the inhibited yeast growth. Then, the yeast strain was replaced with Y187, and the reporter gene and a candidate factor were simultaneously introduced into the yeast (generally, the candidate factor was introduced into the yeast after the reporter gene was introduced). This relatively improved the yeast in growth efficiency and transformation efficiency. However, the improvement failed to achieve the identification of the transcription factor.

The inventors of the present invention diligently studied various IDE1-like sequences existing within proximal regions of known iron-deficiency-inducible genes, such as OsNAAT1 (rice nicotianamine aminotransferase), OsNAS1 and OsNAS2, (both of which are rice nicotianamine synthase), HvNAAT-A (barley nicotianamine aminotransferase), HvNAS1 (barley nicotianamine synthase), and IDS3. Based on their original concept, the inventors of the present invention focused on a canonical Sph motif (TCCATGCAT, SEQ ID NO: 36)/RY element (CATGCA, SEQ ID NO: 37) existing in IDE 1-like sequences present within proximal regions of OsNAAT1 and OsNAS2 (see FIG. 1). In FIG. 1, a part identical with the canonical Sph motif/RY element is underlined with a solid line, and another part different from the canonical Sph motif/RY element is underlined with a broken line.

The canonical Sph motif/RY element is recognizable by a B3 DNA-binding domain of a plant specific ABI3/VP1 family transcription factor. Among the ABI3/VP1 family transcription factors, maize VIVIPAROUS (VP1) and *arabidopsis* abscisic acid insensitive 3 (ABI3: Abscisic Acid Insensitive 3) are well characterized multidomain transcription factors that transmit an abscisic acid signal and transactivate various genes during seed maturation. Further, in rice, OsVP1 is a functional ortholog of maize VP1 and is a sole characterized member of the ASI3/VP1 family (see FIG. 2). In FIG. 2, each gene is indicated by an accession number in Rice Full-Length cDNA Database (KOME), a TIGR LOC number, or an *arabidopsis* genome initiative code. Further, an amino-acid residue change rate is indicated by a bar.

The inventors of the present invention carried out a database search based on homology with respect to a B3 domain of OsVP1, and found five candidate proteins (AK107456, AK072874, AK109920, AK101356 (each of which is the accession number in Rice Full-Length cDNA Database (KOME)), and Os04g_58010 (the TIGR LOC number), see FIG. 2) for a transcription factor binding to IDE1 (ATCAAG-CATGCTTCTTGC, SEQ ID NO: 30). In order to confirm the binding activity to IDE1 in vivo and in vitro, yeast binding assay and gel shift assay (EMSA) were carried out with respect to the candidate proteins.

FIG. 14 is a view schematically illustrating reporter and effector plasmids used for the yeast binding assay. As illustrated in FIG. 14, each of four kinds of repeated IDE cis-element (IDE1×3 (SEQ ID NO: 38), IDE2-IDE1×2 (SEQ ID NO: 39), IDE2×3 (SEQ ID NO: 40) was (i) used as a bait, (ii) fused to a LacZ gene of a pLacZi vector (Clontech), and (iii) used as a reporter.

Further, ORFs of the respective candidate proteins for IDEF1 were obtained by use of the following primers: for OsVP1, a primer including the sequences shown in, respectively, SEQ ID NOS: 42 (forward) and 43 (reverse); for AK107456, a primer including the sequences shown in, respectively, SEQ ID NOS: 44 (forward) and 45 (reverse); for AK072874, a primer including the sequences shown in, respectively, SEQ ID NOS: 46 (forward) and 47 (reverse); for AK109920, a primer including the sequences shown in, respectively, SEQ ID NOS: 48 (forward) and 49 (reverse); and for AK101356, a primer including the sequences shown in, respectively, SEQ ID NOS: 50 (forward) and 51 (reverse). Each of the ORFs was connected to the downstream of a yeast ADH1 promoter of a pGAD424 plasmid so as to be fused in frame to a yeast GAL4 activation domain (GAL4 AD). Then, each of the ORFs was used as an effector. Further, the pGAD424 itself was used as a vector control (VC).

Then, each of the plasmids described above was introduced into yeast (*Saccharomyces cerevisiae* strain YM4271, Clontech) in accordance with manufacturer's instructions, and LacZ activity was measured.

Figure 3:
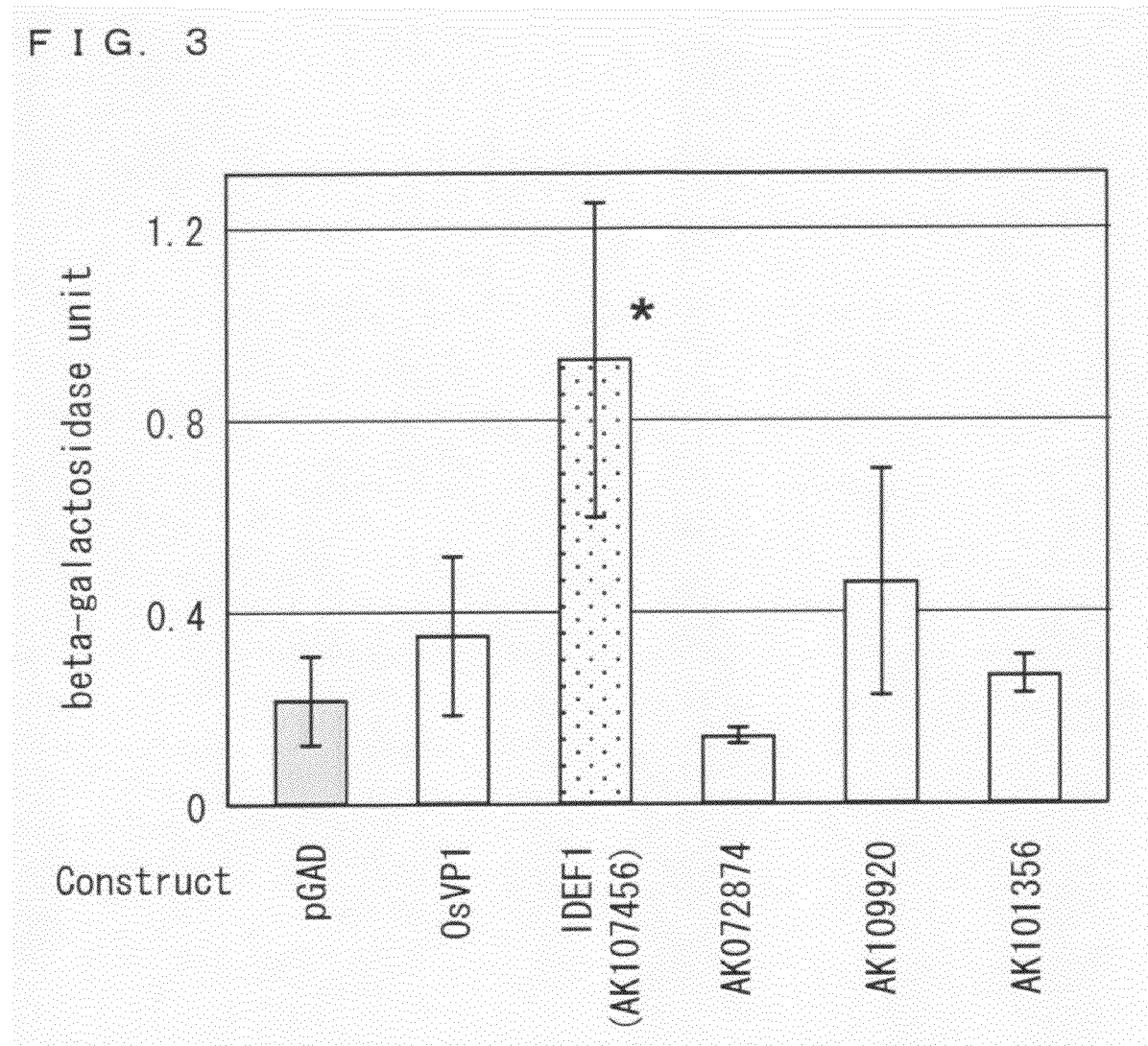
FIG. 3 is a graph showing a result of yeast binding assay with regard to IDE1.

FIG. 3 is a graph showing a beta-galactosidase activity unit (means±s.d.; n=5) in a yeast cell into which the effector containing each of the candidate proteins for IDEF1 was introduced with a reporter gene using IDE1×3 as a bait sequence. FIG. 3 also shows significant differences against vector controls (pGAD), which differences were analyzed by a t-test (*P<0.05). As shown in FIG. 3, only AK107456 induced substantial LacZ activity. In the present specification, AK107456 is, hereinafter, referred to as IDEF1 (IDE-binding factor 1). OsVP1, AK072874, AK109920, and AK101356 did not induce LacZ activity (see FIG. 3). Similar results were obtained by using a reporter using IDE2-IDE1×2 as a bait sequence.

As to IDEF1, the amino-acid sequence is shown in SEQ ID NO: 1, the base sequence of the ORF is shown in SEQ ID NO: 2, and the base sequence of cDNA is shown in SEQ ID NO: 3.

Next, the following operation was carried out for gel shift assay. First, partial ORFs containing a B3 DNA-binding domains of the respective candidate proteins were obtained by use of the following primers: a primer including the sequences shown in, respectively, SEQ ID NOS: 52 (forward) and 53 (reverse), for the 501st-726th amino acids of OsVP1; a primer including the sequences shown in, respectively, SEQ ID NOS: 54 (forward) and 55 (reverse), for the 141st-362nd amino acids of AK107456; a primer including the sequences shown in, respectively, SEQ ID NOS: 56 (forward) and 57 (reverse), for the 151st-433rd amino acids of AK072874; a primer including the sequences shown in, respectively, SEQ ID NOS: 58 (forward) and 59 (reverse), for the 1st-289th amino acids of AK109920; and a primer including the sequences shown in, respectively, SEQ ID NOS: 60 (forward) and 61 (reverse), for the 287th-672nd amino acids of AK101356. Then, each of the partial ORFs was inserted into pMAL-c2 (New England Biolabs) so as to be fused in frame to a maltose-binding protein (MBP) gene. By using a plasmid thus obtained, a fused protein of each of the candidate proteins and the MBP was produced in accordance with manufacturer's instructions. The gel shift assay (EMSA) was carried out in such a manner that the fused protein thus obtained was incubated with a labeled probe containing the base sequence (SEQ ID NO: 39) including tandemly duplicated IDE1.

Figure 4:
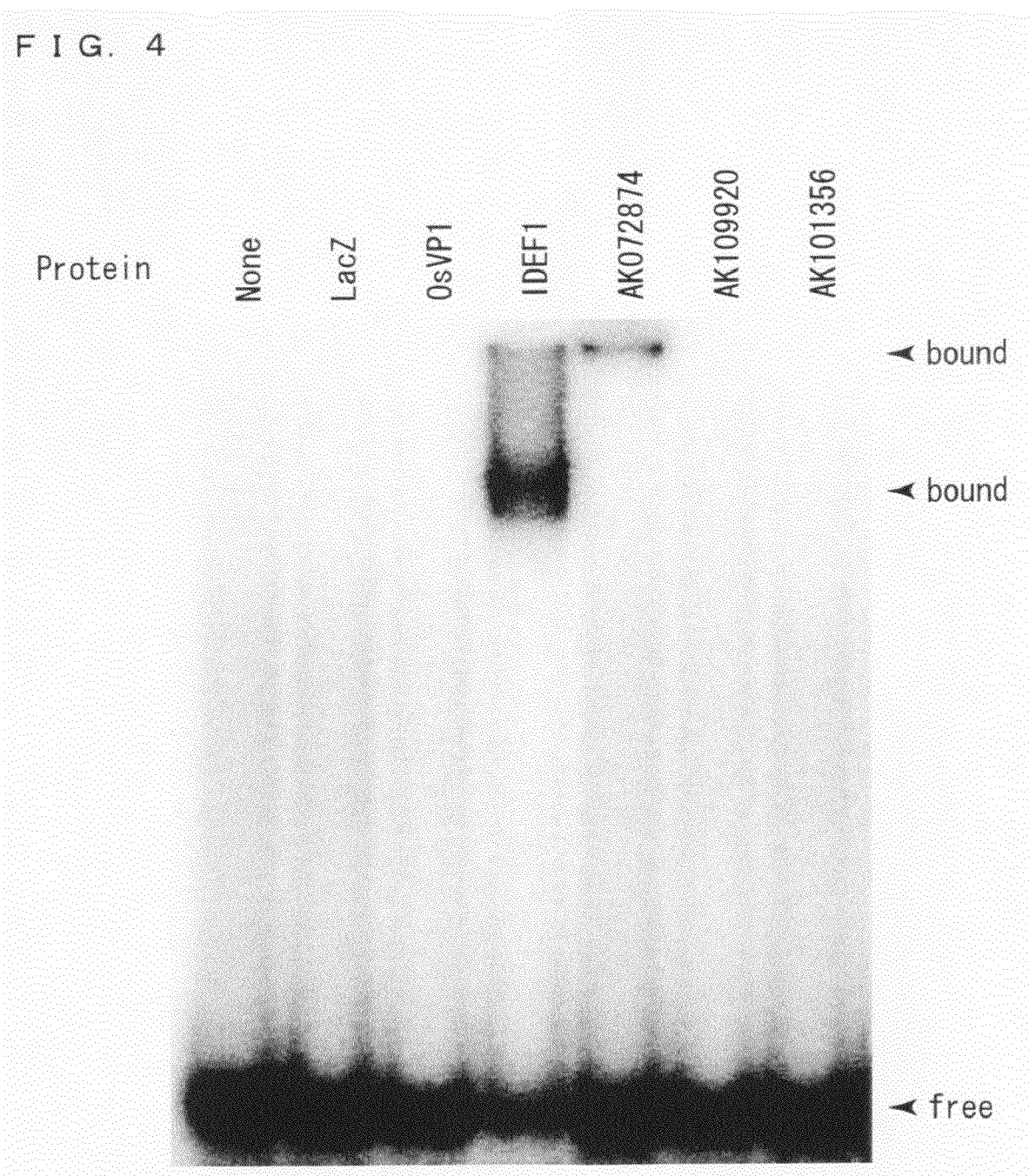
FIG. 4 is a view showing a result of gel shift assay with regard to IDE1.

FIG. 4 shows a result of the gel shift assay. As shown in FIG. 4, IDEF1 and the AK072874 protein specifically bound to IDE1. On the other hand, OsVP1, AK109920, and AK101356 exhibited no specific binding to IDE1 (see FIG. 4).

Figure 5:
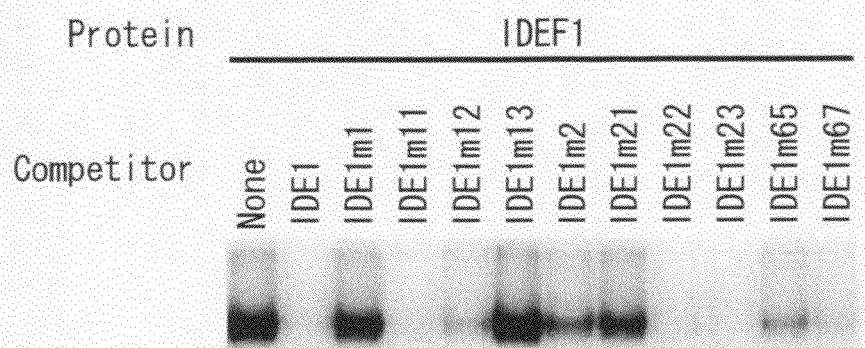
FIG. 5 is a view showing a result of competition experiments with regard to IDE1.

In order to determine precise recognition sequences of IDEF1 and AK072874, competition experiments using mutated IDE1 sequences were carried out. Specifically, by adding 30-fold excess unlabeled polynucleotides respectively including mutated IDE1 sequences (IDEm1-m67) shown in FIG. 1, as competitors, the gel shift assay was carried out in the same manner as described above. FIG. 5 shows the result.

The result of the competition experiments revealed that IDEF1 and AK072874 specifically recognize CATGC (SEQ ID NO: 31, see boxes shown in FIG. 1) existing in IDE1. The CATGC sequence was shorter than the previously reported minimal recognition sequence (CATGCA, SEQ ID NO: 37) of ABI3/VP1 transcription factors. Further, some IDE1-like sequences existing in proximal regions of several genes (Hv-NAS1, IDS3, and the like) do not contain CATGC (SEQ ID NO: 31). By using these IDE1-like sequences as competitors, competition experiments were carried out. The result of the competition experiments revealed that IDEF1 does not bind to these IDE1-like sequences.

Figure 6:
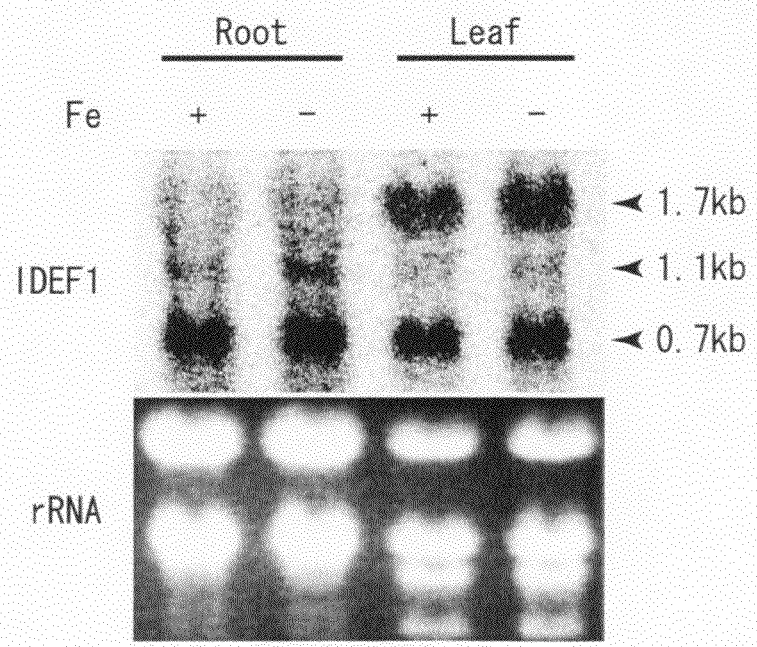
FIG. 6 is a view showing a result of northern blot analysis of IDEF1.

Next, northern blot analysis was carried out in order to detect expression of ABI3/VP1 family genes in vegetative rice roots and leaves. FIG. 6 is a view showing a result of the northern blot analysis of IDEF1 in rice roots and leaves grown under iron sufficiency (+) or deficiency (−) for two weeks. Total RNA was extracted from roots or leaves of a hydroponically-cultured rice plant (Nipponbare) by an SDS-phenol method, and then was subjected to $^{32}$P-based northern blot analysis. Each lane was loaded with 10 µg of the total RNA. Full-length cDNA of IDEF1 was used as a probe. FIG. 6 also shows estimated transcript lengths.

As shown in FIG. 6, the IDEF1 transcripts were constitutively expressed in roots and leaves, with no obvious regulation by iron deficiency. Several bands were detected, among which the longest transcript (~1.7 kb) was abundant in leaves, and presumably corresponded to the full-length of cDNA of IDEF1. OsVP1, AK109920, and AK101356 were also constitutively expressed in roots and leaves, whereas expression of AK072874 was not detected.

Next, localization of IDEF1 in cells was investigated. By use of a particle gun system (Biolistic PDS-1000/He Particle Delivery System, Bio-Rad), transformation of an onion (*Allium cepa*) epidermal cell was carried out, so that a fusion protein (IDEF1-GFP) of C-terminus half of IDEF1 (corresponding to 184th-362nd amino acids) and GFP, or GFP alone (GFP) was transiently expressed. After that, the epidermal cell was taken, and was observed on a glass slide under a phase-contrast microscope. An IDEF1-Green Fluorescent Protein (GFP) fusion protein localized to a nucleus of the onion epidermal cell.

Further, a database search of expressed sequence tags (ESTs) revealed the presence of IDEF1 homologs among various graminaceous species (see FIG. 18). However, no obvious homologs were found in non-graminaceous plants. FIG. 18 is a view showing sequence alignments of the amino-acid sequences of the B3 region (the 243rd-355th putative coding proteins of IDEF1) in the graminaceous species, regarding IDEF1 homolog. The B3 region of each of AK072874 (the 287th-399th putative coding proteins, the amino-acid sequence of B3 region is shown in SEQ ID NO: 28, and the base sequence of the B3 region is shown in SEQ ID NO: 29), OsVP1 (the 526th-637th), and VP1 (the 507th-619th) was aligned as well. GenBank accession numbers are as follows: barley 1, (Hordeum Vulgare, the amino-acid sequence of the B3 region is shown in SEQ ID NO 10, the base sequence of the B3 region is shown in SEQ ID NO: 11, and the base sequence of the EST clone is shown in SEQ ID NO: 12), CB880834 (complementary), and contig 10926 on HarvEST database (http://www.Harvest-web.Org/hweb/bin/wc.Dll?hwebProcess~hmain~&versid=1); barley 2 (Hordeum Vulgare, the amino-acid sequence of the B3 region is shown in SEQ ID NO: 25, the base sequence of the B3 region is shown in SEQ ID NO: 26, and the base sequence of the EST clone is shown in SEQ ID NO: 27), BQ459575; wheat (Triticum aestivum, the amino-acid sequence of the B3 region is shown in SEQ ID NO: 13, the base sequence of the B3 region is shown in SEQ ID NO: 14, and the base sequence of the EST clone is shown in SEQ ID NO: 15), BJ263200 (complementary); maize (Zea mays, the amino-acid sequence of the B3 region is shown in SEQ ID NO: 16, the base sequence of the B3 region is shown in SEQ ID NO: 17, and the base sequence of the EST clone is shown in SEQ ID NO: 18), BG320301; sorghum (Sorghum bicolor, the amino-acid sequence of the B3 region is shown in SEQ ID NO: 19, the base sequence of the B3 region is shown in SEQ ID NO: 20, and the base sequence of the EST clone is shown in SEQ ID NO: 21), BG241297; and sugarcane (Saccharum officinarum, the amino-acid sequence of the B3 region is shown in SEQ ID NO: 22, the base sequence of the B3 region is shown in SEQ ID NO: 23, and the base sequence of the B3 region is shown in SEQ ID NO: 24), CA093694. In FIG. 18, the letter "X" indicates an unknown amino-acid residue due to an unknown base. As shown in FIG. 18, the B3 region of each of IDEF1 homologs of barley 1, barley 2, wheat, maize, sorghum, and sugarcane, showed 60% or greater homology with respect to the B3 region of IDEF1.

Example 2

Identification of IDEF2

In order to identify other IDE-binding transcription factors, one-hybrid screening method employing a commercially-available system (MATCHMAKER one-hybrid system, Clontech) was carried out. By using IDE2-IDE1×2 (see FIG. 14) as a bait sequence (bait), 3.2×10$^6$ cDNA clones in iron-deficient rice roots were screened. A cDNA library in an iron-deficient rice root was made by extracting total RNA from a hydroponically-cultured rice (Nipponbare) root harvested on the 7th day under iron-deficient conditions.

Here, IDE2 was 27 bpi, which was a long sequence as a bait sequence used in the yeast one-hybrid screening method. An endogenous protein of yeast easily binds to a long bait sequence, so that background activity was significantly high in the one-hybrid screening method employing a triplicated-IDE2 bait sequence (a great amount of pseudo positive clones were detected). Therefore, it was significantly difficult to isolate IDEF2. Addition of a great amount of a histidine synthetase inhibitor to the culture medium can suppress the background activity. However, this is not preferable since the addition of the inhibitor to the culture medium has an influence on normal growth of the yeast, and would cause the result to be inaccurate. For this reason, in the present embodiment, the amount of the addition of the histidine synthetase inhibitor was suppressed as much as possible. As a result, a lot of pseudo positive clones were detected.

The inventors of the present invention, as a result of diligent study, analyzed a mutant of IDE2, and from the result, found that a binding portion of the endogenous protein of yeast exists in a junction between IDE2 and IDE2. Based on their original concept, the inventors of the present invention successfully suppressed the background activity by eliminating the junction between IDE2s by designing a bait sequence in which IDE2 and IDE1 tandemly bind to each other and repeated.

Figure 7:
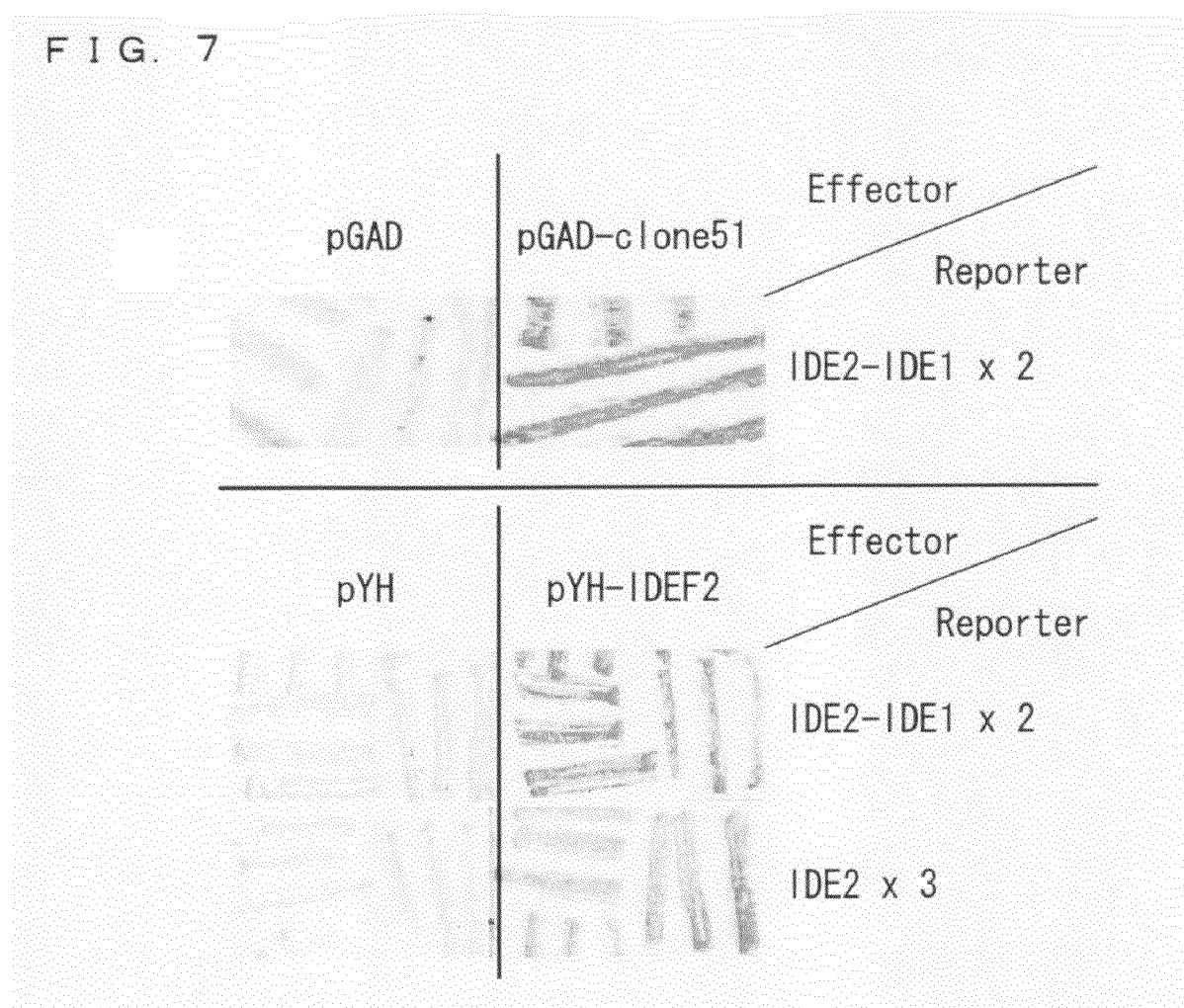
FIG. 7 is a view showing results of a one-hybrid screening method and yeast binding assay, with regard to IDE2.

As a result, one positive clone (clone 51) was obtained as shown in FIG. 7, and a DNA sequence showed that it belongs to NAC family transcription factors. In the present specification, the positive clone is, hereinafter, referred to as IDEF2 (IDE-binding factor 2). As to IDEF2, the amino-acid sequence is shown in SEQ ID NO: 4, the base sequence of the ORF is shown in SEQ ID NO: 5, and the base sequence of cDNA is shown in SEQ ID NO: 6.

Next, yeast binding assay was carried out in the same manner as in Example 1. The ORF of IDEF2 was amplified by use of a primer including the base sequences shown in, respectively, SEQ ID NOS: 62 and 63. Further, an effector (pYH-IDEF2) in which a GAL4 activation domain (GAL4AD) was not fused to IDEF2 was used. FIG. 7 shows the result.

As shown in FIG. 7, in a yeast cell into which the reporter (see FIG. 14) having the lacZ gene in the downstream of IDE2-IDE1×2 or IDE2×3, IDEF2 which was not fused to GAL4AD induced substantial LacZ activity. That is, it was suggested that IDEF2 specifically binds to IDE2 (TTGAACGGCAAGTTTCACGCTGTCACT, SEQ ID NO: 32). Further, it was also suggested that IDEF2 can activate the transcription, and presumably functions as a transcriptional activator in a plant.

Further, by using IDE2×3 as a bait sequence, the one-hybrid screening method was carried out with respect to 5.0×10$^6$ cDNA clones of an iron-deficient barley root. A close homolog of IDEF2 was obtained as a positive clone (HvIDEF2, see FIG. 19, the amino-acid sequence is shown in SEQ ID NO: 7, the base sequence of the ORF is shown in SEQ ID NO: 8, and the base sequence of cDNA is shown in SEQ ID NO: 9).

Figure 8:
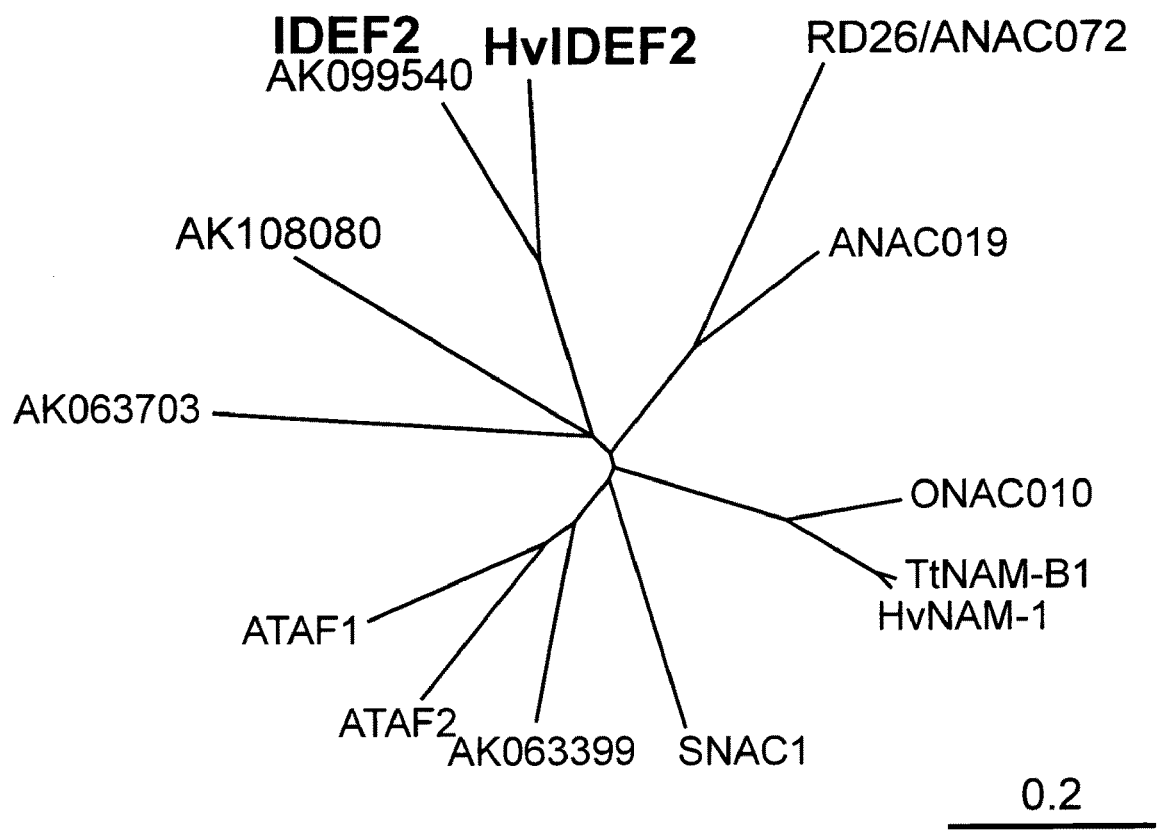
FIG. 8 is a view showing a phylogenic tree for NAC family transcription factors.

The NAC family, to which IDEF2 and HvIDEF2 presumably belong to, constitutes a plant-specific transcription factor family having a highly-conserved N-terminal DNA-binding domain. Some members of the NAC family are reported to be related to developmental programs and drought stress tolerance. FIG. 8 shows a phylogenic tree for NAC family transcription factors: AK063703, AK063399, and AK108080: iron-deficiency-inducible NAC transcription factors in rice; TtNAM-B1 (DQ869673): a NAC transcription factor in pasta wheat regulating senescence; HvNAM-1 (DQ869678) and ONAC010 (NP_911241): homologs of TtNAM-B1 in barley and rice, respectively; RD26/ANAC072 (At4g27410), ATAF1 (AT1g01720), and ATAF2 (At5g08790), ANAC019 (At 1g52890): drought-responsive and/or salt-responsive NAC transcription factors in arabidopsis; and SNAC1 (DQ394702): a drought-responsive NAC transcription factor in rice. As shown in FIG. 8, IDEF2 did not exhibit pronounced similarity to any characterized NAC transcription factors.

Figure 9:
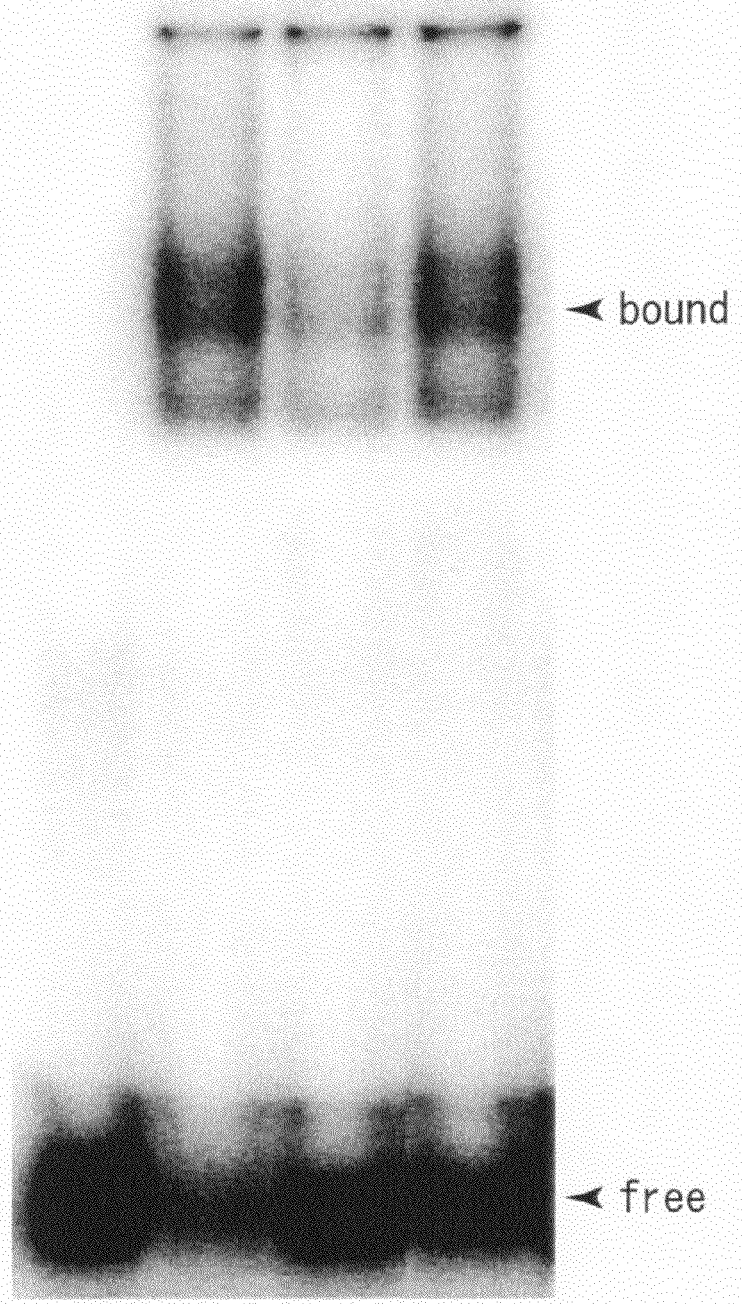
FIG. 9 is a view showing a result of gel shift assay with regard to IDE2.

Then, specific binding of IDEF2 to IDE2 was confirmed by the EMSA method. An IDEF2 NAC domain amplified by a primer including the base sequences shown in, respectively, SEQ ID NOS: 64 and 65, was cloned to a pMAL-c2 vector, and was used to produce an IDEF2-MBP fused protein. Then, a labeled IDEF2 probe including the base sequence (SEQ ID NO: 41) including IDE2 was incubated with 500 ng of the IDEF2-MBP fused protein. FIG. 9 shows the result. As shown in FIG. 9, it was confirmed that the IDE2 probe and the IDEF2-MBP fused protein specifically bound to each other.

Figure 10:
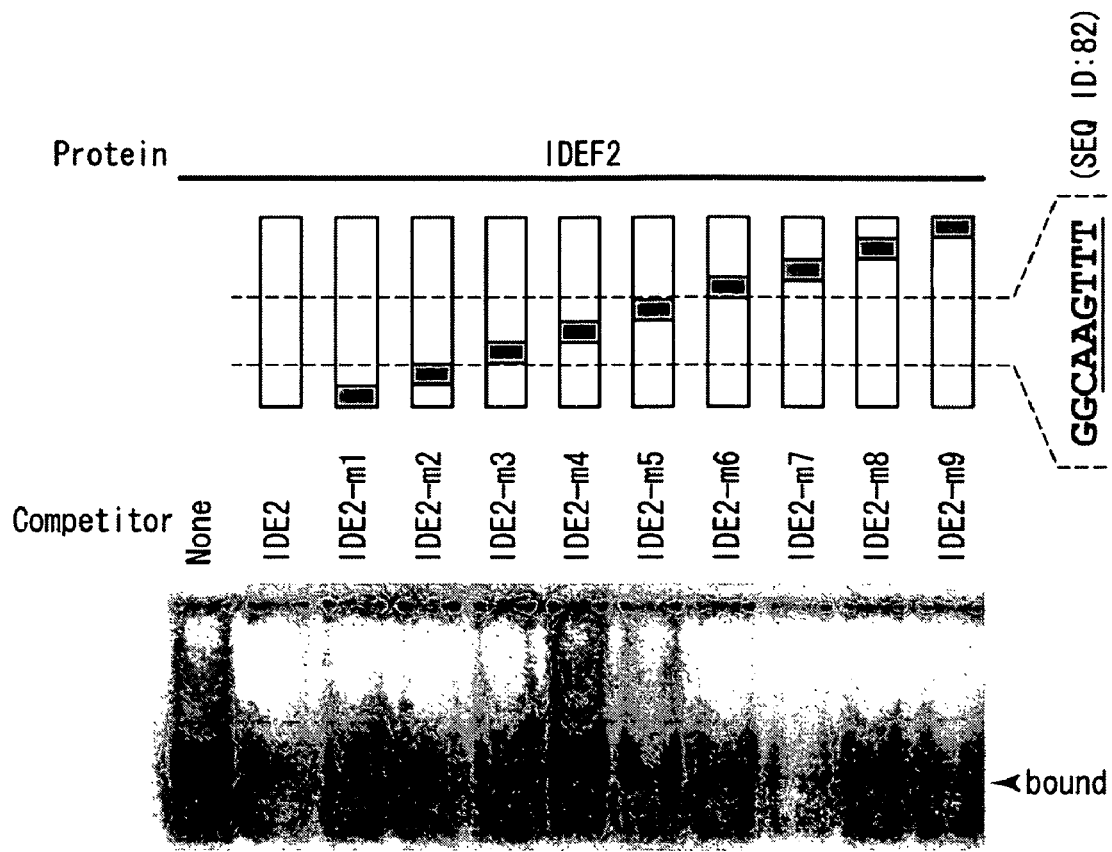
FIG. 10 is a view showing a result of competition experiments with regard to IDE2.

Next, competition experiments were carried out by addition of 30-fold or 50-fold excess unlabeled competitors. FIG. 10 and (a) of FIG. 12 show mutations introduced into polynucleotide fragments, which were used as the competitors. The IDE2 probe was incubated with the 30-fold or 50-fold excess unlabeled competitors and 500 ng of the IDEF2-MBP fused protein. FIG. 10 and (b) of FIG. 12 show the result of the competition experiments. As shown in FIG. 10 and (b) of FIG. 12, IDEF2 predominantly recognized a CA[A/C]G(TTT) sequence (SEQ ID NO: 33 or 34) within IDE2.

Further, by carrying out a Cyclic Amplification and Selection of Targets (CASTing) experiment, it was revealed that the NAC domain of IDEF2 preferentially binds to CA[C/A]G[T/C][T/C/A]. This sequence corresponds to a partial sequence of the recognition sequence determined by the EMSA method. However, some of the iron-deficiency-inducible promoter sequences containing CA[C/A]G[T/C][T/C/A] (SEQ ID NO: 35) did not efficiently compete against the binding of IDEF2 to IDE2. From these results, it was suggested that IDEF2 recognizes (i) CA[A/C]G (SEQ ID NO: 33) as a core sequence, and also (ii) flanking sequences typically present within IDE2, for efficient binding. Additional experiments suggested that IDEF2 also recognizes the 5'-half of the TGACG repeat of a −90/−47 region of a cauliflower mosaic virus 35S promoter, in spite of the absence of CA[A/C]G (SEQ ID NO: 33).

Figure 11:
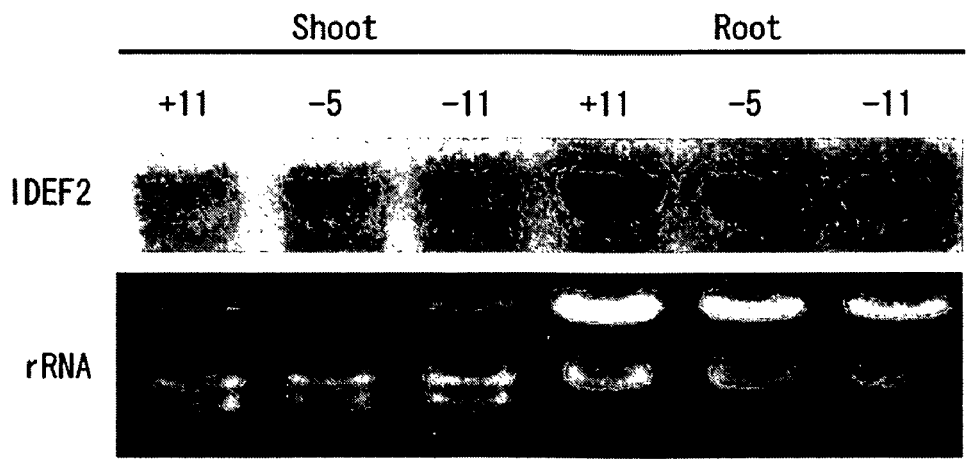
FIG. 11 is a view showing a result of northern blot analysis of IDEF2.

Northern blot analysis of IDEF2 in rice shoots and roots grown under iron sufficiency (+) or iron deficiency (−) for 5 or 11 days was carried out. Each lane was loaded with 10 μg of total RNA. A non-NAC domain region of a 3' end 500 bp of the IDEF2 ORF was amplified by use of the primers shown in SEQ ID NO: 66 and 67 respectively, and was used as a probe. FIG. 11 shows the result.

As shown in FIG. 11, IDEF2 transcripts were constitutively expressed in iron-sufficient and iron-deficient rice shoots and roots, and particularly, higher expression was observed in roots.

Further, as in the Example 1, an IDEF2-GFP fusion protein localized to a nucleus when being expressed in an onion epidermal cell transiently. These results suggest functional properties of IDEF2 mediating iron-deficiency response in rice plants in coordination with IDEF1.

Example 3

Formation of Transformant

In order to provide an IDEF function in a plant body, transgenic tobacco plants were produced, which transgenic tobacco plants contain a beta-glucuronidase (GUS) gene fused sequence in the downstream of two copies of IDE1, and an IDEF1 gene introduced in the downstream of a constitutive 35S promoter (35S-IDEF1), or a vector control (VC).

Tobacco (*Nicotiana tabacum* L., Petit-Havana SR1) leaf disks were subjected to *Agrobacterium*-mediated transformation for introducing an IDE1-IDE1-GUS construct. After kanamycin screening was carried out and $T_1$ seeds were obtained, the $T_1$ leaves of a representative line were subjected to further introduction of 35S-IDEF1 or VC, and double-transformants thus obtained were screened by use of hydromycin B (50 mg $L^{-1}$). Plantlets at the 16-17th day after germination on a MS (Murashige and Skoog) medium containing hygromycin B were transplanted to a new MS solid medium with (+Fe) or without (−Fe) iron. Whole roots as well as the newest and the second newest leaves of two plantlets for each line were harvested 14 days after the transplanting, and used for (i) leaf chlorophyll measurement by a chlorophyll meter (SPAD-502, Konica Minolta), and (ii) detection of GUS activity by a fluorescence method. FIG. 13 shows the result. In FIG. 13, vertical bars represent the means of the readings.

As shown in (a) of FIG. 13, these transformants induced no substantial GUS activity in iron-sufficient roots, as well as in iron-sufficient and iron-deficient leaves. In iron-deficient roots, in contrast, both VC and 35S-IDEF1 plants induced strong GUS activity driven by duplicated IDE1. Further, the 35S-IDEF1 plants showed a tendency of enhanced GUS activity as compared with VC plants. Furthermore, as shown in (b) of FIG. 13, the 35S-IDEF1 plants also showed higher chlorophyll contents under iron deficiency as compared with the VC plants. No other visible phenotype was shown. It was suggested that the introduced IDEF1 gene was subjected to post-translational regulation, which most likely is responsible for root-specific GUS expression under iron-deficient conditions.

In order to further investigate the IDEF1 function, the inventors of the present invention introduced the IDEF1 genes into rice under the control of a constitutive 35S promoter or an iron-deficiency-inducible IDS2 promoter (SEQ ID NO: 68) which is activated in response to iron deficiency (35S-IDEF1 and I2p-IDEF1). $T_1$ transformants and non-transformants (NT) were hydroponically grown in order to analyze the response to iron deficiency.

Figure 15:
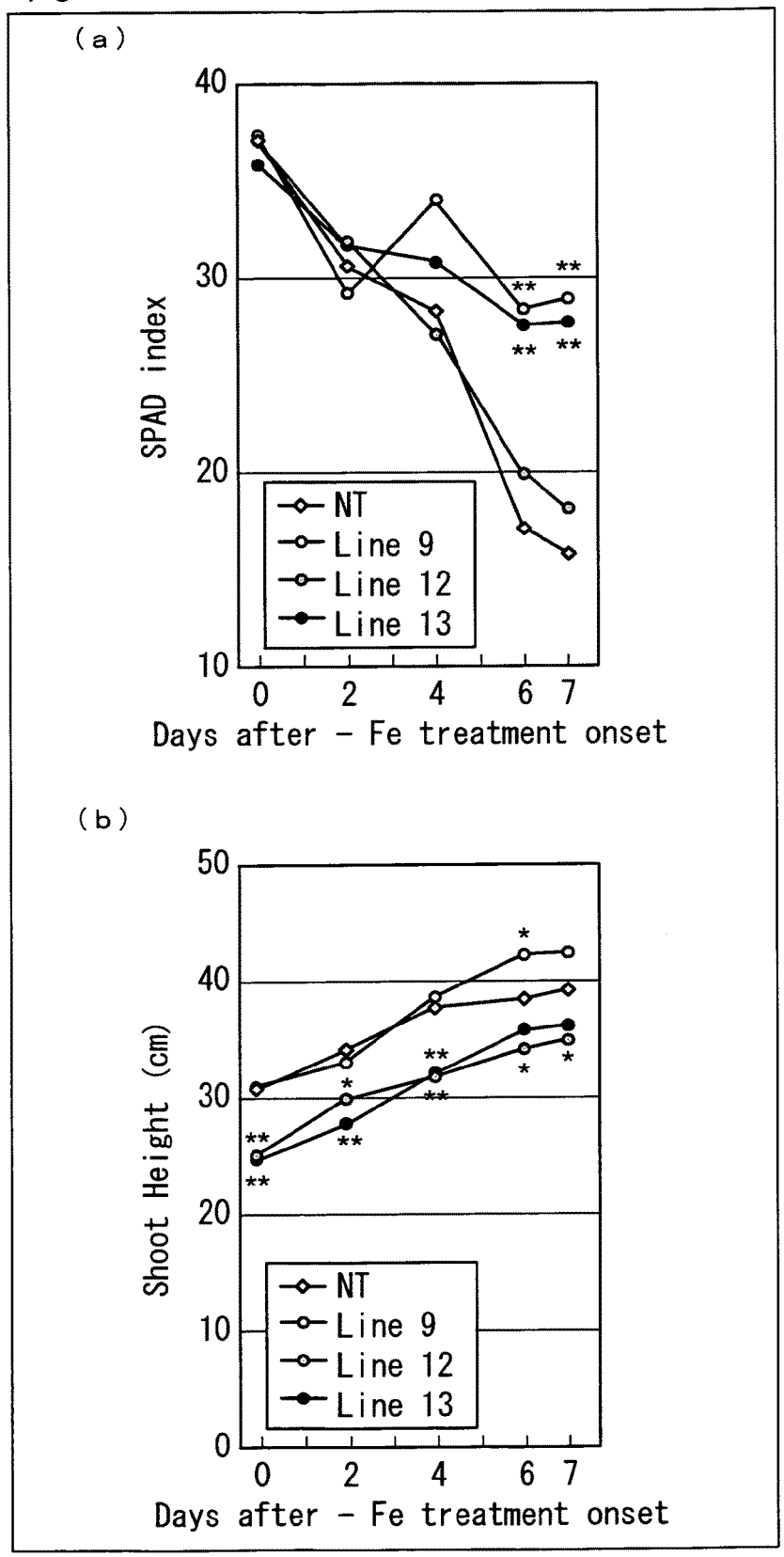
FIG. 15 is a graph showing a property of a transformant of the present invention under iron-deficient conditions ((a) of FIG. 15 shows change in chlorophyll content in a leaf of the transformant of the present invention under an iron-deficient condition, and (b) of FIG. 15 shows change in height of a shoot of the transformant of the present invention under the iron-deficient condition).
Figure 16:
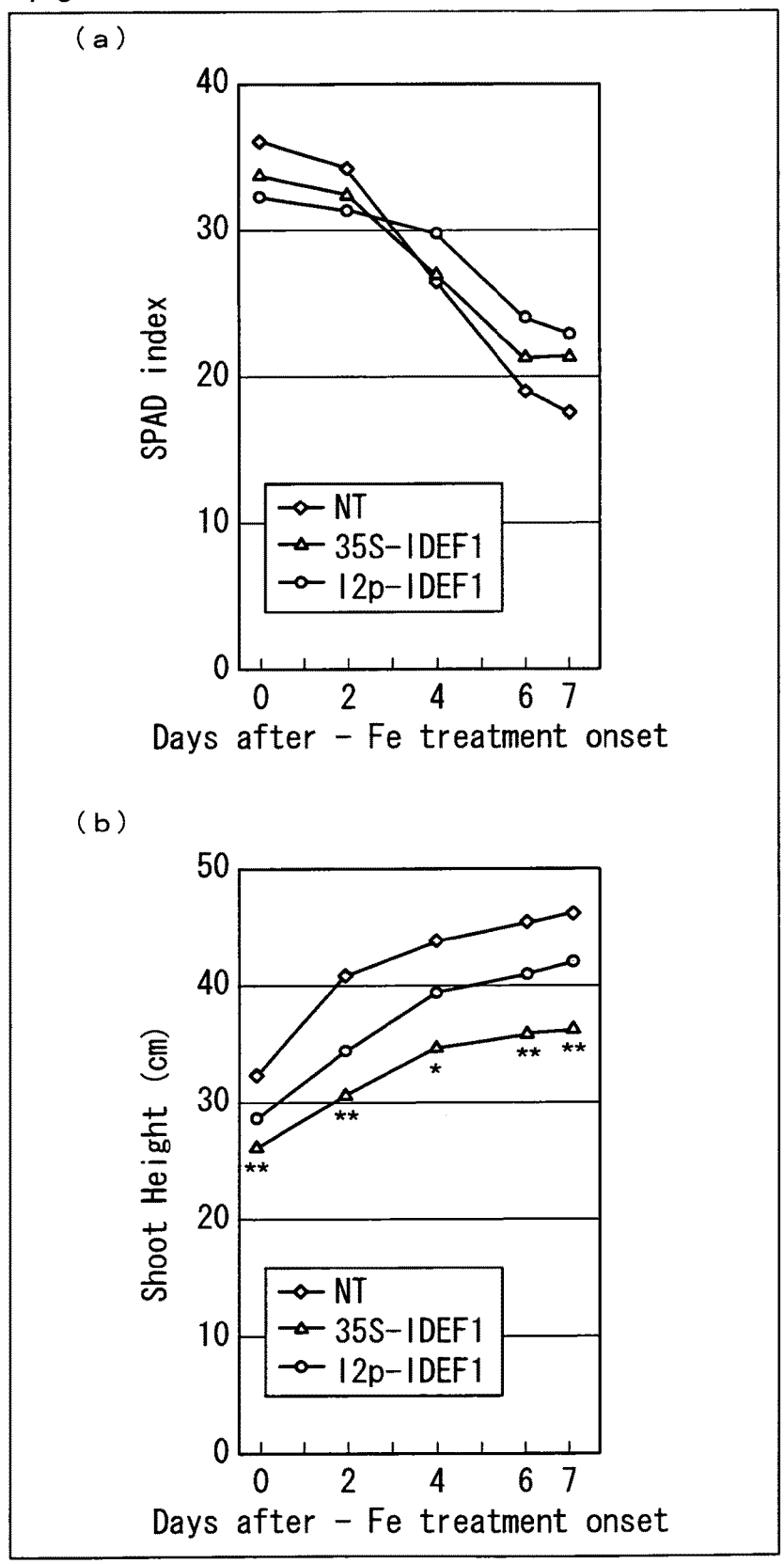
FIG. 16 is a graph showing properties of transformants of the present invention ((a) of FIG. 16 shows a change in chlorophyll content in a leaf of each of the transformants of the present invention under an iron-deficient condition, and (b) of FIG. 16 shows change in height of a shoot of each of the transformants of the present invention under the iron-deficient condition).

35S-IDEF1 and I2p-IDEF1 constructs were introduced into rice (Tsukinohikari) by transformation via an *agrobacterium*. The $T_1$ seeds were germinated and grown in a MS medium containing a 3% sucrose, a 0.8% agarose, and a 50 mg L-1 hygromycin B, at 28° C. for about 16 days with 16-h light/8-h dark cycles. The germination of non-transformants were carried out in an MS medium without hygromycin B. After an acclimation period of 3 days, plantlets were transferred to a hydroponic culture medium. After 7 days for NT and I2p-IDEF1 plants, whereas after 7 to 14 days for 35S-IDEF1 plants, when the shoot heights reached to about 20-30 cm, iron deficiency was imposed by transplanting to a culture medium without Fe(III)-EDTA and pH adjustment. The SPAD meter indexes of the largest leaf and the newest leaf, and shoot heights were measured on days 0, 2, 4, 6 and 7 days after iron deficiency onset. A nutrient solution was renewed on days 0, 4, and 7. FIGS. 15 and 16 show the result.

(a) of FIG. 15 is a graph showing time-course change of the chlorophyll content of the newest leaves of I2p-IDEF1 transformants (lines 9, 12 and 13) and NT on days 0, 2, 4, 6, and 7, after iron deficiency treatment onset. Each dot represents a mean of the SPAD indexes. Significant differences against NT, analyzed by a t-test (*, $p<0.05$; **, $p<0.01$), are also shown.

(b) of FIG. 15 is a graph showing a shoot height of each of the I2p-IDEF1 transformants (lines 9, 12, and 13) and NT. Means are shown with significant differences against NT, which differences were analyzed by the t-test (*, $p<0.05$; **, $p<0.01$).

(a) of FIG. 16 is a graph showing the chlorophyll content of each of NT, 35S-IDEF1, and I2p-IDEF1 transformants. A mean of SPAD indexes of the largest leaves is shown for each of (i) eight independent lines for 35S-IDEF1, (ii) eight independent lines for I2p-IDEF1, and (iii) three NT plants.

(b) of FIG. 16 is a graph showing the shoot height of each of the NT, 35S-IDEF1, and I2p-IDEF1 transformants. A mean of heights of each of (i) eight independent lines for 35S-IDEF1, (ii) eight independent lines for I2p-IDEF1, and (iii) three NT plants, is shown. Significant differences against NT, analyzed by the t-test (*, $p<0.05$; **, $p<0.01$) are shown.

The number of samples in FIGS. 15 and 16 are as follows: $n=8$ for line 12 on days 0, 2, and 4; $n=6$ for NT and line 9 on days 0, 2, and 4, and line 12 on days 6 and 7; $n=5$ for line 13 on days 0, 2, and 4; $n=4$ for NT and line 9 on days 6 and 7; and $n=3$ for line 13 on days 6 and 7.

As shown in (a) of FIG. 15 and (a) of FIG. 16, under the iron-deficient condition, many lines of 35S-IDEF1 and I2p-IDEF1 decreased leaf chlorophyll more slowly than the NT plants did. Time-course observation of the three representative I2p-IDEF1 lines (lines 9, 12, and 13) under iron-deficient treatment revealed substantial tolerance to iron deficiency, especially in lines 9 and 13.

As shown in (b) of FIG. 16, 35S-IDEF1 plants showed slower chlorophyll decrease, as well as I2p-IDEF1 rice plants, however, their primary growth after germination was considerably retarded. An adverse effect of constitutive overexpression of stress response-related transcription factors has been also reported for DREB transcription factors regulating drought-responsive genes. This suggests advantage of choosing stress-inducible promoters for enhancing the expression of transcription factors.

Example 4

RNAi Method

In order to investigate an IDEF2 function, rice transformants in which expression of IDEF2 was suppressed by an RNAi method were produced. Specifically, 400 bp 5' UTR and 300 bp 3' UTR of IDEF2 were amplified, and then inserted into a pIG-RNAi-DEST vector. The transformation of rice was carried out by a conventional technique. 20 independent 5' RNAi transformants and 20 independent 3' RNAi rice plants were produced.

Forty lines of rice transformants were obtained, among which lines (lines 1, 2, and 3) in which expression was strongly suppressed, and a line (line 4) in which expression was slowly suppressed were selected. Specifically, a line (line 1) strongly suppressing IDEF2 was selected from 5' RNAi rice, and two lines (lines 2 and 3) strongly suppressing IDEF2 were selected from 3' RNAi rice. A line (line 4) slowly suppressing IDEF2 was selected from 3' RNAi rice. $T_1$ seeds were analyzed. (a) of FIG. 17 shows the result of northern blot analysis carried out with respect to each line.

The rice was hydroponically grown with 14-h light at 30° C./10-h dark at 25° C. cycles. After 29 to 31 days from germination, when heights of the plants reached to 34 cm, iron deficiency was imposed by removing Fe(III)-EDTA from a culture solution. The plants were harvested after 7 days from iron deficiency onset.

For each line, an expression amount of Fe(II)-nicotianamine transporter OsYSL2 having a function of transporting iron chelate compounds in rice bodies was measured by a conventional RT-PCR method. (b) of FIG. 17 shows the result.

Figure 17:
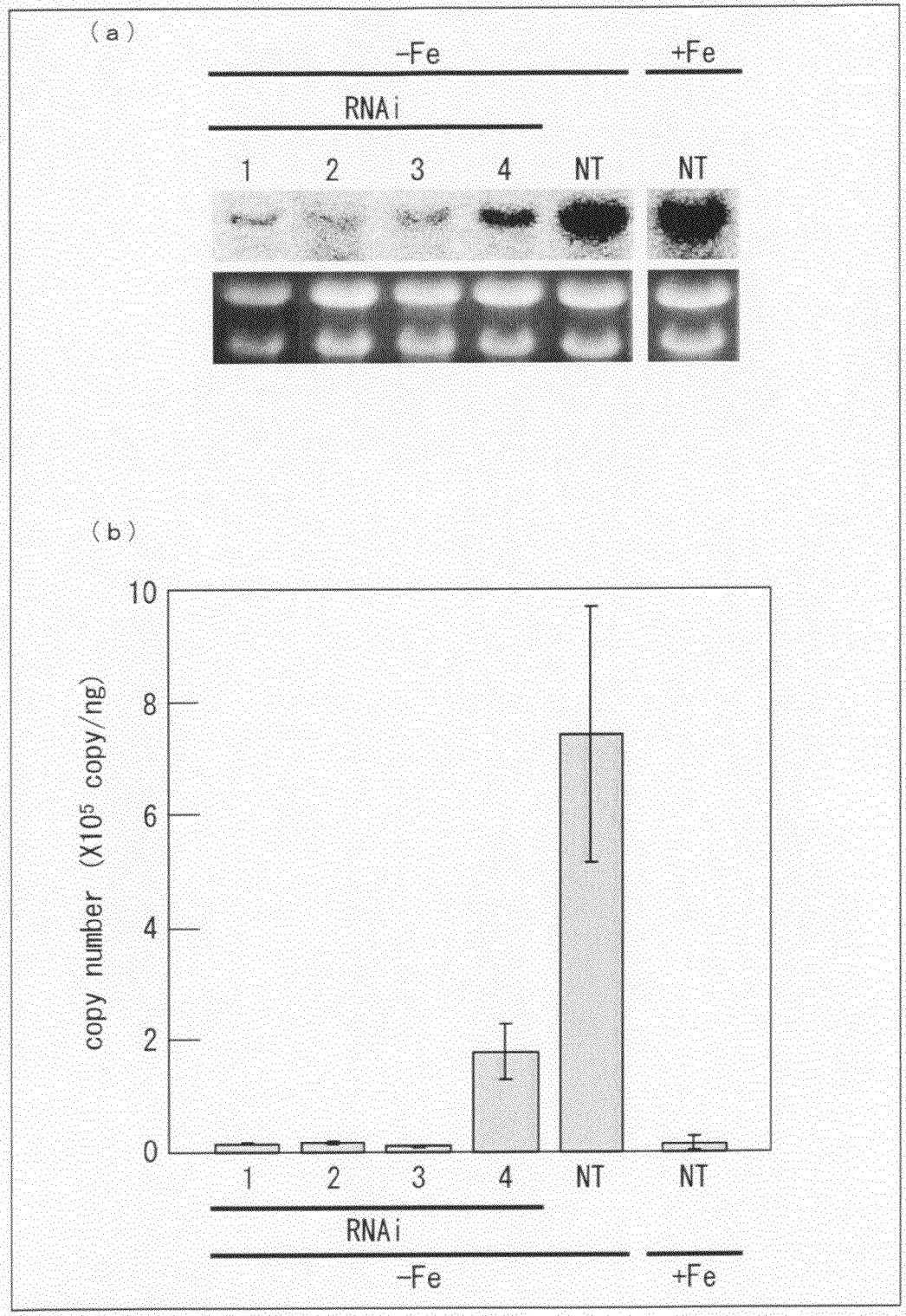
FIG. 17 is a view showing a result in a case where expression of IDEF2 was suppressed by use of RNAi ((a) of FIG. 17 shows suppressed expression of IDEF2, and (b) of FIG. 17 shows an expression amount of each of the gene related to an iron-acquisition mechanism in plants in which the expression of IDEF2 was suppressed by use of RNAi).

As shown in (b) of FIG. 17, the expression of OsYSL2 was significantly suppressed in RNAi rice in growth under the iron-deficient condition. The lines (lines 1, 2, and 3) where the expression was strongly suppressed showed strong suppression of the expression of OsYSL2, and the line (line 4) where the expression was slowly suppressed showed less suppression of the expression of OsYSL2. This revealed IDEF2 is related to expression control of OsYSL2, and is involved in the iron-utilization mechanism of a plant.

With the present invention, expression of genes related to iron acquisition or utilization of plants can be increased, so that it is possible to provide plants improved in tolerance to iron deficiency.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

With the present invention, it is possible to obtain plants improved in tolerance to iron deficiency. Therefore, it is possible to obtain crops which can grow in alkali soil where little solubilized iron exists.

Graminaceous crops constitute major world' food supply, among which rice and maize are highly susceptible to iron deficiency. The inventors of the present invention successfully produced rice plants with enhanced tolerance to low iron availability by introduction of barley HvNAAT genes. Genetic enhancement of a wide range of genes needs manipulation of basal regulatory systems (including transcription factors) related to response to iron deficiency. Further, the inventors of the present invention revealed IRO2 overexpression also improves tolerance to iron deficiency. Manipulation of IDEF1 in combination of IDEF2, IRO2, and other unknown factors would provide novel types of crops and other plants carrying favorable traits on problematic soils.
Sequence Listing Free Text

The invention claimed is:

1. A method of creating a plant improved in tolerance to iron deficiency compared to a corresponding non-transformant, the method comprising the steps of:
   introducing a polynucleotide encoding a polypeptide comprising the amino-acid sequence shown in SEQ ID NO: 1 into a plant; and
   selecting a transgenic plant which has a phenotype of improved tolerance to iron deficiency, compared to the corresponding non-transformant.

2. The method of claim 1, wherein the polynucleotide comprises the base sequence shown in SEQ ID NO: 2.

* * * * *

SEQUENCE LISTING

<160> NUMBER OF SEQ ID NOS: 117

<210> SEQ ID NO 1
<211> LENGTH: 362
<212> TYPE: PRT
<213> ORGANISM: Oryza sativa

<400> SEQUENCE: 1

Met Gly Gln Met Asp Gly Gly Asp Gly Gly Gly Gly His Pro Tyr

```
         1               5                  10                 15
    His Tyr Gln Ala Leu Leu Ala Ala Val His Gln Gln Thr Val Pro Phe
                    20                  25                  30

Pro Asn Pro Phe Pro Ala Pro Ser Ser Gly Ala Glu Pro His Pro
                35                  40                  45

His Asn His Asn His Asn His Asn His Asn Ile His Asn Ser
        50                  55                  60

His Asn His Asn His Asn His Asn Ala Ala Pro His Pro Cys His Thr
    65                  70                  75                  80

Pro Thr Pro Thr Pro Thr Pro Arg Gly Phe Ala Asp Trp Ser Ala Ser
                    85                  90                  95

Thr Ser Ala Phe Thr Ser Leu Ala Ala His Ser Ser Thr Ala Pro Ser
                    100                 105                 110

Asn Ala Val His Tyr Ser Phe Ser Pro Cys Tyr Ala Phe Trp Thr His
                    115                 120                 125

Tyr Met Leu Asn Lys Asn Ala Tyr Pro Thr Ser Phe Pro Ala Pro His
                130                 135                 140

Asp Asp His Leu Arg Leu Ala Asn Asn Asn His Pro Arg Asp Ala Pro
    145                 150                 155                 160

Gly Pro Ala Ser Ser Tyr Gly Val Glu Ser Phe Thr Ser Pro Ser Met
                    165                 170                 175

Ala Pro Asn Ile Cys Thr His Met Pro Pro Ile Glu Gly Pro Ile Ser
                180                 185                 190

Ala Lys Glu Asp Lys Lys Pro Glu Ile Leu Pro Arg Val Val Lys Ser
                195                 200                 205

Ser Asp Glu Leu Glu Thr Arg Asn Ser Asn Val Glu Phe His Ser Glu
                210                 215                 220

Thr Val Gly Thr Phe Pro Glu Ser Lys Gln Gly His Asp Ser Arg Ala
    225                 230                 235                 240

Thr Lys Leu Leu Asn Ser Gly Glu Tyr Gln Val Ile Leu Arg Lys Glu
                    245                 250                 255

Leu Thr Lys Ser Asp Val Gly Asn Val Gly Arg Ile Val Leu Pro Lys
                    260                 265                 270

Lys Asp Ala Glu Ala Ser Leu Pro Pro Leu Leu Gln Arg Asp Pro Leu
                    275                 280                 285

Ile Leu His Met Asp Asp Met Val Leu Pro Val Thr Trp Lys Phe Lys
                    290                 295                 300

Tyr Arg Tyr Trp Pro Asn Asn Lys Ser Arg Met Tyr Ile Leu Asp Ser
    305                 310                 315                 320

Ala Gly Glu Phe Leu Lys Thr His Gly Leu Gln Ala Gly Asp Val Ile
                    325                 330                 335

Ile Ile Tyr Lys Asn Leu Ala Pro Gly Lys Phe Ile Ile Arg Gly Glu
                    340                 345                 350

Lys Ala Ile His Gln Gln Thr Thr Asn Pro
                    355                 360

<210> SEQ ID NO 2
<211> LENGTH: 1089
<212> TYPE: DNA
<213> ORGANISM: Oryza sativa

<400> SEQUENCE: 2
atggggcaaa tggacggcgg cgacggcggc ggcggcggcc accccctacca ctaccaggct     60 ctcctggccg ccgtccacca gcagaccgtc cccttctcca tcccttccc cgccccctcc     120
```

| | | | | |
|---|---|---|---|---|
| tccggagccg | agccccccca | cccgcacaac | cacaaccaca | accacaatca | caaccacaat | 180 |
| attcacaatt | ctcacaatca | caaccacaat | cacaatgctg | ctcctcaccc | ttgtcacact | 240 |
| cccactccca | ctcccactcc | cagaggtttc | gccgactgga | gcgcctccac | cagcgccttc | 300 |
| acctcccttg | ccgcgcactc | ttctactgcc | cccagcaatg | ccgttcacta | cagcttctcc | 360 |
| ccctgctatg | ccttctggac | acattacatg | ctcaacaaga | acgcctaccc | cacctccttc | 420 |
| cctgcgccac | acgacgacca | cctgcgcctt | gccaacaaca | atcatcctag | agacgcacca | 480 |
| ggtcctgcat | ccagctacgg | ggtcgagtct | tttacttcac | cgtccatggc | accgaatatt | 540 |
| tgcacccaca | tgcctcccat | agaaggaccc | atatctgcca | aggaagataa | gaaaccagag | 600 |
| attttgccta | gagtggttaa | gagcagtgat | gaattggaaa | ccagaaacag | caatgttgaa | 660 |
| tttcactctg | agacagttgg | tactttccct | gagtcgaagc | aaggccatga | cagtcgtgct | 720 |
| actaaactac | tcaactcggg | agaataccaa | gtcattctgc | gcaaggagct | gacaaagagt | 780 |
| gatgttggaa | atgttggaag | aattgtgcta | cccaagaagg | atgcagaggc | tagtcttcca | 840 |
| cctttgttgc | aaagggatcc | tttgatactg | cacatggacg | acatggtgct | cccagtgaca | 900 |
| tggaagttta | agtacaggta | ctggccaaat | aacaaaagca | gaatgtacat | tctggattct | 960 |
| gcaggtgaat | ttctgaagac | acatggtctt | caggctgggg | atgtcatcat | tatctacaaa | 1020 |
| aacttggctc | ctggcaaatt | tattatccga | ggagagaagg | ccattcatca | gcagacaaca | 1080 |
| aatccctag | | | | | 1089 |

<210> SEQ ID NO 3
<211> LENGTH: 1704
<212> TYPE: DNA
<213> ORGANISM: Oryza sativa

<400> SEQUENCE: 3

| | | | | |
|---|---|---|---|---|
| ctcttcttcc | tcctcctggg | gcctagccgc | ctaggggggt | tgtggcctgc | gactgcgact | 60 |
| tcttcctctg | ccttctgctc | tctgcctctg | agtatatgga | atatggtgtg | tgcgtgaaga | 120 |
| gaaattaagt | gagggagggg | aaagcgagcg | aacagggcaa | caatgggca | aatggacggc | 180 |
| ggcgacggcg | gcggcggcgg | ccaccctac | cactaccagg | ctctcctggc | cgccgtccac | 240 |
| cagcagaccg | tccccttcc | caatcccttc | ccgccccct | cctccggagc | cgagcccccc | 300 |
| cacccgcaca | accacaacca | caaccacaat | cacaaccaca | atattcacaa | ttctcacaat | 360 |
| cacaaccaca | atcacaatgc | tgctcctcac | ccttgtcaca | ctcccactcc | cactcccact | 420 |
| cccagaggtt | tcgccgactg | gagcgcctcc | accagcgcct | tcacctccct | tgccgcgcac | 480 |
| tcttctactg | cccccagcaa | tgccgttcac | tacagcttct | cccctgcta | tgccttctgg | 540 |
| acacattaca | tgctcaacaa | gaacgcctac | cccacctcct | tccctgcgcc | acacgacgac | 600 |
| cacctgcgcc | ttgccaacaa | caatcatcct | agagacgcac | caggtcctgc | atccagctac | 660 |
| ggggtcgagt | cttttacttc | accgtccatg | gcaccgaata | tttgcaccca | catgcctccc | 720 |
| atagaaggac | ccatatctgc | caaggaagat | aagaaaccag | agattttgcc | tagagtggtt | 780 |
| aagagcagtg | atgaattgga | aaccagaaac | agcaatgttg | aatttcactc | tgagacagtt | 840 |
| ggtactttcc | ctgagtcgaa | gcaaggccat | gacagtcgtg | ctactaaact | actcaactcg | 900 |
| ggagaatacc | aagtcattct | gcgcaaggag | ctgacaaaga | gtgatgttgg | aaatgttgga | 960 |
| agaattgtgc | tacccaagaa | ggatgcagag | gctagtcttc | cacctttgtt | gcaaagggat | 1020 |
| cctttgatac | tgcacatgga | cgacatggtg | ctcccagtga | catggaagtt | taagtacagg | 1080 |
| tactggccaa | ataacaaaag | cagaatgtac | attctggatt | ctgcaggtga | atttctgaag | 1140 |

```
acacatggtc ttcaggctgg ggatgtcatc attatctaca aaaacttggc tcctggcaaa   1200
tttattatcc gaggagagaa ggccattcat cagcagacaa caaatcccta gatgcatttg   1260
gggttaattg caacagtgtt agttgatgca tttgaaggga aggacgtgga cttaccataa   1320
gttggcaatc caggagaagt tgaaagtgtc atcgattttt atatcactgg tggccaccat   1380
cacatggaca agattaaag cgcatgcagc ttggacctgt ttaactctga atgaatgagg   1440
acgaaaaaaa gacaagattg gtagagtatt ggaagtgttg caatgggct tctacagctt    1500 atcttgggtt gagaaaagca cttgtcagtt tatttaattc agttatgttg gggagcttga   1560
cttgtagttt tcagaacaat atatttgcag cttctgtaaa tattttttgga tctataagat  1620 aaaagagagt ggtgtgtgat tttgcttttg atgtcatcca tctattttctc atactaatgc  1680 caggaatgtc tgttcattgt cagc                                          1704
```

<210> SEQ ID NO 4
<211> LENGTH: 449
<212> TYPE: PRT
<213> ORGANISM: Oryza sativa

<400> SEQUENCE: 4

```
Met Ala Gln Thr Cys Leu Pro Pro Gly Phe Arg Phe His Pro Thr Asp
1               5                   10                  15

Val Glu Leu Val Ser Tyr Tyr Leu Lys Arg Lys Ile Met Gly Lys Lys
            20                  25                  30

Pro Leu Ile Gln Ala Ile Ser Asp Val Glu Leu Tyr Lys Phe Ala Pro
        35                  40                  45

Trp Asp Leu Pro Ala Gln Ser Cys Leu Gln Ser Arg Asp Leu Glu Trp
    50                  55                  60

Phe Phe Phe Cys Pro Arg Asp Lys Lys Tyr Pro Asn Gly Ser Arg Thr
65                  70                  75                  80

Asn Arg Ser Thr Pro Asn Gly Tyr Trp Lys Thr Ser Gly Lys Asp Arg
                85                  90                  95

Thr Ile Glu Leu Asn Ser Arg Ile Val Gly Ser Lys Lys Thr Leu Ile
            100                 105                 110

Phe His Glu Gly Lys Ala Pro Lys Gly Asn Arg Thr Asp Trp Val Met
        115                 120                 125

Tyr Glu Tyr Lys Met Glu Asp Asn Gln Leu Val Ser Ala Gly Phe Ser
    130                 135                 140

Lys Asp Asp Phe Val Leu Cys Lys Ile Phe Lys Lys Ser Gly Leu Gly
145                 150                 155                 160

Pro Arg Ile Gly Glu Gln Tyr Gly Ala Pro Phe Asn Glu Glu Glu Trp
                165                 170                 175

Glu His Ala Asp Ala Glu Met Phe Pro Leu Leu Pro Asn Val Glu Thr
            180                 185                 190

Ser Val Phe Pro Leu Leu Pro Ser Ser Glu Val Val Asn Ser Thr Asp
        195                 200                 205

Asp Thr Arg Val Gln Pro Ser Val Ala Ala Arg Ala Ile Glu Glu Leu
    210                 215                 220

Pro Val Gln His Leu Pro His Val Cys Ala Gly Asn Gly Ser Thr Tyr
225                 230                 235                 240

Gln Asn Ile Thr Val Thr Gly Glu Ser Ala Leu Met Glu Leu Pro Ser
                245                 250                 255

Gln His Ser Val Glu Ser Ile Gly Asp Glu Val Val Ser Val Asp Asn
            260                 265                 270

Cys Ser Asn Val Val Asn Asn Ala Asp Ser Pro Val Ile Glu Gly Leu
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Val | Leu | Glu | Glu | Leu | Ser | Arg | Phe | Leu | Thr | Asp | Ser | Pro | His | His | Gly |
| 290 |     |     |     |     | 295 |     |     |     |     | 300 |     |     |     |     |     |
| Asn | Pro | Val | Gly | Glu | His | Ser | Gly | Leu | Pro | Pro | Met | Ser | Glu | Ala | Glu |
| 305 |     |     |     |     | 310 |     |     |     |     | 315 |     |     |     |     | 320 |
| Ala | His | Ala | Phe | Glu | Val | Ser | Thr | Asn | Asp | Leu | Tyr | Asn | Glu | Ile | Ala |
|     |     |     |     | 325 |     |     |     |     | 330 |     |     |     |     | 335 |     |
| Gly | Leu | Ala | Glu | Leu | Gly | Val | Pro | Asn | Gly | Asp | Gly | Phe | Ser | Pro | Ser |
|     |     |     | 340 |     |     |     |     | 345 |     |     |     |     | 350 |     |     |
| Asn | Ala | Gly | Val | Thr | Glu | Gln | Gln | Pro | Thr | Tyr | Phe | Gly | Val | Pro | Asn |
|     |     | 355 |     |     |     |     | 360 |     |     |     |     | 365 |     |     |     |
| Ser | Glu | Asn | Tyr | Val | Asn | Met | Asp | Asp | Ile | Phe | Ala | Pro | Asp | Thr | Arg |
|     | 370 |     |     |     |     | 375 |     |     |     |     | 380 |     |     |     |     |
| Leu | Ser | Tyr | Ala | Tyr | Pro | Leu | Pro | Asn | Asn | Gln | Phe | Trp | His | Tyr | Pro |
| 385 |     |     |     |     | 390 |     |     |     |     | 395 |     |     |     |     | 400 |
| Met | Asp | Gln | Phe | Thr | Tyr | Ser | Thr | Thr | Leu | Ser | Ala | Ala | Phe | Pro | Ser |
|     |     |     |     | 405 |     |     |     |     | 410 |     |     |     |     | 415 |     |
| Gly | Asp | Ser | Arg | Pro | Thr | Met | Arg | Ile | Val | Asp | Asp | Leu | Pro | Ala | Ala |
|     |     |     | 420 |     |     |     |     | 425 |     |     |     |     | 430 |     |     |
| Ala | Asn | Asn | Gly | Gly | Phe | Ala | Ser | Lys | Pro | Ser | Met | Gln | Phe | Pro | Leu |
|     |     | 435 |     |     |     |     | 440 |     |     |     |     | 445 |     |     |     |
| Ser |

<210> SEQ ID NO 5
<211> LENGTH: 1350
<212> TYPE: DNA
<213> ORGANISM: Oryza sativa

<400> SEQUENCE: 5

```
atggctcaaa cttgcttgcc acctggcttt cgttttcatc caacagatgt tgaacttgtt      60
tcatactatt tgaaaaggaa gattatggga agaagcctc ttattcaagc tatatcagat     120
gttgaactgt ataaatttgc tccctgggat cttcctgctc aatcctgtct ccagagcaga     180
gatcttgaat ggttcttctt tgcccacga gacaagaaat atcctaatgg gtctaggaca     240
aatcgttcca caccaaatgg ttactggaaa acaagtggga agatagaac gattgagctt     300
aactctcgca ttgttgggtc aaagaaaaca ctgattttc atgaaggcaa agcacctaaa     360
ggcaacagga ctgattgggt gatgtacgaa tacaaatgg aagacaatca attggtctct     420
gctggtttct caaggatga ttttgtcctc tgcaaaattt tcaagaaaag tggccttggt     480
ccaaggattg gggagcaata tgggctcca tttaatgaag aagaatggga gcatgcagat     540
gctgaaatgt tcccttgct gccaaatgtt gaaacttctg tgtttccatt gctgccctct     600
tcagaggtag taaattctac tgatgataca cgtgttcagc cttctgttgc tgccagagct     660
attgaggaac tacctgtgca gcatttacct catgtatgtg ctgggaatgg atcaacatat     720
caaaatatta ctgttactgg tgaaagtgct ctcatggaac tgccttccca gcactctgtt     780
gaatctattg gtgatgaggt agtttctgtg acaactgtt ctaatgtggt caataatgca     840
gacagtcctg taattgaggg gcttgtattg gaggaacttt ctaggttttt aactgattct     900
cctcatcatg gcaaccctgt tggggagcac tctggtctcc caccaatgtc tgaggctgaa     960
gctcatgctt ttgaggttag cacaaatgat ctgtacaatg aaattgcagg gcttgctgaa    1020
ttgggtgtgc aaatggtga tggatttct ccgtccaatg ctggtgttac tgaacaacag    1080
cccacatact ttggagttcc taacagtgaa aattatgtaa atatggatga tatctttgct    1140
```

| | | | |
|---|---|---|---|
| ccagacacaa | gattatccta | tgcatatcct | ttgccaaaca accaattttg gcattatccc | 1200 |
| atggatcagt | tcacatacag | tactactcta | tctgctgcct ttccatctgg tgactcgcgt | 1260 |
| ccaactatgc | gcattgttga | tgatttacct | gctgctgcta ataacggtgg ctttgcttca | 1320 |
| aaacccagca | tgcagttccc | actgtcataa | | 1350 |

<210> SEQ ID NO 6
<211> LENGTH: 2565
<212> TYPE: DNA
<213> ORGANISM: Oryza sativa

<400> SEQUENCE: 6

| | | | | |
|---|---|---|---|---|
| gggttgcttc | ctccgaaaat | cctcatcctc | tccattgacc agacggcggc gcaggcgcag | 60 |
| gcgctcacct | ccctcctcct | ccgcggcatc | cccaatcgac cagctggctc ccctgcctcc | 120 |
| tccgcgattt | tgatcctaat | cacccatgtc | tgctgaagtc agcgaggaat atccttattt | 180 |
| cctctcctgc | tacttctggt | tcatatattg | cataaaattc cgagatttca cttgatacaa | 240 |
| gtggatcacc | tggagttttg | tgctaatact | tcctatcatg tgaatcagtt gtagttagca | 300 |
| taattggcaa | gactcaagtt | ttctctcatc | tgggttcaga acatttgtc ggttgagtgc | 360 |
| tcgatctaaa | ctctgcttga | gtcttgccga | agattgtttc tcaacaatca cgtcttctgt | 420 |
| tctctctgag | gttggaccaa | tctcccttt | ggtctgatca acctcctgat ctcccttaag | 480 |
| tgaaccgtcc | tgctgtgttc | acgcaataca | atcttctgaa gtcctctctt gttccttctg | 540 |
| tgctcaaaca | tcaaaagcag | ctctctccta | agttctcttg attgtttgtg ctcctaaatt | 600 |
| ctgttgtttg | agcactcaaa | catttcccct | actggtcaat cttagatcac ttgttgatta | 660 |
| ttggtattgg | cattatttgg | tgaagcattt | ctgcttgtac cttaaacaaa ggtctctgtt | 720 |
| gtcttattgg | tgctgaaggc | aagatataca | ctgcagtgat ggctcaaact tgcttgccac | 780 |
| ctggcttttcg | ttttcatcca | acagatgttg | aacttgtttc atactatttg aaaaggaaga | 840 |
| ttatgggaaa | gaagcctctt | attcaagcta | tatcagatgt tgaactgtat aaatttgctc | 900 |
| cctgggatct | tcctgctcaa | tcctgtctcc | agagcagaga tcttgaatgg ttcttctttt | 960 |
| gcccacgaga | caagaaatat | cctaatgggt | ctaggacaaa tcgttccaca ccaaatggtt | 1020 |
| actggaaaac | aagtgggaaa | gatagaacga | ttgagcttaa ctctcgcatt gttgggtcaa | 1080 |
| agaaaacact | gattttttcat | gaaggcaaag | cacctaaagg caacaggact gattgggtga | 1140 |
| tgtacgaata | caaaatggaa | gacaatcaat | tggtctctgc tggtttctca aaggatgatt | 1200 |
| ttgtcctctg | caaaattttc | aagaaaagtg | gccttggtcc aaggattggg gagcaatatg | 1260 |
| gggctccatt | taatgaagaa | gaatgggagc | atgcagatgc tgaaatgttt cccttgctgc | 1320 |
| caaatgttga | aacttctgtg | tttccattgc | tgccctcttc agaggtagta aattctactg | 1380 |
| atgatacacg | tgttcagcct | tctgttgctg | ccagagctat tgaggaacta cctgtgcagc | 1440 |
| atttacctca | tgtatgtgct | gggaatggat | caacatatca aaatattact gttactggtg | 1500 |
| aaagtgctct | catggaactg | ccttcccagc | actctgttga atctattggt gatgaggtag | 1560 |
| tttctgtgga | caactgttct | aatgtggtca | ataatgcaga cagtcctgta attgaggggc | 1620 |
| ttgtattgga | ggaactttct | aggtttttaa | ctgattctcc tcatcatggc aaccctgttg | 1680 |
| gggagcactc | tggtctccca | ccaatgtctg | aggctgaagc tcatgctttt gaggttagca | 1740 |
| caaatgatct | gtacaatgaa | attgcagggc | ttgctgaatt gggtgtgcca aatggtgatg | 1800 |
| gattttctcc | gtccaatgct | ggtgttactg | aacaacagcc cacatacttt ggagttccta | 1860 |
| acagtgaaaa | ttatgtaaat | atggatgata | tctttgctcc agacacaaga ttatcctatg | 1920 |

```
catatccttt gccaaacaac caattttggc attatcccat ggatcagttc acatacagta   1980
ctactctatc tgctgccttt ccatctggtg actcgcgtcc aactatgcgc attgttgatg   2040
atttacctgc tgctgctaat aacggtggct ttgcttcaaa acccagcatg cagttcccac   2100
tgtcataact aagtccagaa ccgttctaga ggactctgat actgatgacc tagtgggatt   2160
ccatatgctg gcagtactgc gcaacagatg tgtcttcatg ccacctgctg ccgctccga   2220 gctaagccaa acctcgctga atctttctcg tggactgttg ctggatttac cagtgctcga   2280
actggtggtc actgcaagca ttgtgaggcc aacaatgtac attgttttga aggtttggcc   2340
tagttctcga tggcgatgct ctatgatccg aacttgtcta gcctggcgcg ctactgagga   2400
tcagatattc gctttgtgtt accttattta cttgctgctg aataaagttt gtttatcaaa   2460
ctagtgtata ttgtgttatg actgcactta aaccttatgt aagtttgcat ggtttggcct   2520
actatttact tgctattaat cttctcctaa gttcgttgtt ttggc                   2565
```

<210> SEQ ID NO 7
<211> LENGTH: 431
<212> TYPE: PRT
<213> ORGANISM: Hordeum vulgare

<400> SEQUENCE: 7

```
Met Ala Gln Thr Cys Leu Pro Pro Gly Phe Arg Phe His Pro Thr Asp
1               5                   10                  15

Val Glu Leu Val Ser Tyr Tyr Leu Lys Arg Lys Ile Met Gly Lys Lys
            20                  25                  30

Leu Phe Val Gln Ala Ile Ser Glu Val Glu Leu Tyr Lys Phe Ala Pro
        35                  40                  45

Trp Asp Leu Pro Asp Lys Ser Cys Leu Gln Ser Lys Asp Leu Glu Trp
    50                  55                  60

Phe Phe Phe Cys Pro Arg Asp Lys Lys Tyr Pro Lys Gly Ser Arg Thr
65                  70                  75                  80

Asn Arg Ala Thr Pro Asn Gly Tyr Trp Lys Thr Ser Gly Lys Asp Arg
                85                  90                  95

Thr Ile Glu Leu Asn Ser Arg Ile Val Gly Leu Lys Lys Thr Leu Ile
            100                 105                 110

Phe His Glu Gly Lys Ala Pro Lys Gly Asn Arg Thr Asp Trp Val Met
        115                 120                 125

Tyr Glu Tyr Lys Met Glu Asp Glu Thr Leu Asp Ala Ala Gly Phe Ser
    130                 135                 140

Lys Asp Ala Tyr Val Leu Cys Lys Ile Phe Lys Lys Ser Gly Leu Gly
145                 150                 155                 160

Pro Arg Ile Gly Glu Gln Tyr Gly Ala Pro Phe Asp Glu Asn Glu Trp
                165                 170                 175

Glu Asn Leu Asp Val Gly Ser Ser Ile Phe Ser Phe Ala Pro Ser Ser
            180                 185                 190

Gly Val Glu Asp Pro Gln Val Glu Ser Ser Ala Leu Ala Thr Ala Val
        195                 200                 205

Ile Gln Glu Pro Phe Ala Pro Gln Gln Ser Val Gln Phe Ser Glu His
    210                 215                 220

Val Asn Ile Cys Ser Asn Glu Asp Asn Asn Ala Pro Glu Ile Asp
225                 230                 235                 240

Gly Ile Trp Leu Glu Glu Leu Ala Met Phe Leu Asn Asp Ser Pro Asn
                245                 250                 255

His Asp Ile Ala Leu Pro Glu Asn Ser Gly Leu Pro Pro Met Ser Glu
            260                 265                 270
```

Leu Glu Ala Gln Ala Phe Glu Met Asn Thr Ala Glu Leu Tyr Asp Gln
    275                 280                 285

Leu Ala Gly Leu Ala Gln Ser Gly Asp Met Ser Asn Val Asn Phe Pro
    290                 295                 300

Ala Ala Asp Val Gly Val Thr Glu Asn Asp Phe Gln Gln Ser Asn Ser
305                 310                 315                 320

Gly Phe Ala Met Asp Asp Tyr Ile Glu Leu Asp Leu Phe Ala
                325                 330                 335

Pro Gly Glu Thr Phe Ser Tyr Asp Phe Ser Gly Glu Thr Phe Ser Tyr
                340                 345                 350

Asp Leu Thr Gly Gly Thr Phe Ser Tyr Asp Leu Ser Val Pro Asn Asn
                355                 360                 365

Gln Phe Leu Gln Tyr Pro Leu Asp Gln Ser Thr Asn Gly Ser His Tyr
    370                 375                 380

Gly Asp Gly Ala Thr Gln Ser Thr Phe Glu Ala Ser Gly Ser Leu Pro
385                 390                 395                 400

Pro Met Pro Ser Thr Phe Asp Asp Met Pro Ser Val Ser Asn Lys Pro
                405                 410                 415

Ala Asn Ser Asn Cys Leu Asn Pro Thr Met Glu Asp Pro Phe Ser
                420                 425                 430

<210> SEQ ID NO 8
<211> LENGTH: 1350
<212> TYPE: DNA
<213> ORGANISM: Hordeum vulgare

<400> SEQUENCE: 8
atggctcaaa cttgcttgcc acctggcttt cgttttcatc aacagatgt tgaacttgtt      60 tcatactatt tgaaaggaa gattatggga agaagcctc ttattcaagc tatatcagat     120
gttgaactgt ataaatttgc tccctgggat cttcctgctc aatcctgtct ccagagcaga     180
gatcttgaat ggttcttctt tgcccacga gacaagaaat atcctaatgg gtctaggaca     240
aatcgttcca caccaaatgg ttactggaaa acaagtggga agatagaac gattgagctt     300 aactctcgca ttgttgggtc aaagaaaaca ctgattttc atgaaggcaa agcacctaaa     360
ggcaacagga ctgattgggt gatgtacgaa tacaaatgg aagacaatca attggtctct     420
gctggtttct caaggatga ttttgtcctc tgcaaaattt tcaagaaaag tggccttggt     480
ccaaggattg gggagcaata tggggctcca tttaatgaag aagaatggga gcatgcagat     540
gctgaaatgt ttcccttgct gccaaatgtt gaaacttctg tgtttccatt gctgccctct     600
tcagaggtag taaattctac tgatgataca cgtgttcagc cttctgttgc tgccagagct     660
attgaggaac tacctgtgca gcatttacct catgtatgtg ctgggaatgg atcaacatat     720
caaaatatta ctgttactgg tgaaagtgct ctcatggaac tgccttccca gcactctgtt     780
gaatctattg gtgatgaggt agtttctgtg acaactgtt ctaatgtggt caataatgca     840
gacagtcctg taattgaggg gcttgtattg gaggaacttt ctaggttttt aactgattct     900
cctcatcatg gcaaccctgt tggggagcac tctggtctcc caccaatgtc tgaggctgaa     960
gctcatgctt ttgaggttag cacaaatgat ctgtacaatg aaattgcagg gcttgctgaa    1020
ttgggtgtgc caaatggtga tggattttct ccgtccaatg ctggtgttac tgaacaacag    1080
cccacatact ttggagttcc taacagtgaa aattatgtaa atatggatga tatctttgct    1140
ccagacacaa gattatccta tgcatatcct ttgccaaaca accaattttg gcattatccc    1200
atggatcagt tcacatacag tactactcta tctgctgcct ttccatctgg tgactcgcgt    1260

```
ccaactatgc gcattgttga tgatttacct gctgctgcta ataacggtgg ctttgcttca    1320
aaacccagca tgcagttccc actgtcataa                                     1350

<210> SEQ ID NO 9
<211> LENGTH: 1798
<212> TYPE: DNA
<213> ORGANISM: Hordeum vulgare

<400> SEQUENCE: 9
cactgcagtg atggctcaaa cttgcctgcc acctggcttt cgtttccatc caacagatgt      60
tgagcttgtt tcttactact tgaaaaggaa gattatgggg aagaaacttt ttgttcaagc     120
tatctcagag gttgagctgt acaaatttgc tccttgggac cttcctgata aatcctgtct     180
ccagagcaaa gatcttgagt ggttcttctt ttgcccccgt gacaagaaat atcctaaagg     240
gtctaggacg aaccgtgcca caccaaatgg ttattggaaa acaagtggaa aagacagaac     300
aattgagctg aactctcgca ttgttgggtt gaagaagaca ttgattttc atgaaggcaa      360 ggcacccaaa ggcaacagga cagattgggt gatgtatgaa tacaaaatgg aagatgaaac     420
tttggatgct gctggtttct caaggatgc ttatgtgctc tgcaagatat ttaaaaagag      480
tgggcttggc ccaaggattg gtgagcaata tggggctcct tttgatgaaa atgaatggga     540
gaatttggat gttggaagtt ctatcttctc ttttgcaccc tcgtccggtg tagaggatcc     600
acaagttgaa agttctgcct tggctactgc agttattcag gaaccattcg cgcctcagca     660
gtctgttcaa ttttctgaac atgttaatat ctgttctaat gaggacaata atgcgcctcc     720
tgaaattgat ggaatttggt tggaagaact tgcaatgttt ttgaatgatt ctcccaacca     780
tgacatagct ttgccagaga attctggtct ccctccaatg tctgagcttg aggctcaagc     840
ttttgagatg aatactgctg agctctatga tcaattagca ggacttgccc agtcagggga     900
tatgtctaat gtaaacttcc ctgctgccga cgtgggtgtt actgaaaacg atttccagca     960
atcaaactct ggatttgcta tggatgatga ttatatagag ctggatgatc tgtttgctcc    1020
tggggaaacc ttctcttatg attttctgg tgaaaccttc tcctatgatt tgactggtgg     1080
aaccttctcc tatgatttgt ctgtgccaaa caatcagttt ttgcagtacc cattggatca    1140
atcaactaat ggcagtcact acggtgatgg tgctactcaa tcaacttttg aagcaagtgg    1200
atcgcttcca ccaatgccta gcacttttga tgacatgcct tctgtttcca ataagcctgc    1260
aaactccaat tgcttgaacc caaccatgga agacccattc tcttagacag caacttttga    1320
ggtataagtc tgttatcttt ggtcattgct cttggaagtt gctgctgttt ctggtttggt    1380
tgtccaatca ttgtctgatg cgactattga tggaccttgg atgttggtcc gtgctgtaaa    1440
tggcccaaca gtggtgtttg catcatggca tggctgctgc tcttttgaag aagccggaac    1500
ttggttgtgt ctcaatcacg agcacaatac tggacaagcg accgagctta ctgcttttct    1560
gcggagaaac tgttttctgc tggtttggaa gatgtcttat atggatggat atgctgccgt    1620
ccaccgtaga tctttctgta ataacttgat gacaacttcg tagcttaagt ccatctttta    1680
tctatatatt ctgtcaaaaa tacttttgaa ccatcttcat tacaaaaaaa aaaaaaaaa     1740 aaaaaaaaa aaaaaaaaa aaaaaaaaa aaaaaaaaa aaaaaaaaa aaaaagg            1798

<210> SEQ ID NO 10
<211> LENGTH: 113
<212> TYPE: PRT
<213> ORGANISM: Hordeum vulgare

<400> SEQUENCE: 10
```

Lys Phe Asn Ser Gly Glu Tyr Gln Val Ile Leu Arg Lys Glu Leu Thr
1               5                   10                  15

Lys Ser Asp Val Ala Asn Val Gly Arg Ile Val Leu Pro Lys Lys Asp
                20                  25                  30

Ala Glu Ala Ser Leu Pro Pro Leu Cys Glu Arg Asp Pro Val Ile Leu
            35                  40                  45

Gln Met Asp Asp Met Val Leu Pro Val Thr Trp Lys Phe Lys Tyr Arg
50                  55                  60

Phe Trp Pro Asn Asn Lys Ser Arg Met Tyr Ile Leu Asp Ser Thr Ser
65                  70                  75                  80

Glu Phe Val Lys Thr His Gly Leu Gln Ala Gly Asp Ala Leu Ile Ile
                85                  90                  95

Tyr Lys Asn Pro Val Pro Gly Lys Tyr Ile Val Arg Gly Glu Lys Ala
            100                 105                 110

Ile

<210> SEQ ID NO 11
<211> LENGTH: 339
<212> TYPE: DNA
<213> ORGANISM: Hordeum vulgare

<400> SEQUENCE: 11
aaattcaact ctggagaata ccaagttatc ttgcgcaagg aattgacaaa gagtgatgtt      60
gcgaatgtcg gaagaattgt gttacccaag aaggatgcag aagctagtct tccaccattg     120
tgcgaaaggg atcctgtgat actgcagatg gatgacatgg tcctcccggt tacgtggaaa    180
tttaagtaca ggttctggcc aaacaacaaa agcagaatgt acatcctgga ttctacaagt    240
gaatttgtga agacacatgg tcttcaggca ggggacgcac tcattatcta caaaaatcct    300
gtgcctggaa aatatattgt ccgaggggag aaggccatt                            339

<210> SEQ ID NO 12
<211> LENGTH: 1565
<212> TYPE: DNA
<213> ORGANISM: Hordeum vulgare

<400> SEQUENCE: 12 cccccgcct ctgcctgccc gggttaccct accacccctc ctcccaccca tagccgaggc       60
aggccagagg agagagagag agagaaagag aagccagggc ttggctggta gatgcgcgag     120
tagcggtgcc tgccaaggcc aaggggaatg ggaggcgacg gcaggcccgg cgacggcggc    180
ggcggcggcg ccggccaccc gcaccagttc cagtaccaag ccctactcgc cgccgtgcac    240
acgcagaacc caaccacaa ccacaaccac aaccacaacc acaacctccc ctttcccctt      300
cctcccctca atggacctgg acctgatgca tccacacaca atgctgctcg ccagcctccg    360
accccaaggg ggtttgctga ttggagtgcg ctctacgagcg ccttcacgtc ccttgctgtg   420
cagagcactc cttccacagc tactgccaat gcataccatt acagcctatc tccttgctat    480
gcattctgga cccattacat gcttaacaag aatgcatata gctactatcc tgcacctaat    540
caggagcaca cccaccctttt cagccttgat aacaatcagg ctaaagatcc aggttctata   600
cccaacttcg ggattgagtc atttaataca acatccctgg caccaagcat gtctgctcat    660
atgcctccca tggaaggacc cctatctaca aaggaacctg aggcttcaga ggacatgcct    720
gctagagtag ttgcaattaa ggacgaaagg gatgccagaa atggtattga acttaaatgt    780
gaaacggttg acgctcttcc agagttgaag caaggtcatg aaagttgtgc caccaaattc    840

```
aactctggag aataccaagt tatcttgcgc aaggaattga caaagagtga tgttgcgaat    900
gtcggaagaa ttgtgttacc caagaaggat gcagaagcta gtcttccacc attgtgcgaa    960
agggatcctg tgatactgca gatggatgac atggtcctcc cggttacgtg gaaatttaag   1020
tacaggttct ggccaaacaa caaaagcaga atgtacatcc tggattctac aagtgaattt   1080
gtgaagacac atggtcttca ggcaggggac gcactcatta tctacaaaaa tcctgtgcct   1140
ggaaaatata ttgtccgagg ggagaaggcc attcagcaga caaattagag catgtggatg   1200
gatgtgattg cgaccgcgtc agtgaggaca tttcaagcga ggaatgtggg ttcgcaatcc   1260
aagaggactt gacggagttg agctggctga ggaattcatg acagtctgac ttgttaactg   1320
gggagtgaac ggaaaaagat tggacgtgcg tgctgccaaa gagtttgctt ttacagcgcg   1380
acatccaagt tgaggagacc cttttgccta ttttttttgtt cttctttctt tctaattgag   1440
ttgcatttgg aaactttgag ttctaccttc tccttcagaa tagcatttgc ggttctgtaa   1500
atattctcgg atccataaga taaatgaagt ggcgtggact ttggacgtaa aaaaaaaaa   1560
aaaaa                                                               1565

<210> SEQ ID NO 13
<211> LENGTH: 113
<212> TYPE: PRT
<213> ORGANISM: Triticum aestivum

<400> SEQUENCE: 13

Lys Phe Asn Ser Gly Glu Tyr Gln Val Ile Leu Arg Lys Glu Leu Thr
1               5                   10                  15

Lys Ser Asp Val Ala Asn Val Gly Arg Ile Val Leu Pro Lys Lys Asp
            20                  25                  30

Ala Glu Ala Ser Leu Pro Pro Leu Cys Glu Arg Asp Pro Val Ile Leu
        35                  40                  45

Gln Met Asp Asp Met Val Leu Pro Ile Thr Trp Lys Phe Lys Tyr Arg
    50                  55                  60

Phe Trp Pro Asn Asn Lys Ser Arg Met Tyr Ile Leu Asp Ser Thr Ser
65                  70                  75                  80

Glu Phe Val Lys Thr His Gly Leu Gln Ala Gly Asp Ala Leu Ile Ile
                85                  90                  95

Tyr Lys Asn Pro Val Pro Gly Lys Tyr Ile Val Arg Gly Glu Lys Ala
            100                 105                 110

Ile

<210> SEQ ID NO 14
<211> LENGTH: 339
<212> TYPE: DNA
<213> ORGANISM: Triticum aestivum

<400> SEQUENCE: 14
aaattcaact ctggagaata ccaagttatt ttgcgcaagg aattgacaaa gagtgatgtt     60
gcaaatgtag gaagaattgt gttacccaag aaggatgcag aagctagtct tccaccattg    120
tgtgaaaggg atcctgtgat actgcagatg gatgacatgt gctcccgat acgtggaaa     180
tttaagtaca ggttctggcc aaacaacaaa agcagaatgt acatcctgga ttctacaagt    240
gaatttgtga agacacatgg tcttcaggca ggggacgcac tcattatcta caaaaatcct    300
gtgcctggca aatatattgt ccgaggggag aaggccatt                           339

<210> SEQ ID NO 15
<211> LENGTH: 518
```

```
<212> TYPE: DNA
<213> ORGANISM: Triticum aestivum

<400> SEQUENCE: 15
tccagagttg aagcaaggtc atgaaagttg tgccagtaaa ttcaactctg gagaatacca      60
agttattttg cgcaaggaat tgacaaagag tgatgttgca atgtaggaa gaattgtgtt     120
acccaagaag gatgcagaag ctagtcttcc accattgtgt gaaagggatc ctgtgatact     180
gcagatggat gacatggtgc tcccgattac gtggaaattt aagtacaggt tctggccaaa     240
caacaaaagc agaatgtaca tcctggattc tacaagtgaa tttgtgaaga cacatggtct     300
tcaggcaggg gacgcactca ttatctacaa aaatcctgtg cctggcaaat atattgtccg     360
aggggagaag gccattcagc agacaaatta gaggatgtgg atggtgattg cgaccgcgtc     420
agtgaggaca tttcaagcga gggatgtggg ttcgcaatcc aagggaactc ggagttgagc     480
tggctgggga attcatgaca gtctgacttg ttaactgg                             518

<210> SEQ ID NO 16
<211> LENGTH: 113
<212> TYPE: PRT
<213> ORGANISM: Zea Mays

<400> SEQUENCE: 16

Lys Phe Asn Ser Gly Glu Tyr Gln Val Ile Leu Arg Lys Glu Leu Thr
1               5                  10                  15

Lys Ser Asp Val Ala Asn Ser Gly Arg Ile Val Leu Pro Lys Lys Asp
            20                  25                  30

Ala Glu Ala Gly Leu Pro Pro Leu Val Gln Gly Asp Pro Leu Ile Leu
        35                  40                  45

Gln Met Asp Asp Met Val Leu Pro Ile Ile Trp Lys Phe Lys Tyr Arg
    50                  55                  60

Phe Trp Pro Asn Asn Lys Ser Arg Met Tyr Ile Leu Glu Ala Ala Gly
65                  70                  75                  80

Glu Phe Val Lys Thr His Gly Leu Gln Ala Gly Asp Ala Leu Ile Ile
                85                  90                  95

Tyr Lys Asn Ser Val Pro Gly Lys Phe Ile Ile Arg Gly Glu Lys Ser
            100                 105                 110

Ile

<210> SEQ ID NO 17
<211> LENGTH: 339
<212> TYPE: DNA
<213> ORGANISM: Zea mays

<400> SEQUENCE: 17
aagttcaact ctggagagta ccaagtcatt ttgcgcaagg agttgacaaa gagtgatgtc      60
gcaaattccg gacgaattgt gcttcccaag aaggatgctg aggctggtct tccaccattg     120
gtgcaagggg atcctctgat actgcagatg gatgacatgg tgcttccaat tatatggaaa     180
tttaagtata gattttggcc aaacaacaaa agcagaatgt atatcttgga agctgcaggt     240
gaattcgtga agacacatgg ccttcaggca ggggatgcgc tcattatcta caaaaactcc     300
gtgcctggca aatttattat ccgtggggag aagtccatt                            339

<210> SEQ ID NO 18
<211> LENGTH: 867
<212> TYPE: DNA
<213> ORGANISM: Zea Mays
```

<400> SEQUENCE: 18

```
acscccatgg aaggatctat atctgccaaa gaacccgaga attcagagga tttgcctgca      60
atagttagga gcagtgatga aatggacact agaaatcagt ggcaaagttc atcgtgacac     120
agttggcact cttcctgagt cgaagcagag ccatgaaagt tgtgcttccg tgaataacaa     180
gttcaactct ggagagtacc aagtcatttt gcgcaaggag ttgacaaaga gtgatgtcgc     240
aaattccgga cgaattgtgc ttcccaagaa ggatgctgag gctggtcttc caccattggt     300
gcaaggggat cctctgatac tgcagatgga tgacatggtg cttccaatta tatggaaatt     360
taagtataga ttttggccaa acaacaaaag cagaatgtat atcttggaag ctgcaggtga     420
attcgtgaag acacatggcc ttcaggcagg ggatgcgctc attatctaca aaaactccgt     480
gcctggcaaa tttattatcc gtggggagaa gtccattcag cagacaaacc cctagacaca     540
atttgatgtg actgtgcacc atcagatatg gcgtccgagg atacaccata tgttcacgtt     600
ccagttgtta tcgactttta taatgtctca ccgtcacact gagataagtc gaaaaaggag     660
atacaccgcg tggatggaga aaaagagaag aaattttggg agacattgga agtgctgcca     720
gtgaggctac gtctaagctc agaacaaatg gtttatgttt tttcccctaa ttcggtcgta     780
tttggatgct tgagtcctgc attgcatgat gaagaacatt ctcaatctct cttttttttgt    840
aaatatttta attcaggatc tataagg                                         867
```

<210> SEQ ID NO 19
<211> LENGTH: 113
<212> TYPE: PRT
<213> ORGANISM: Sorghum bicolor

<400> SEQUENCE: 19

```
Lys Phe Asn Ser Gly Glu Tyr Gln Val Ile Leu Arg Lys Glu Leu Thr
 1               5                  10                  15
Lys Ser Asp Val Ala Asn Ser Gly Arg Ile Val Leu Pro Lys Lys Asp
            20                  25                  30
Ala Glu Ala Gly Leu Pro Pro Leu Val Gln Gly Asp Pro Leu Ile Leu
        35                  40                  45
Gln Met Asp Asp Met Val Leu Pro Ile Ile Trp Lys Phe Lys Tyr Arg
    50                  55                  60
Phe Trp Pro Asn Asn Lys Ser Arg Met Tyr Ile Leu Glu Ala Ala Gly
65                  70                  75                  80
Glu Phe Val Lys Thr His Gly Leu Gln Ala Gly Asp Ala Leu Ile Ile
                85                  90                  95
Tyr Lys Asn Ser Val Pro Gly Lys Phe Ile Ile Arg Gly Glu Lys Ser
               100                 105                 110
Ile
```

<210> SEQ ID NO 20
<211> LENGTH: 339
<212> TYPE: DNA
<213> ORGANISM: Sorghum bicolor

<400> SEQUENCE: 20

```
aagttcaact ctggagagta ccaagtcatt ttgcgcaagg agttgacaaa gagtgatgtc      60
gcaaattctg gcgaattgt gcttcccaag aaggatgctg aggctggtct tccaccattg     120
gtgcaagggg atcctctgat actgcagatg gatgacatgg tgcttccgat tatatggaaa     180
tttaagtata gattttggcc aaacaacaaa agcagaatgt atattctgga agctgcaggt     240
gaattcgtga agacacatgg ccttcaggca ggggatgcac tcattatcta caaaaactcc     300
```

```
gtgcctggca aatttattat tcgtggggag aagtccatt                     339
```

```
<210> SEQ ID NO 21
<211> LENGTH: 460
<212> TYPE: DNA
<213> ORGANISM: Sorghum bicolor

<400> SEQUENCE: 21
gcacgaggat gactttcaga agttcaactc tggagagtac caagtcattt tgcgcaagga   60
gttgacaaag agtgatgtcg caaattctgg gcgaattgtg cttcccaaga aggatgctga  120
ggctggtctt ccaccattgg tgcaagggga tcctctgata ctgcagatgg atgacatggt  180
gcttccgatt atatggaaat ttaagtatag attttggcca acaacaaaa gcagaatgta   240 tattctggaa gctgcaggtg aattcgtgaa gacacatggc cttcaggcag gggatgcact  300
cattatctac aaaaactccg tgcctggcaa atttattatt cgtggggaga agtccattca  360
gcagacaaac ccctagacac aatttgatgt gactggcacc atcagatatg gcgttcaagg  420
atacaccata agttcacaat caaagggtta ttgacttatg                        460
```

```
<210> SEQ ID NO 22
<211> LENGTH: 113
<212> TYPE: PRT
<213> ORGANISM: Saccharum officinarum
<220> FEATURE:
<221> NAME/KEY: misc_feature
<222> LOCATION: (89)..(89)
<223> OTHER INFORMATION: Xaa stands for any amino acid

<400> SEQUENCE: 22

Lys Phe Asn Ser Gly Glu Tyr Gln Val Ile Leu Arg Lys Glu Leu Thr
1               5                   10                  15

Lys Ser Asp Val Ala Asn Ser Gly Arg Ile Val Leu Pro Lys Lys Asp
            20                  25                  30

Ala Glu Ala Gly Leu Pro Pro Leu Val Gln Gly Asp Pro Leu Ile Leu
        35                  40                  45

Gln Met Asp Asp Met Val Leu Pro Ile Ile Trp Lys Phe Lys Tyr Arg
    50                  55                  60

Phe Trp Pro Asn Asn Lys Ser Arg Met Tyr Ile Leu Glu Ala Ala Gly
65                  70                  75                  80

Glu Phe Val Lys Thr His Gly Leu Xaa Ala Gly Asp Ala Leu Ile Ile
                85                  90                  95

Tyr Lys Asn Ser Glu Pro Gly Lys Phe Ile Ile Arg Gly Glu Lys Ser
            100                 105                 110

Ile
```

```
<210> SEQ ID NO 23
<211> LENGTH: 339
<212> TYPE: DNA
<213> ORGANISM: Saccharum officinarum
<220> FEATURE:
<221> NAME/KEY: misc_feature
<222> LOCATION: (267)..(267)
<223> OTHER INFORMATION: n stands for any base

<400> SEQUENCE: 23
aagttcaact ctggagagta ccaagtcatt ttgcgcaagg agttgacaaa gagtgatgtc   60
gcaaattccg ggcgaattgt gcttcccaag aaggatgctg aggctggtct tccaccattg  120
gtgcaagggg atcctctgat actgcagatg gatgacatgg tgcttccgat tatatggaaa  180
```

```
tttaagtata gattttggcc aaacaacaaa agcagaatgt atattctgga agctgcaggt      240
gaattcgtga agacacatgg ccttcangca ggggatgcac tcatcatcta caaaaactcc      300
gagcctggca aatttattat ccgtggggag aagtccatt                             339
```

<210> SEQ ID NO 24
<211> LENGTH: 687
<212> TYPE: DNA
<213> ORGANISM: Saccharum officinarum
<220> FEATURE:
<221> NAME/KEY: misc_feature
<222> LOCATION: (569)..(569)
<223> OTHER INFORMATION: n stands for any base

<400> SEQUENCE: 24

```
gcacgaggaa tccccaccca ttgcgccata cccacatccc ggataaggat tcaggttgtg       60
catccagcct tggatttgac tctttcacta caatgtccct tggaccaaat atttgtgccc      120
acatgacgcc catggaagga tctatatctg ccaaagaacc tgagaattca gaggatttgc      180
ctgcagtagt tagaagcagt gatgaaatgg acactagaaa cagtggcgaa gttcatcatg      240
acacagttgg cactcttcct gagtcgaagc agagccatga agttgcgct tccatgagta      300 acaagttcaa ctctggagag taccaagtca ttttgcgcaa ggagttgaca agagtgatg      360 tcgcaaattc cgggcgaatt gtgcttccca gaaggatgc tgaggctggt cttccaccat       420
tggtgcaagg ggatcctctg atactgcaga tggatgacat ggtgcttccg attatatgga      480
aatttaagta tagatttttgg ccaaacaaca aaagcagaat gtatattctg aagctgcag      540 gtgaattcgt gaagacacat ggccttcang caggggatgc actcatcatc tacaaaaact      600
ccgagcctgg caaatttatt atccgtgggg agaagtccat tcagcagaca aaccctagac      660
acaatttgat gtgactgtgg caccatt                                          687
```

<210> SEQ ID NO 25
<211> LENGTH: 113
<212> TYPE: PRT
<213> ORGANISM: Hordeum vulgare

<400> SEQUENCE: 25

```
Arg Phe Asn Cys Lys Asp Tyr Tyr Met Ile Val Trp Lys Glu Leu Thr
1               5                   10                  15

Asn Ser Asp Val Gly Asn Ile Gly Arg Ile Val Leu Pro Lys Arg Asp
            20                  25                  30

Ala Glu Ala Asn Leu Pro Ala Leu Leu Glu Arg Asp Gly Leu Ile Leu
        35                  40                  45

Lys Met Asp Asp Leu Lys Leu Pro Val Thr Trp Asn Phe Lys Phe Arg
    50                  55                  60

Phe Trp Pro Asn Asn Lys Ser Arg Met Tyr Val Leu Glu Ser Thr Gly
65                  70                  75                  80

Glu Phe Ser Lys Asn His Asn Leu Glu Pro Gln Asp Thr Phe Ile Ile
                85                  90                  95

Tyr Lys Ser Leu Glu Ser Gly Lys Phe Leu Val Arg Ala Glu Lys Val
            100                 105                 110

Thr
```

<210> SEQ ID NO 26
<211> LENGTH: 339
<212> TYPE: DNA
<213> ORGANISM: Hordeum vulgare

<400> SEQUENCE: 26

```
aggttcaact gtaaagacta ctatatgatt gtgtggaagg agttgaccaa cagtgatgtt      60
ggaaatattg gaagaattgt actgccaaag agggatgcag aggctaacct tccagctttg     120
cttgaaaggg atggcctgat actcaagatg gatgacttga agcttcctgt tacatggaac     180
tttaagttca ggttctggcc taacaacaag agcagaatgt atgtcttgga aagtactgga     240
gaattttcaa agaaccataa tctagagcca caagacacct tcatcatcta caaaagcctg     300
gagtccggca aatttcttgt ccgtgcggag aaggtgacc                            339

<210> SEQ ID NO 27
<211> LENGTH: 602
<212> TYPE: DNA
<213> ORGANISM: Hordeum vulgare

<400> SEQUENCE: 27
cggcacgagg gatcaaccaa tatctccggc gtcaaacaat cacttctcct ccacaattat      60
tagacgaggc cacatacacc aaaagggcga agaggaacac catgcgcacc cagaagggga     120
ggaattcaga ggacccgcct gagatggaaa gtgaaaacag tgatgtacta gatcaccca     180 tgctagatga gaatcacaac ttgaatcagg gccaggaaat tttcactact aggttcaact     240
gtaaagacta ctatatgatt gtgtggaagg agttgaccaa cagtgatgtt ggaaatattg     300
gaagaattgt actgccaaag agggatgcag aggctaacct tccagctttg cttgaaaggg     360
atggcctgat actcaagatg gatgacttga agcttcctgt tacatggaac tttaagttca     420
ggttctggcc taacaacaag agcagaatgt atgtcttgga aagtactgga gaattttcaa     480
agaaccataa tctagagcca caagacacct tcatcatcta caaaagcctg gagtccggca     540
aatttcttgt ccgtgcggag aaggtgaccg ggcagtgcgc taccttactc tgtccggaat     600
gc                                                                   602

<210> SEQ ID NO 28
<211> LENGTH: 113
<212> TYPE: PRT
<213> ORGANISM: Oryza sativa

<400> SEQUENCE: 28

Arg Phe Asn Cys Arg Glu Tyr Arg Val Ile Leu Arg Lys Glu Leu Thr
1               5                   10                  15

Asn Ser Asp Val Gly Asn Ile Gly Arg Ile Val Met Pro Lys Arg Asp
            20                  25                  30

Ala Glu Ala His Leu Pro Ala Leu His Gln Arg Glu Gly Val Met Leu
        35                  40                  45

Lys Met Asp Asp Phe Lys Leu Glu Thr Thr Trp Asn Phe Lys Tyr Arg
    50                  55                  60

Phe Trp Pro Asn Asn Lys Ser Arg Met Tyr Val Leu Glu Ser Thr Gly
65                  70                  75                  80

Gly Phe Val Lys Gln His Gly Leu Gln Thr Gly Asp Ile Phe Ile Ile
                85                  90                  95

Tyr Lys Ser Ser Glu Ser Glu Lys Leu Val Val Arg Gly Glu Lys Ala
            100                 105                 110

Ile

<210> SEQ ID NO 29
<211> LENGTH: 339
<212> TYPE: DNA
<213> ORGANISM: Oryza sativa
```

```
<400> SEQUENCE: 29
agattcaact gtagagaata ccgtgttatc ttgcgcaagg agttgacaaa tagtgatgtt        60
ggtaatattg gaagaattgt gatgccaaag agggatgcag aggctcatct tccagcattg       120
catcaaaggg aagtgtgat  gctgaaaatg gatgacttca agcttgaaac tacttggaat       180
tttaagtaca ggttctggcc caacaacaag agcagaatgt atgtcttgga aagcacgggt       240
ggctttgtga agcagcatgg tctccagaca ggggacatat tcatcatcta caaaagctcg       300
gagtctgaga aattagttgt tcgtggggag aaggccatt                              339

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 30
atcaagcatg cttcttgc                                                      18

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 31 catgc                                                                     5

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 32
ttgaacggca agtttcacgc tgtcact                                            27

<210> SEQ ID NO 33
<211> LENGTH: 4
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 33 camg                                                                      4

<210> SEQ ID NO 34
<211> LENGTH: 7
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 34 camgttt                                                                   7
```

```
<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 35 camgyh                                                                     6

<210> SEQ ID NO 36
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 36 tccatgcat                                                                  9

<210> SEQ ID NO 37
<211> LENGTH: 6
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 37 catgca                                                                     6

<210> SEQ ID NO 38
<211> LENGTH: 102
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 38
gcagtcgaat tcgatatcaa gcatgcttct tgctgcccat caagcatgct tcttgctgcc         60
catcaagcat gcttcttgct gcccgtcgac tctagagcag tc                            102

<210> SEQ ID NO 39
<211> LENGTH: 130
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 39
aagcttgaat tcgatatctt gaacggcaag tttcacgctg tcactatcaa gcatgcttct         60
tgcttgaacg gcaagtttca cgctgtcact atcaagcatg cttcttgcac gcgtctcgag        120
tcgcgaatcg                                                               130

<210> SEQ ID NO 40
<211> LENGTH: 113
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 40
```
agcttgaatt cttgaacggc aagtttcacg ctgtcacttt gaacggcaag tttcacgctg        60
tcactttgaa cggcaagttt cacgctgtca ctctagagtc gacctcgagg cat              113

<210> SEQ ID NO 41
<211> LENGTH: 46
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 41
gagagtgggt tgaacggcaa gtttcacgct gtcactatcg tcctcg                      46

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 42
ggatccgtat ggacgcctcc gccggct                                           27

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 43
agatcttcag atgctaaccg ccatctggc                                         29

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 44
gaattcccgg ggatggggca aatggacgg                                         29

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 45
agatctctag ggatttgttg tctgctgatg                                        30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 46
gaattcccgg ggatggccga cacgagaggc t                                         31

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 47
agatcttcag gttttcttag tcagcaggct g                                         31

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 48
ggatccgtat ggccggggtc accagcaa                                             28

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 49
agatcttcac atgtgaggcc cagactttg                                            29

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 50
gaattcccgg ggatggcggg gatggctgc                                            29

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 51
ggatcctcaa gctaaagcag cagcagagt                                            29

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 52
gaattcagct cctacaccat gccgtcg                                              27

-continued

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 53
tctagatcag atgctaaccg ccatctgg                                     28

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 54
tctagagaat tccctgcgcc acacgacga                                    29

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 55
gtcgacgagc tcctagggat ttgttgtctg c                                 31

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 56
gaattcacgc catactcctt caatgcatgg                                   30

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 57
tctagatcag gttttcttag tcagcaggct g                                 31

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 58
ggatccatgg ccggggtcac cagcaa                                       26

```
<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 59
ggatcctcac atgtgaggcc cagactttg                                         29

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 60
gaattcccat ttcagcatgc acaaaggg                                          28

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 61
tctagatcag gttaattctt caggtgcaga gc                                     32

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 62
ggtaccatgg ctcaaacttg cttgcc                                            26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 63
gagctctgac agtgggaact gcatgc                                            26

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 64
ctcgagtcta gaatggctca aacttgcttg cc                                     32

<210> SEQ ID NO 65
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 65
ttaatctgca tgctcccatt cttc                                              24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 66
cacccagtcc tgtaattgag gggc                                              24

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 67
gtgggaactg catgctgggt                                                   20

<210> SEQ ID NO 68
<211> LENGTH: 1696
<212> TYPE: DNA
<213> ORGANISM: Hordeum vulgare

<400> SEQUENCE: 68
ggattgggga taaacacctc agcaaaatca ggattggtga cgaaattgaa gatgacctgt       60
ctgtttcttt gtacttaata aatcttcatg caaaccgtgt tgaaatagaa gacctgtgga      120
atcatggact gcggttttgg aggctaagac catcttagtt tttcaggttt acgttttgt       180 ttttcttgt tttttcatag attttctttg tttgtttctc catttcaccg ttttcgcat        240 tggttttcac ggtttttttt tctgtttttt atcttcttt gttcttgac agggttttct       300 ttttcttct ccttttttt ggttttcata tttcttctcc attctttgtt tggtttcctt       360
ttttattctt attttttgtt ttttcttacg tatgttttc ttttcaatct gaattttcat      420
gtacgttaaa acatttatt taataaaagg tcaacatttt ttgtatatat attcaacaat      480
gtccaaacgc ttatttaatt gcccaatatt ttaatactaa ttcaaaaaaa ttaaataatt     540
tttctattta tttctaaata ctcattcaac atttgtaata cttagccgac atttttaaa     600 tactggaact acattttca aatatttgat taacatttca taaatctta ttccaccattt    660 gttaatactt attaagcatt tgtaaataca tattcaacat ttttaatgtg tttttgtata    720
gtgtcttaaa aaatacttgt tttgtttaat attcaatagt aaaaggaac acaataata      780 aaagaaaaa catgaaaaaa gaaatacaat aaaacaggct tgtgattccc tcccgcgtgg     840
gacggcggtt cctacgagga ggtgttgggg caccccgggc aatcggaggt attctcttcg    900
tcacggttta aaaggcatgc ttggaaatta tctagaacct agatggttat tgattagtta    960
tgagatggac taaaaatag cagtcacact acgcatacat atagaagtag tataacagag    1020
tactataatt agctgctatg agtaatgaaa tgcaccctaa ataatcttgt ctatcatgga   1080
```

```
aatgcacgta aatttaaccg tgtcttctaa atagtgacgg aaggagcacc aaatacattg    1140
cagtggagtc tcgggccagt taactttgac cctcattgat aaaaatgaat aaataacttg    1200
gactatgact agcaaaacta gccggacaat ttgacctaaa caggctagct aggacccaat    1260
tacaaaagca acatggacta acttggactc cacacctacc cgaagtagca catggaaagg    1320
attaaccgac tcattctgga cttttataat ctaataatca accgagaggc catgcatccg    1380
tctagtatat aacagtatat ataataacaa tccatactag acgacgagga cgatttgaac    1440
ggcaagtttc acgctgtcac tcccactctc gctctcattt tattaatcac taacaaacgc    1500
atgatttgat cagacaccca aaataggaat aggagatgct atcatcaagc atgcttcttg    1560
ctgcccagag catcccacga ctacaaaaca cggctggccg gaggattata acacgatcga    1620
gcgaccaatc caagcaccta cgcactcttc tttgctctca tcctctagct agctaactag    1680
ctctcttgga tcatcc                                                     1696

<210> SEQ ID NO 69
<211> LENGTH: 18
<212> TYPE: DNA
<213> ORGANISM: Oryza sativa

<400> SEQUENCE: 69
atcaagcatg cttcttgc                                                     18

<210> SEQ ID NO 70
<211> LENGTH: 18
<212> TYPE: DNA
<213> ORGANISM: Oryza sativa

<400> SEQUENCE: 70
agcatgcatg gatcatgc                                                     18

<210> SEQ ID NO 71
<211> LENGTH: 18
<212> TYPE: DNA
<213> ORGANISM: Oryza sativa

<400> SEQUENCE: 71
tccatgcatg cataatgc                                                     18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 72
cgacctacgg cttcttgc                                                     18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 73
cgaaagcatg cttcttgc                                                     18

<210> SEQ ID NO 74
```

```
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 74
atccctcatg cttcttgc                                                18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 75
atcaagacgg cttcttgc                                                18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 76
atcaagcatt aggaggta                                                18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 77
atcaagcatt agtcttgc                                                18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 78
atcaagcatg ctgagtgc                                                18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 79
atcaagcatg cttctgta                                                18

<210> SEQ ID NO 80
<211> LENGTH: 18
<212> TYPE: DNA
```

```
<213> ORGANISM: Artificial Sequence
<220> FEATURE:
<223> OTHER INFORMATION: Description of Artificial Sequence:Artificially
      synthesized sequence

<400> SEQUENCE: 80
cgacctcatg cttaggta                                                       18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 81
cgacctcatg cggaggta                                                       18

<210> SEQ ID NO 82
<211> LENGTH: 9
<212> TYPE: DNA
<213> ORGANISM: Oryza sativa

<400> SEQUENCE: 82 ggcaagttt                                                                  9

<210> SEQ ID NO 83
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 83 tgcaagttt                                                                  9

<210> SEQ ID NO 84
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 84 gtcaagttt                                                                  9

<210> SEQ ID NO 85
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 85 ggaaagttt                                                                  9

<210> SEQ ID NO 86
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence
```

```
<400> SEQUENCE: 86 ggccagttt                                                            9

<210> SEQ ID NO 87
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 87 ggcacgttt                                                            9

<210> SEQ ID NO 88
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 88 ggcaatttt                                                            9

<210> SEQ ID NO 89
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 89 ggcaaggtt                                                            9

<210> SEQ ID NO 90
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 90 ggcaagtgt                                                            9

<210> SEQ ID NO 91
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 91 ggcaggttt                                                            9

<210> SEQ ID NO 92
<211> LENGTH: 9
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 92
```

-continued ggcaagttt    9

<210> SEQ ID NO 93
<211> LENGTH: 27
<212> TYPE: DNA
<213> ORGANISM: Oryza sativa

<400> SEQUENCE: 93
ttgaacggca agtttcacgc tgtcact    27

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 94
ggtaacggca agtttcacgc tgtcact    27

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 95
ttgccaggca agtttcacgc tgtcact    27

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 96
ttgaacttaa agtttcacgc tgtcact    27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 97
ttgaacggcc cttttcacgc tgtcact    27

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 98
ttgaacggca aggggcacgc tgtcact    27

<210> SEQ ID NO 99
<211> LENGTH: 27

```
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 99
ttgaacggca agtttacagc tgtcact                                            27

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 100
ttgaacggca agtttcacta ggtcact                                            27

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 101
ttgaacggca agtttcacgc ttgaact                                            27

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 102
ttgaacggca agtttcacgc tgtccag                                            27

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 103
ttgaactgca agtttcacgc tgtcact                                            27

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 104
ttgaacgtca agtttcacgc tgtcact                                            27

<210> SEQ ID NO 105
<211> LENGTH: 27
<212> TYPE: DNA
<213> ORGANISM: Artificial Sequence
```

```
<220> FEATURE:
<223> OTHER INFORMATION: Description of Artificial Sequence:Artificially
      synthesized sequence

<400> SEQUENCE: 105
ttgaacggaa agtttcacgc tgtcact                                          27

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 106
ttgaacggcc agtttcacgc tgtcact                                          27

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 107
ttgaacggca cgtttcacgc tgtcact                                          27

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 108
ttgaacggca attttcacgc tgtcact                                          27

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 109
ttgaacggca aggttcacgc tgtcact                                          27

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 110
ttgaacggca agtgtcacgc tgtcact                                          27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence:Artificially
```

-continued synthesized sequence

<400> SEQUENCE: 111
ttgaacggca agttgcacgc tgtcact                                              27

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 112
ttgaacggca ggtttcacgc tgtcact                                              27

<210> SEQ ID NO 113
<211> LENGTH: 113
<212> TYPE: PRT
<213> ORGANISM: Oryza sativa

<400> SEQUENCE: 113

Leu Leu Asn Ser Gly Glu Tyr Gln Val Ile Leu Arg Lys Glu Leu Thr
1               5                   10                  15

Lys Ser Asp Val Gly Asn Val Gly Arg Ile Val Leu Pro Lys Lys Asp
            20                  25                  30

Ala Glu Ala Ser Leu Pro Pro Leu Gln Arg Asp Pro Leu Ile Leu
        35                  40                  45

His Met Asp Asp Met Val Leu Pro Val Thr Trp Lys Phe Lys Tyr Arg
50                  55                  60

Tyr Trp Pro Asn Asn Lys Ser Arg Met Tyr Ile Leu Asp Ser Ala Gly
65                  70                  75                  80

Glu Phe Leu Lys Thr His Gly Leu Gln Ala Gly Asp Val Ile Ile Ile
                85                  90                  95

Tyr Lys Asn Leu Ala Pro Gly Lys Phe Ile Ile Arg Gly Glu Lys Ala
            100                 105                 110

Ile

<210> SEQ ID NO 114
<211> LENGTH: 112
<212> TYPE: PRT
<213> ORGANISM: Oryza sativa

<400> SEQUENCE: 114

Ala Lys Thr Asp Lys Asn Leu Arg Phe Leu Leu Gln Lys Val Leu Lys
1               5                   10                  15

Gln Ser Asp Val Gly Ser Leu Gly Arg Ile Val Leu Pro Lys Glu Ala
            20                  25                  30

Glu Val His Leu Pro Glu Leu Lys Thr Arg Asp Gly Val Ser Ile Pro
        35                  40                  45

Met Glu Asp Ile Gly Thr Ser Gln Val Trp Asn Met Arg Tyr Arg Phe
50                  55                  60

Trp Pro Asn Asn Lys Ser Arg Met Tyr Leu Leu Glu Asn Thr Gly Asp
65                  70                  75                  80

Phe Val Arg Ser Asn Glu Leu Gln Glu Gly Asp Phe Ile Val Ile Tyr
                85                  90                  95

Ser Asp Ile Lys Ser Gly Lys Tyr Leu Ile Arg Gly Val Lys Val Arg
            100                 105                 110

```
<210> SEQ ID NO 115
<211> LENGTH: 113
<212> TYPE: PRT
<213> ORGANISM: Zea Mays

<400> SEQUENCE: 115

Ala Lys Ala Asp Lys Asn Leu Arg Phe Leu Leu Gln Lys Val Leu Lys
1               5                   10                  15

Gln Ser Asp Val Gly Ser Leu Gly Arg Ile Val Leu Pro Lys Lys Glu
            20                  25                  30

Ala Glu Val His Leu Pro Glu Leu Lys Thr Arg Asp Gly Ile Ser Ile
        35                  40                  45

Pro Met Glu Asp Ile Gly Thr Ser Arg Val Trp Asn Met Arg Tyr Arg
    50                  55                  60

Phe Trp Pro Asn Asn Lys Ser Arg Met Tyr Leu Leu Glu Asn Thr Gly
65                  70                  75                  80

Glu Phe Val Arg Ser Asn Glu Leu Gln Glu Gly Asp Phe Ile Val Ile
                85                  90                  95

Tyr Ser Asp Val Lys Ser Gly Lys Tyr Leu Ile Arg Gly Val Lys Val
            100                 105                 110

Arg

<210> SEQ ID NO 116
<211> LENGTH: 449
<212> TYPE: PRT
<213> ORGANISM: Oryza sativa

<400> SEQUENCE: 116

Met Ala Gln Thr Val Leu Pro Pro Gly Phe Arg Phe His Pro Thr Asp
1               5                   10                  15

Val Glu Leu Val Ser Tyr Tyr Leu Lys Arg Lys Ile Met Gly Lys Lys
            20                  25                  30

Pro Leu Ile Gln Ala Ile Ser Asp Val Glu Leu Tyr Lys Phe Ala Pro
        35                  40                  45

Trp Asp Leu Pro Ala Gln Ser Cys Leu Gln Ser Arg Asp Leu Glu Trp
    50                  55                  60

Phe Phe Phe Cys Pro Arg Asp Lys Lys Tyr Pro Asn Gly Ser Arg Thr
65                  70                  75                  80

Asn Glu Ser Thr Pro Asn Gly Tyr Trp Lys Thr Ser Gly Lys Asp Arg
                85                  90                  95

Thr Ile Glu Leu Asn Ser Arg Ile Val Gly Ser Lys Lys Thr Leu Ile
            100                 105                 110

Phe His Glu Gly Lys Ala Pro Lys Gly Asn Arg Thr Asp Trp Val Met
        115                 120                 125

Tyr Glu Tyr Lys Met Glu Asp Asn Gln Leu Val Ser Ala Gly Phe Ser
    130                 135                 140

Lys Asp Asp Phe Val Leu Cys Lys Ile Phe Lys Lys Ser Gly Leu Gly
145                 150                 155                 160

Pro Arg Ile Gly Glu Gln Tyr Gly Ala Pro Phe Asn Glu Glu Trp
                165                 170                 175

Glu His Ala Asp Ala Glu Met Phe Pro Leu Leu Pro Asn Val Glu Thr
                180                 185                 190

Ser Val Phe Pro Leu Leu Pro Ser Glu Val Val Asn Ser Thr Asp
            195                 200                 205

Asp Thr Arg Val Gln Pro Ser Val Ala Ala Arg Ala Ile Glu Glu Leu
        210                 215                 220
```

```
Pro Val Gln His Leu Pro His Val Cys Ala Gly Asn Gly Ser Thr Tyr
225                 230                 235                 240

Gln Asn Ile Thr Val Thr Gly Glu Ser Ala Leu Met Glu Leu Pro Ser
            245                 250                 255

Gln His Ser Val Glu Ser Ile Gly Asp Glu Val Val Ser Val Asp Asn
        260                 265                 270

Cys Ser Asn Val Val Asn Asn Ala Asp Ser Pro Val Ile Glu Gly Leu
    275                 280                 285

Val Leu Glu Glu Leu Ser Arg Phe Leu Thr Asp Ser Pro His His Gly
290                 295                 300

Asn Pro Val Gly Glu His Ser Gly Leu Pro Pro Met Ser Glu Ala Glu
305                 310                 315                 320

Ala His Ala Phe Glu Val Ser Thr Asn Asp Leu Tyr Asn Glu Ile Ala
                325                 330                 335

Gly Leu Ala Glu Leu Gly Val Pro Asn Gly Asp Gly Phe Ser Pro Ser
            340                 345                 350

Asn Ala Gly Val Thr Glu Gln Gln Pro Thr Tyr Phe Gly Val Pro Asn
        355                 360                 365

Ser Glu Asn Tyr Val Asn Met Asp Asp Ile Phe Ala Pro Asp Thr Arg
    370                 375                 380

Leu Ser Tyr Ala Tyr Pro Leu Pro Asn Asn Gln Phe Trp His Tyr Pro
385                 390                 395                 400

Met Asp Gln Phe Thr Tyr Ser Thr Thr Leu Ser Ala Ala Phe Pro Ser
                405                 410                 415

Gly Asp Ser Arg Pro Thr Met Arg Ile Val Asp Asp Leu Pro Ala Ala
            420                 425                 430

Ala Asn Asn Gly Gly Phe Ala Ser Lys Pro Ser Met Gln Phe Pro Leu
        435                 440                 445

Ser

<210> SEQ ID NO 117
<211> LENGTH: 431
<212> TYPE: PRT
<213> ORGANISM: Holdeum vulgare

<400> SEQUENCE: 117

Met Ala Gln Thr Val Leu Pro Pro Gly Phe Arg Phe His Pro Thr Asp
1               5                   10                  15

Val Glu Leu Val Ser Tyr Tyr Leu Lys Arg Lys Ile Met Gly Lys Lys
            20                  25                  30

Leu Phe Val Gln Ala Ile Ser Glu Val Glu Leu Tyr Lys Phe Ala Pro
        35                  40                  45

Trp Asp Leu Pro Asp Lys Ser Cys Leu Gln Ser Lys Asp Leu Glu Trp
    50                  55                  60

Phe Phe Phe Cys Pro Arg Asp Lys Lys Tyr Pro Lys Gly Ser Arg Thr
65                  70                  75                  80

Asn Glu Ala Thr Pro Asn Gly Tyr Trp Lys Thr Ser Gly Lys Asp Arg
                85                  90                  95

Thr Ile Glu Leu Asn Ser Arg Ile Val Gly Leu Lys Lys Thr Leu Ile
            100                 105                 110

Phe His Glu Gly Lys Ala Pro Lys Gly Asn Arg Thr Asp Trp Val Met
        115                 120                 125

Tyr Glu Tyr Lys Met Glu Asp Glu Thr Leu Asp Ala Ala Gly Phe Ser
    130                 135                 140

Lys Asp Ala Tyr Val Leu Cys Lys Ile Phe Lys Lys Ser Gly Leu Gly
```

```
                145                 150                 155                 160
Pro Arg Ile Gly Glu Gln Tyr Gly Ala Pro Phe Asp Glu Asn Glu Trp
                    165                 170                 175

Glu Asn Leu Asp Val Cys Ser Ser Ile Phe Ser Phe Ala Pro Ser Ser
                180                 185                 190

Gly Val Glu Asp Pro Gln Val Glu Ser Ser Ala Leu Ala Thr Ala Val
            195                 200                 205

Ile Gln Glu Pro Phe Ala Pro Gln Gln Ser Val Gln Phe Ser Glu His
        210                 215                 220

Val Asn Ile Cys Ser Asn Glu Asp Asn Asn Ala Pro Pro Glu Ile Asp
225                 230                 235                 240

Gly Ile Trp Leu Glu Glu Leu Ala Met Phe Leu Asn Asp Ser Pro Asn
                245                 250                 255

His Asp Ile Ala Leu Pro Glu Asn Ser Gly Leu Pro Pro Met Ser Glu
                260                 265                 270

Leu Glu Ala Gln Ala Phe Glu Met Asn Thr Ala Glu Leu Tyr Asp Gln
                275                 280                 285

Leu Ala Gly Leu Ala Gln Ser Gly Asp Met Ser Asn Val Asn Phe Pro
        290                 295                 300

Ala Ala Asp Val Gly Val Thr Glu Asn Asp Phe Gln Gln Ser Asn Ser
305                 310                 315                 320

Gly Phe Ala Met Asp Asp Asp Tyr Ile Glu Leu Asp Asp Leu Phe Ala
                325                 330                 335

Pro Gly Glu Thr Phe Ser Tyr Asp Phe Ser Gly Glu Thr Phe Ser Tyr
                340                 345                 350

Asp Leu Thr Gly Gly Thr Phe Ser Tyr Asp Leu Ser Val Pro Asn Asn
            355                 360                 365

Gln Phe Leu Gln Tyr Pro Leu Asp Gln Ser Thr Asn Gly Ser His Tyr
        370                 375                 380

Gly Asp Gly Ala Thr Gln Ser Thr Phe Glu Ala Ser Gly Ser Leu Pro
385                 390                 395                 400

Pro Met Pro Ser Thr Phe Asp Asp Met Pro Ser Val Ser Asn Lys Pro
                405                 410                 415

Ala Asn Ser Asn Cys Leu Asn Pro Thr Met Glu Asp Pro Phe Ser
                420                 425                 430
```